United States Patent
Trollsas et al.

(10) Patent No.: US 9,770,351 B2
(45) Date of Patent: Sep. 26, 2017

(54) CRUSH RECOVERABLE POLYMER SCAFFOLDS

(71) Applicant: Abbott Cardiovascular Systems Inc., Santa Clara, CA (US)

(72) Inventors: Mikael Trollsas, San Jose, CA (US); Michael H. Ngo, San Jose, CA (US); Boris Anukhin, San Jose, CA (US); Alexander Nikanorov, Palo Alto, CA (US); Syed Hossainy, Hayward, CA (US); John E. Papp, Temecula, CA (US); Dudley Jayasinghe, Murietta, CA (US); Zella Solter, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 651 days.

(21) Appl. No.: 14/042,512

(22) Filed: Sep. 30, 2013

(65) Prior Publication Data
US 2014/0058499 A1    Feb. 27, 2014

Related U.S. Application Data

(63) Continuation of application No. 13/015,488, filed on Jan. 27, 2011, now Pat. No. 8,568,471.
(Continued)

(51) Int. Cl.
*A61F 2/82* (2013.01)
*A61F 2/958* (2013.01)
(Continued)

(52) U.S. Cl.
CPC ............. *A61F 2/958* (2013.01); *A61F 2/82* (2013.01); *A61F 2/844* (2013.01); *A61F 2/86* (2013.01);
(Continued)

(58) Field of Classification Search
CPC .......................... A61F 2250/0096–2250/0098
See application file for complete search history.

(56) References Cited

U.S. PATENT DOCUMENTS 2,697,863 A    12/1954    Moser
3,476,463 A    11/1969    Kreuzer
(Continued)

FOREIGN PATENT DOCUMENTS

CN    1241442    1/2000
DE    44 07 079    9/1994
(Continued)

OTHER PUBLICATIONS

International Search Report for PCT/US2008/062607, mailed Aug. 5, 2008, 4 pgs.
(Continued)

*Primary Examiner* — Yashita Sharma
*Assistant Examiner* — Rebecca Preston
(74) *Attorney, Agent, or Firm* — Squire Patton Boggs (US) LLP

(57) ABSTRACT

A medical device includes a polymer scaffold crimped to a catheter having an expansion balloon. The scaffold, after being deployed by the balloon, provides a crush recovery of about 90% after the diameter of the scaffold has been pinched or crushed by 50%. The scaffold has a pattern including an asymmetric closed cell connecting links connecting the closed cells.

36 Claims, 31 Drawing Sheets

Related U.S. Application Data

(60) Provisional application No. 61/385,891, filed on Sep. 23, 2010, provisional application No. 61/385,902, filed on Sep. 23, 2010, provisional application No. 61/299,968, filed on Jan. 30, 2010.

(51) Int. Cl.

| | | |
|---|---|---|
| *A61F 2/91* | (2013.01) | |
| *A61L 27/00* | (2006.01) | |
| *A61L 31/06* | (2006.01) | |
| *A61F 2/86* | (2013.01) | |
| *A61F 2/844* | (2013.01) | |
| *B29C 35/08* | (2006.01) | |
| *A61L 31/14* | (2006.01) | |
| *A61F 2/89* | (2013.01) | |
| *A61F 2/915* | (2013.01) | |
| *A61F 2/95* | (2013.01) | |
| *B29K 67/00* | (2006.01) | |
| *B29L 23/00* | (2006.01) | |
| *B29L 31/00* | (2006.01) | |

(52) U.S. Cl.
CPC .............. *A61F 2/91* (2013.01); *A61F 2/915* (2013.01); *A61L 27/00* (2013.01); *A61L 31/06* (2013.01); *A61L 31/14* (2013.01); *B29C 35/08* (2013.01); *A61F 2/89* (2013.01); *A61F 2002/825* (2013.01); *A61F 2002/91558* (2013.01); *A61F 2002/91566* (2013.01); *A61F 2002/91575* (2013.01); *A61F 2002/9522* (2013.01); *A61F 2210/0004* (2013.01); *A61F 2210/0014* (2013.01); *A61F 2210/0019* (2013.01); *A61F 2210/0076* (2013.01); *A61F 2230/0006* (2013.01); *A61F 2230/0008* (2013.01); *A61F 2250/0067* (2013.01); *A61F 2250/0096* (2013.01); *A61F 2250/0098* (2013.01); *B29C 2035/0838* (2013.01); *B29K 2067/046* (2013.01); *B29L 2023/00* (2013.01); *B29L 2031/7543* (2013.01); *Y10T 29/4987* (2015.01); *Y10T 29/49826* (2015.01); *Y10T 29/49908* (2015.01); *Y10T 29/49925* (2015.01); *Y10T 29/49927* (2015.01)

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,886,870 A | 12/1989 | D'Amore et al. |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,061,281 A | 10/1991 | Mares et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,380,976 A | 1/1995 | Couch |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury |
| 5,443,500 A | 8/1995 | Sigwart |
| 5,455,040 A | 10/1995 | Marchant |
| 5,464,650 A | 11/1995 | Berg et al. |
| 5,486,546 A | 1/1996 | Mathiesen et al. |
| 5,500,013 A | 3/1996 | Buscemi et al. |
| 5,502,158 A | 3/1996 | Sinclair et al. |
| 5,507,799 A | 4/1996 | Sumiya |
| 5,514,154 A | 5/1996 | Lau et al. |
| 5,514,379 A | 5/1996 | Weissleder et al. |
| 5,525,646 A | 6/1996 | Lundgren et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,565,215 A | 10/1996 | Gref et al. |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,603,722 A | 2/1997 | Phan et al. |
| 5,605,696 A | 2/1997 | Eury et al. |
| 5,607,442 A | 3/1997 | Fischell et al. |
| 5,607,467 A | 3/1997 | Froix |

(56) References Cited

U.S. PATENT DOCUMENTS

| | | |
|---|---|---|
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,656,186 A | 8/1997 | Mourou et al. |
| 5,667,767 A | 9/1997 | Greff et al. |
| 5,667,796 A | 9/1997 | Otten |
| 5,670,161 A | 9/1997 | Healy et al. |
| 5,670,558 A | 9/1997 | Onishi et al. |
| 5,686,540 A | 11/1997 | Kakizawa |
| 5,693,085 A | 12/1997 | Buirge et al. |
| 5,700,286 A | 12/1997 | Tartaglia et al. |
| 5,700,901 A | 12/1997 | Hurst et al. |
| 5,704,082 A | 1/1998 | Smith |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,725,572 A | 3/1998 | Lam et al. |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,327 A | 4/1998 | Frantzen |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,770,609 A | 6/1998 | Grainger et al. |
| 5,780,807 A | 7/1998 | Saunders |
| 5,800,516 A | 9/1998 | Fine et al. |
| 5,811,447 A | 9/1998 | Kunz et al. |
| 5,824,042 A | 10/1998 | Lombardi et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,925,061 A | 7/1999 | Ogi et al. |
| 5,928,280 A | 7/1999 | Hansen et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,007,845 A | 12/1999 | Domb et al. |
| 6,010,445 A | 1/2000 | Armini et al. |
| 6,015,541 A | 1/2000 | Greff et al. |
| 6,022,374 A | 2/2000 | Imran |
| 6,042,606 A | 3/2000 | Frantzen |
| 6,042,875 A | 3/2000 | Ding et al. |
| 6,045,568 A | 4/2000 | Igaki et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,066,167 A | 5/2000 | Lau et al. |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,110,483 A | 8/2000 | Whitbourne |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,131,266 A | 10/2000 | Saunders |
| 6,150,630 A | 11/2000 | Perry et al. |
| 6,153,252 A | 11/2000 | Hossainy et al. |
| 6,156,062 A | 12/2000 | McGuinness |
| 6,159,951 A | 12/2000 | Karpeisky et al. |
| 6,160,084 A | 12/2000 | Langer et al. |
| 6,160,240 A | 12/2000 | Momma et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,206,911 B1 | 3/2001 | Milo |
| 6,210,715 B1 | 4/2001 | Starling et al. |
| 6,224,626 B1 | 5/2001 | Steinke |
| 6,228,845 B1 | 5/2001 | Donovan et al. |
| 6,231,598 B1 | 5/2001 | Berry et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,260,976 B1 | 7/2001 | Endou et al. |
| 6,273,910 B1 | 8/2001 | Limon |
| 6,273,913 B1 | 8/2001 | Wright et al. |
| 6,281,262 B1 | 8/2001 | Shikinami |

(56) References Cited

U.S. PATENT DOCUMENTS

| | | |
|---|---|---|
| 6,283,234 B1 | 9/2001 | Torbet |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,295,168 B1 | 9/2001 | Hofnagle et al. |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,355,058 B1 | 3/2002 | Pacetti et al. |
| 6,361,557 B1 | 3/2002 | Gittings et al. |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,752 B1 | 6/2002 | Boatman et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,471,721 B1 | 10/2002 | Dang |
| 6,475,779 B2 | 11/2002 | Mathiowithz et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,506,437 B1 | 1/2003 | Harish et al. |
| 6,511,748 B1 | 1/2003 | Barrows |
| 6,517,888 B1 | 2/2003 | Weber |
| 6,521,865 B1 | 2/2003 | Jones et al. |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,563,080 B2 | 5/2003 | Shapovalov et al. |
| 6,563,998 B1 | 5/2003 | Farah |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,582,472 B2 | 6/2003 | Hart |
| 6,585,755 B2 | 7/2003 | Jackson et al. |
| 6,589,227 B2 | 7/2003 | S.o slashed.nderskov Klint |
| 6,592,614 B2 | 7/2003 | Lenker et al. |
| 6,592,617 B2 | 7/2003 | Thompson |
| 6,613,072 B2 | 9/2003 | Lau et al. |
| 6,616,689 B1 | 9/2003 | Ainsworth et al. |
| 6,620,194 B2 | 9/2003 | Ding et al. |
| 6,626,939 B1 | 9/2003 | Burnside et al. |
| 6,629,994 B2 | 10/2003 | Gomez et al. |
| 6,635,269 B1 | 10/2003 | Jennissen |
| 6,645,243 B2 | 11/2003 | Vallana et al. |
| 6,652,579 B1 * | 11/2003 | Cox ............... A61F 2/91 623/1.15 |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,696,667 B1 | 2/2004 | Flanagan |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,758,859 B1 | 7/2004 | Dang et al. |
| 6,764,505 B1 | 7/2004 | Hossainy et al. |
| 6,780,261 B2 | 8/2004 | Trozera |
| 6,801,368 B2 | 10/2004 | Coufal et al. |
| 6,805,898 B1 | 10/2004 | Wu et al. |
| 6,818,063 B1 | 11/2004 | Kerrigan |
| 6,822,186 B2 | 11/2004 | Strassl et al. |
| 6,846,323 B2 | 1/2005 | Yip et al. |
| 6,852,124 B2 | 2/2005 | Cox et al. |
| 6,852,946 B2 | 2/2005 | Groen et al. |
| 6,858,680 B2 | 2/2005 | Gunatillake et al. |
| 6,867,389 B2 | 3/2005 | Shapovalov et al. |
| 6,878,758 B2 | 4/2005 | Martin et al. |
| 6,890,350 B1 | 5/2005 | Walak |
| 6,891,126 B2 | 5/2005 | Matile |
| 6,899,729 B1 | 5/2005 | Cox et al. |
| 6,911,041 B1 | 6/2005 | Zscheeg |
| 6,913,762 B2 | 7/2005 | Caplice et al. |
| 6,918,928 B2 | 7/2005 | Wolinsky et al. |
| 6,926,733 B2 | 8/2005 | Stinson |
| 6,943,964 B1 | 9/2005 | Zhang et al. |
| 6,981,982 B2 | 1/2006 | Armstrong et al. |
| 6,981,987 B2 | 1/2006 | Huxel et al. |
| 6,997,944 B2 | 2/2006 | Harrison et al. |
| 7,022,132 B2 | 4/2006 | Kocur |
| 7,128,737 B1 | 10/2006 | Goder et al. |
| 7,163,555 B2 | 1/2007 | Dinh |
| 7,166,099 B2 | 1/2007 | Devens, Jr. |
| 7,226,475 B2 | 6/2007 | Lenz et al. |
| 7,243,408 B2 | 7/2007 | Vietmeier |
| 7,273,492 B2 | 9/2007 | Cheng et al. |
| 7,273,495 B2 | 9/2007 | Limon |
| 7,326,245 B2 | 2/2008 | Rosenthal et al. |
| 7,331,986 B2 | 2/2008 | Brown et al. |
| 7,498,042 B2 | 3/2009 | Igaki et al. |
| 7,500,988 B1 | 3/2009 | Butaric et al. |
| 7,666,342 B2 | 2/2010 | Limon et al. |
| 7,731,740 B2 | 6/2010 | LaFont et al. |
| 7,731,890 B2 | 6/2010 | Gale et al. |
| 7,740,791 B2 | 6/2010 | Kleine et al. |
| 7,761,968 B2 | 7/2010 | Huang et al. |
| 7,763,066 B2 | 7/2010 | Parker |
| 7,776,926 B1 | 8/2010 | Hossainy et al. |
| 7,887,579 B2 | 2/2011 | Mangiardi et al. |
| 7,971,333 B2 | 7/2011 | Gale et al. |
| 8,002,817 B2 | 8/2011 | Limon |
| 8,099,849 B2 | 1/2012 | Gale et al. |
| 8,206,436 B2 | 6/2012 | Mangiardi et al. |
| 8,211,163 B2 | 7/2012 | Dakin et al. |
| 8,252,215 B2 | 8/2012 | Wang |
| 8,261,423 B2 | 9/2012 | Jow et al. |
| 8,303,296 B2 | 11/2012 | Kleiner et al. |
| 8,303,644 B2 | 11/2012 | Lord et al. |
| 8,303,645 B2 | 11/2012 | Oepen et al. |
| 8,323,329 B2 | 12/2012 | Gale et al. |
| 8,370,120 B2 | 2/2013 | Lord |
| 8,388,673 B2 | 3/2013 | Yang et al. |
| 8,539,663 B2 | 9/2013 | Wang et al. |
| 8,568,471 B2 | 10/2013 | Trollsas et al. |
| 8,679,394 B2 | 3/2014 | Harrington et al. |
| 8,726,483 B2 | 5/2014 | Stankus et al. |
| 8,808,353 B2 | 8/2014 | Anukhin et al. |
| 9,161,852 B2 | 10/2015 | Stankus et al. |
| 9,198,785 B2 | 12/2015 | Trollsas et al. |
| 9,345,602 B2 | 5/2016 | Ngo et al. |
| 9,554,928 B2 | 1/2017 | Stankus et al. |
| 9,642,730 B2 | 5/2017 | Ngo et al. |
| 2001/0001317 A1 | 5/2001 | Duerig et al. |
| 2001/0018610 A1 | 8/2001 | Limon |
| 2001/0021871 A1 | 9/2001 | Stinson |
| 2001/0027339 A1 | 10/2001 | Boatman et al. |
| 2001/0029398 A1 | 10/2001 | Jadhav |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0013616 A1 | 1/2002 | Carter et al. |
| 2002/0032486 A1 | 3/2002 | Lazarovitz et al. |

(56) References Cited

U.S. PATENT DOCUMENTS

| | | |
|---|---|---|
| 2002/0062148 A1 | 5/2002 | Hart |
| 2002/0065553 A1 | 5/2002 | Weber |
| 2002/0103528 A1 | 8/2002 | Schaldach et al. |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0143386 A1 | 10/2002 | Davila et al. |
| 2002/0161114 A1 | 10/2002 | Gunatillake et al. |
| 2002/0190038 A1 | 12/2002 | Lawson |
| 2002/0193862 A1 | 12/2002 | Mitelberg et al. |
| 2002/0198558 A1 | 12/2002 | Briscoe et al. |
| 2002/0198588 A1 | 12/2002 | Armstrong |
| 2003/0004563 A1 | 1/2003 | Jackson et al. |
| 2003/0023301 A1 | 1/2003 | Cox et al. |
| 2003/0028241 A1 | 2/2003 | Stinson |
| 2003/0028245 A1 | 2/2003 | Barclay et al. |
| 2003/0033001 A1 | 2/2003 | Igaki |
| 2003/0039689 A1 | 2/2003 | Chen et al. |
| 2003/0050688 A1 | 3/2003 | Fischell et al. |
| 2003/0060872 A1 | 3/2003 | Gomringer et al. |
| 2003/0065355 A1 | 4/2003 | Weber |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0108588 A1 | 6/2003 | Chen |
| 2003/0121148 A1 | 7/2003 | DiCaprio |
| 2003/0153971 A1 | 8/2003 | Chandrasekaran |
| 2003/0155328 A1 | 8/2003 | Huth |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer et al. |
| 2003/0236565 A1 | 12/2003 | DiMatteo et al. |
| 2004/0015228 A1 | 1/2004 | Lombardi et al. |
| 2004/0034405 A1 | 2/2004 | Dickson |
| 2004/0044399 A1 | 3/2004 | Ventura |
| 2004/0044400 A1 | 3/2004 | Cheng et al. |
| 2004/0073291 A1 | 4/2004 | Brown et al. |
| 2004/0088039 A1 | 5/2004 | Lee et al. |
| 2004/0093077 A1 | 5/2004 | White et al. |
| 2004/0098090 A1 | 5/2004 | Williams et al. |
| 2004/0098095 A1 | 5/2004 | Burnside et al. |
| 2004/0106987 A1 | 6/2004 | Palasis et al. |
| 2004/0111149 A1 | 6/2004 | Stinson |
| 2004/0122509 A1 | 6/2004 | Brodeur |
| 2004/0126405 A1 | 7/2004 | Sahatjian |
| 2004/0127970 A1 | 7/2004 | Saunders et al. |
| 2004/0143180 A1 | 7/2004 | Zhong et al. |
| 2004/0143317 A1 | 7/2004 | Stinson et al. |
| 2004/0167610 A1 | 8/2004 | Fleming, III |
| 2004/0167619 A1 | 8/2004 | Case et al. |
| 2004/0181236 A1 | 9/2004 | Eidenschink et al. |
| 2004/0204750 A1 | 10/2004 | Dinh |
| 2004/0236409 A1 | 11/2004 | Pelton et al. |
| 2004/0236428 A1 | 11/2004 | Burkinshaw et al. |
| 2005/0004653 A1 | 1/2005 | Gerberding et al. |
| 2005/0004663 A1 | 1/2005 | Llanos et al. |
| 2005/0015138 A1 | 1/2005 | Schuessler et al. |
| 2005/0021131 A1 | 1/2005 | Venkatraman et al. |
| 2005/0060025 A1 | 3/2005 | Mackiewicz et al. |
| 2005/0087520 A1 | 4/2005 | Wang et al. |
| 2005/0107865 A1 | 5/2005 | Clifford et al. |
| 2005/0111500 A1 | 5/2005 | Harter et al. |
| 2005/0147647 A1 | 7/2005 | Glauser et al. |
| 2005/0154450 A1 | 7/2005 | Larson et al. |
| 2005/0157382 A1 | 7/2005 | Kafka et al. |
| 2005/0187615 A1 | 8/2005 | Williams et al. |
| 2005/0211680 A1 | 9/2005 | Li et al. |
| 2005/0283226 A1 | 12/2005 | Haverkost |
| 2005/0283228 A1 | 12/2005 | Stanford |
| 2006/0020324 A1 | 1/2006 | Schmid et al. |
| 2006/0020330 A1 | 1/2006 | Huang et al. |
| 2006/0025847 A1 | 2/2006 | Parker |
| 2006/0033240 A1 | 2/2006 | Weber et al. |
| 2006/0076708 A1 | 4/2006 | Huang et al. |
| 2006/0106453 A1 | 5/2006 | Sirhan et al. |
| 2006/0120418 A1 | 6/2006 | Harter et al. |
| 2006/0173528 A1 | 8/2006 | Feld et al. |
| 2006/0241741 A1 | 10/2006 | Lootz |
| 2006/0265050 A1 | 11/2006 | Morris et al. |
| 2006/0271170 A1 | 11/2006 | Gale et al. |
| 2007/0156230 A1 | 7/2007 | Dugan et al. |
| 2007/0191926 A1 | 8/2007 | Nikanorov et al. |
| 2007/0260302 A1 | 11/2007 | Igaki |
| 2007/0266542 A1 | 11/2007 | Melsheimer |
| 2007/0271763 A1 | 11/2007 | Huang et al. |
| 2007/0282428 A1 | 12/2007 | Igaki |
| 2007/0282433 A1 | 12/2007 | Limon et al. |
| 2007/0283552 A1 | 12/2007 | Gale et al. |
| 2007/0293938 A1 | 12/2007 | Gale et al. |
| 2008/0001333 A1 | 1/2008 | Kleine et al. |
| 2008/0009938 A1 | 1/2008 | Huang et al. |
| 2008/0015684 A1 | 1/2008 | Wu |
| 2008/0033532 A1 | 2/2008 | Dave |
| 2008/0051877 A1 | 2/2008 | Hsiao et al. |
| 2008/0147164 A1 | 6/2008 | Gale et al. |
| 2008/0177373 A1 | 7/2008 | Huang et al. |
| 2008/0177374 A1 | 7/2008 | Zheng et al. |
| 2008/0188924 A1 | 8/2008 | Prabhu |
| 2008/0275537 A1 | 11/2008 | Limon |
| 2009/0001633 A1 | 1/2009 | Limon |
| 2009/0076594 A1 | 3/2009 | Sabaria |
| 2009/0105797 A1 | 4/2009 | Roeder et al. |
| 2009/0105800 A1 | 4/2009 | Sabaria |
| 2009/0146348 A1 | 6/2009 | Huang et al. |
| 2009/0157160 A1 | 6/2009 | van der Leest et al. |
| 2009/0163989 A1 | 6/2009 | Contiliano et al. |
| 2009/0204203 A1 | 8/2009 | Allen et al. |
| 2009/0216311 A1 | 8/2009 | Flagle et al. |
| 2009/0248131 A1 | 10/2009 | Greenan |
| 2010/0004734 A1 | 1/2010 | Ramzipoor et al. |
| 2010/0004735 A1 | 1/2010 | Yang et al. |
| 2010/0025894 A1 | 2/2010 | Kleiner et al. |
| 2010/0174358 A1 | 7/2010 | Rabkin et al. |
| 2010/0204778 A1 | 8/2010 | LaFont et al. |
| 2010/0217373 A1 | 8/2010 | Boyle et al. |
| 2010/0244329 A1 | 9/2010 | Hossainy et al. |
| 2010/0256736 A1 | 10/2010 | Purdy et al. |
| 2010/0256742 A1 | 10/2010 | Kleine et al. |
| 2010/0274349 A1 | 10/2010 | Lord et al. |
| 2010/0289191 A1 | 11/2010 | Gale et al. |
| 2010/0292777 A1 | 11/2010 | Meyer et al. |
| 2010/0298926 A1 | 11/2010 | Igaki |
| 2010/0323091 A1 | 12/2010 | Castro et al. |
| 2011/0057356 A1 | 3/2011 | Jow |
| 2011/0066222 A1 | 3/2011 | Wang et al. |
| 2011/0112627 A1 | 5/2011 | Gale et al. |
| 2011/0130822 A1 | 6/2011 | Cottone |
| 2011/0172759 A1 | 7/2011 | Schmid et al. |
| 2011/0190871 A1 | 8/2011 | Trollsas et al. |
| 2011/0190872 A1 | 8/2011 | Anukhin et al. |
| 2011/0230957 A1 | 9/2011 | Bonsignore et al. |
| 2011/0230959 A1 | 9/2011 | Pienknagura |
| 2011/0245904 A1 | 10/2011 | Pacetti et al. |
| 2011/0260352 A1 | 10/2011 | Tang et al. |
| 2011/0270383 A1 | 11/2011 | Jow et al. |
| 2011/0270384 A1 | 11/2011 | Lord |
| 2011/0271513 A1 | 11/2011 | Wang |
| 2011/0277305 A1 | 11/2011 | Limon |
| 2011/0278771 A1 | 11/2011 | Kleiner et al. |
| 2012/0029618 A1 | 2/2012 | Tischler et al. |
| 2012/0029624 A1 | 2/2012 | Dierking et al. |
| 2012/0042501 A1 | 2/2012 | Wang et al. |
| 2012/0073733 A1 | 3/2012 | Ngo et al. |
| 2012/0271396 A1 | 10/2012 | Zheng et al. |
| 2012/0285609 A1 | 11/2012 | Wang |
| 2012/0299226 A1 | 11/2012 | Wang et al. |
| 2012/0316635 A1 | 12/2012 | Jow et al. |
| 2012/0319333 A1 | 12/2012 | Huang et al. |
| 2012/0330403 A1 | 12/2012 | Gomez et al. |
| 2013/0026681 A1 | 1/2013 | Kleiner et al. |

(56) References Cited

U.S. PATENT DOCUMENTS

| | | | |
|---|---|---|---|
| 2013/0090718 A1 | 4/2013 | Lord et al. |
| 2013/0150943 A1 | 6/2013 | Zheng et al. |
| 2013/0181380 A1 | 7/2013 | Yang et al. |
| 2013/0255853 A1 | 10/2013 | Wang et al. |
| 2013/0325104 A1 | 12/2013 | Wu |
| 2013/0325105 A1 | 12/2013 | Wu |
| 2013/0325107 A1 | 12/2013 | Wu |
| 2013/0331926 A1 | 12/2013 | Wu |
| 2014/0031921 A1 | 1/2014 | Trollsas et al. |
| 2014/0039604 A1 | 2/2014 | Trollsas et al. |
| 2014/0067044 A1 | 3/2014 | Trollsas et al. |
| 2014/0075735 A1 | 3/2014 | Trollsas et al. |
| 2014/0090231 A1 | 4/2014 | Trollsas et al. |
| 2014/0330363 A1 | 11/2014 | Anukhin et al. |
| 2015/0028513 A1 | 1/2015 | Cottone |
| 2016/0030217 A1 | 2/2016 | Trollsas et al. |
| 2017/0095361 A1 | 4/2017 | Stankus et al. |

FOREIGN PATENT DOCUMENTS

| | | |
|---|---|---|
| DE | 197 31 021 | 1/1999 |
| DE | 198 56 983 | 12/1999 |
| DE | 29724852 | 2/2005 |
| DE | 103 61942 | 7/2005 |
| DE | 10 2004 045994 | 3/2006 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0583170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0714641 | 6/1996 |
| EP | 0842729 | 5/1998 |
| EP | 0 970 711 | 1/2000 |
| EP | 1210 922 | 6/2002 |
| EP | 1 591 079 | 11/2005 |
| EP | 1 656 905 | 5/2006 |
| EP | 1 859 823 | 11/2007 |
| EP | 2 152 207 | 11/2008 |
| GB | 2 247 696 | 3/1992 |
| JP | 4-33791 | 2/1992 |
| JP | 7-124766 | 5/1995 |
| JP | 10-166156 | 6/1998 |
| JP | 2003-53577 | 2/2003 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/27587 | 10/1995 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/20429 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/26162 | 4/2002 |
| WO | WO 02/38325 | 5/2002 |
| WO | WO 03/015978 | 2/2003 |
| WO | WO 03/057075 | 7/2003 |
| WO | WO 2004/019820 | 3/2004 |
| WO | WO 2004/023985 | 3/2004 |
| WO | WO 2004/062533 | 7/2004 |
| WO | WO 2004/112863 | 12/2004 |
| WO | WO 2005/023480 | 3/2005 |
| WO | WO-2005/028014 A1 | 3/2005 |
| WO | WO 2007/021706 | 2/2007 |
| WO | WO 2007/081551 | 7/2007 |
| WO | WO 2007/142750 | 12/2007 |
| WO | WO 2007/146354 | 12/2007 |
| WO | WO-2007/149457 A1 | 12/2007 |
| WO | WO 2008/137821 | 11/2008 |
| WO | WO 2009/121048 | 10/2009 |

OTHER PUBLICATIONS

European Search Report for appl.. No. 08 747619.8, mailed Sep. 27, 2011, 5 pgs.
Translation of Notice of Reason for Rejection for JP appl. No. 2010-506710, dispatched Sep. 25, 2012, 3 pgs.
Verheye "Overview of Novolimus Elution and Myolimus Elution from Durable and Bioabsorbable Polymers", presentation, Elixir Medical, 22 pgs. (2010).
Acquarulo et al., *Enhancing Medical Device Performance with Nanocomposite Poly*, Med. Device Link, www.devicelink.com/grabber.php3?URL downloaded Mar. 26, 2007, 4 pgs.
Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23(4), pp. 242-243 (1978).
Bull, *Parylene Coating for Medical Applications*, Medical Product Manufacturing News 18, 1 pg. (Mar. 1993).
Casper et al., *Fiber-Reinforced Absorbable Composite for Orthopedic Surgery*, Polymeric Materials Science and Engineering, vol. 53 pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Eidelman et al., *Characterization of Combinatorial Polymer Blend Composition Gradients by FTIR Microspectroscopy*, J. Res. Natl. Inst. Stnadards and Technol., vol. 109, No. 2, pp. 219-231 (2004).
Elbert et al., *Conjugate Addition Reactions Combined with Free-Radical Cross-Linking for the Design of Materials for Tissue Engineering*, Biomacromolecules, vol. 2, pp. 430-441 (2001).
Fan et al., *Plasma Absorption of Femtosecond Laser Pulses in Dielectrics*, J. of Heat Transfer, vol. 124, pp. 275-283 (2002).
Feng-Chun et al., *Assessment of Tissue Blood Flow Following Small Artery Welding with an Intraluminal Dissolvable Stent*, Microsurgery, vol. 19(3), pp. 148-152 (1999).
Hahn et al., *Biocompatibility of Glow-Discharge-Polymerized Films and Vacuum-Deposited Paylene*, J Appled Polymer Sci, vol. 38, pp. 55-64 (1984).
Hahn et al., *Glow Discharge Polymers as Coatings for Implanted Devices, ISA*, pp. 109-111 (1981).

(56) References Cited

OTHER PUBLICATIONS

He et al., *Assessment of Tissue Blood Flow Following Small Artery Welding with an Intraluminal Dissolvable Stent*, Microsurgery, vol. 19(3), pp. 148-152 (1999).
Hoffnagle et al., *Design and performance of a refractive optical system that converts a Gaussian to a flattop beam*, Applied Optics, vol. 39, No. 30 pp. 5499-5499 (2000).
International Search Rep. For PCT/US2007/015561 filed Jul. 6, 2007, mailed Dec. 4, 2007, 7 pgs.
International Search Report for PCT/US2006/049269, filed Dec. 21, 2006, mailed Jun. 15, 2007, 19 pgs.
Kelley et al., *Totally Resorbable High-Strength Composite Material*, Advances in Biomedical Polymers, vol. 35, pp. 75-85 (1987).
Kubies et al., *Microdomain Structure in polylactide-block-poly(ethylene oxide) copolymer films*, Biomaterials, vol. 21, pp. 529-536 (2000).
Kutryk et al., *Coronary Stenting: Current Perspectives*, a companion to the Handbook of Coronary Stents, pp. 1-16 (1999).
Martin et al., *Enhancing the biological activity of immobilized osteopontin using a type-1 collagen affinity coating*, J. Biomed. Mater. Res., vol. 70A, pp. 10-19 (2004).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., vol. 1(4), pp. 438-448 (Jul./Aug. 1990).
nanoComposix,products, www.nanocomposix.com, dowhloaded Mar. 26, 2007, 2 pgs.
Nanosiliver, Photocatalyst and Nanocomposite Material, http://eng.nanocomposite.net downloaded Mar. 26, 2007, 1 pg.
Nichols et al., *Electrical Insulation of Implantable Devices by Composite Polymer Coatings*, ISA Transactions, vol. 26(4), pp. 15-18 (1987).
Peuster et al., *A novel approach to temporary stenting: degradable cardiovascular stents produced from corrodible metal-results 6-18 months after implantation into New Zealand white rabbits*, Heart, vol. 86, pp. 563-569 (2001).
Pietrzak et al., *Bioabsorbable Fixation Devices: Status for the Craniomaxillofacial Surgeon*, J. Craniofaxial Surg., vol. 2, pp. 92-96 (1997).
Pietrzak et al., *Bioresorbable implants—practical considerations*, Bone, vol. 19, No. 1, Supplement Jul. 1996, pp. 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).
Schmidt et al., *Long-Term Implants of Parylene-C Coated Microelectrodes*, Med & Biol Eng & Comp, vol. 26(1), pp. 96-101 (Jan. 1988).
Spagnuolo et al., *Gas 1 is induced by VE-cadherin and vascular endothelial growth factor and inhibits endothelial cell apoptosis*, Blood, vol. 103, pp. 3005-3012 (2004).
Sun et al., "Inert gas beam delivery for ultrafast laser micromachining at ambient pressure", Am. Inst. Of Physics, 6 pgs.
Tamai et al., *Initial and 6-Month Results of Biodegradable Poly-l-Lactic Acid Coronary Stents in Humans*, Circulation, pp. 399-404 (Jul. 25, 2000).
Tsuji et al., *Biodegradable Polymeric Stents*, Current Interventional Cardiology Reports, vol. 3, pp. 10-17 (2001).
Völkel et al., *Targeting of immunoliposomes to endothelial cells using a single-chain Fv fragment directed against human endoglin (CD105)*, Biochimica et Biophysica Acta 1663, pp. 158-166 (2004).
von Recum et al., *Degradation of polydispersed poly(L-lactic acid) to modulate lactic acid release*, Biomaterials, vol. 16, pp. 441-445 (1995).
Yau et al., Modern Size-Exclusion Liquid Chromatography, Wiley-Interscience Publication, IX-XV (1979).
Zhang et al., "Single-element laser beam shaper for uniform flat-top profiles" Optics Express, vol. 11, No. 16, pp. 1942-1948 (2003).
U.S. Appl. No. 11/009,977, filed Dec. 9, 2004, Pacetti.
U.S. Appl. No. 11/325,974, filed Jan. 4, 2006, Dugan et al.
U.S. Appl. No. 12/172,020, filed Jul. 11, 2008, Wang.
U.S. Appl. No. 14/042,496, filed Sep. 30, 2013, Trollsas et al.
U.S. Appl. No. 14/085,716, filed Nov. 20, 2013, Trollsas et al.
U.S. Appl. No. 14/097,172, filed Dec. 4, 2013, Trollsas et al.
Verheye "Overview of Novolimus Elution and Myolimus Elution from Durable and Bioabsorbable Polymers", presentation, Elixir Medical, 22 pgs. (2011).
Yan et al., "Elixir Medical's bioresorbable drug eluting stent (BDES) programme: an overview", Eurointervention Supplement vol. 5 (Supplement F) pp. F80-F82 (2009).
Duerig et al., "A Comparison of balloon- and self-expanding stents", Min. Invas. Ther. & Allied Technol. 2002: 11(4) 173-178.
Duerig et al., "An overview of superelastic stent design", Min. Invas. Ther. & Allied Technol. pp. 235-246 (2000).
Jie et al., "Formula for Elastic Radial Stiffness of the Tubular Vascular Stent", IFMBE Proceedings 31, pp. 1435-1438, 2010.
Lachowitzer, "Testing Radial Strength and Stiffness using Segmental Compression", ASTM International, Jul. 2004.
Yoshino et al., "Design and Evaluation of Self-Expanding Stents Suitable for Diverse Clinical Manifestation Based on Mechanical Engineering", Intech, pp. 182-207 (2012).

\* cited by examiner

| Attribute | FIGS. 3,4 and 5A | Scaffold examples having crush recovery and reduced crimp profile | | |
|---|---|---|---|---|
| | | V2 | V23/008 | V23/014 |
| Total length (mm) | - | 36 | 38 | 38 |
| Number of crowns | - | 9 | 9 | 9 |
| Number of links | - | 3 | 3 | 3 |
| wall thickness (in) | 235 | .008 | .008 | .014 |
| OD (mm) | - | 7 | 9 | 9 |
| Strut width (in) | 361 | 0.0085 | 0.011 | 0.011 |
| Crown width (in) | 362 | 0.0085 | 0.011 | 0.011 |
| Link width (in) | 363 | 0.007 | 0.006 | 0.006 |
| Strut length (in) | 364 | 0.071 | 0.081 | 0.081 |
| Ring height (in) | 365 | 0.057 | 0.052 | 0.052 |
| angle (deg.) | 366 | 65 | 100 | 100 |
| angle (deg.) | 367 | 67 | 95 | 95 |
| angle (deg.) | 368 | 59 | 104 | 104 |
| angle (deg.) | 368 | 57 | 104 | 104 |
| crown radius (in) | 369 | 0.0067 | 0.006 | 0.006 |
| crown radius (in) | 370 | 0.0152 | 0.017 | 0.017 |
| crown radius (in) | 371 | 0.0078 | 0.008 | 0.008 |
| crown radius (in) | 372 | 0.0163 | 0.017 | 0.017 |
| crown radius (in) | 373 | 0.0081 | 0.0081 | 0.0081 |
| crown radius (in) | 374 | 0.0166 | 0.015 | 0.015 |
| Range of Radial Strength (N/mm) | - | 0.30-0.45 | 0.30-0.45 | 0.45-0.65 |
| Range of Radial Stiffness (N/mm) | - | 0.50-0.70 | 0.50-0.70 | 0.90-1.10 |
| Range of Crush Recovery (%) at 50% pinching | - | 87-95 | 87-95 | 80-85 |

FIG. 6A

| Attribute | FIGS. 2,3 & 5B | Scaffold example having crush recovery and reduced crimp profile ("V59") |
|---|---|---|
| pre-crimp diameter (mm) | - | 8 |
| scaffold length (mm) | - | 35.96 |
| number of rings | - | 16 |
| wall thickness (in) | 235 | 0.011 |
| mid strut width (in) | 261 | 0.0116 |
| inner radii (in) | 262 | 0.00025 |
| outer radii (in) | 263 | 0.01325 |
| link width (in) | 264 | 0.0115 |
| ring height (in) | 265 | 0.0589 |
| strut lenght (in) | 266 | 0.0857 |
| angle (deg) | 267 | 101 |
| angle (deg) | 268 | 105 |
| angle (deg) | 269 | 98 |
| no. of struts per ring | - | 16 |
| number of links connecting ring pairs | - | 4 |

FIG. 6B

CRUSH RECOVERABLE POLYMER SCAFFOLDS

PRIORITY CLAIM

This application is a continuation of application Ser. No. 13/015,488 which was filed on Jan. 27, 2011, which claimed the benefit of U.S. provisional application No. 61/385,891 filed on Sep. 23, 2010, U.S. provisional application No. 61/385,902 filed Sep. 23, 2010 and U.S. provisional application No. 61/299,968 filed on Jan. 30, 2010. application Ser. No. 13/015,488 and provisional applications 61/385,891, 61/385,902 and 61/299,968 are incorporated herein by reference.

FIELD OF THE INVENTION

The present invention relates to drug-eluting medical devices; more particularly, this invention relates to polymeric scaffolds that are expanded by a delivery balloon.

BACKGROUND OF THE INVENTION

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen (one example of a stent is found in U.S. Pat. No. 6,066,167 to Lau et al). Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

The stent must be able to satisfy a number of basic, functional requirements. The stent must be capable of withstanding the structural loads, for example, radial compressive forces, imposed on the stent as it supports the walls of a vessel after deployment. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Even before the radial yield strength is exceeded there may be permanent deformation in the stent in a following radial compressive load, but this degree of permanent deformation somewhere in the stent is not severe enough to have a significant effect on the stent's overall ability to radially support a vessel. Therefore, in some cases the art may view "radial yield strength" as the maximum radial loading, beyond which the scaffold stiffness changes dramatically. "Radial yield strength" units are sometimes force-divided-by-length, which is an expression of radial yield strength on a per-unit-length basis. Thus, for a radial yield strength per unit length, e.g., F N/mm, the radial load which, if it exceeds this value, would result in significant change in stiffness for a stent having two different lengths, L1 and L2, would therefore be the product F*L1 and F*L2, respectively. The value F, however, is the same in both cases, so that a convenient expression can be used to appreciate the radial yield strength independent of the length of the stent. Typically, the radial force that identifies the point where stiffness is lost does not change much on a per-unit-length basis when the stent length changes.

Stents implanted in coronary arteries are primarily subjected to radial loads, typically cyclic in nature, which are due to the periodic contraction and expansion of vessels as blood is pumped to and from a beating heart. Stents implanted in peripheral blood vessels, or blood vessels outside the coronary arteries, e.g., iliac, femoral, popliteal, renal and subclavian arteries, however, must be capable of sustaining both radial forces and crushing or pinching loads. These stent types are implanted in vessels that are closer to the surface of the body. Because these stents are close to the surface of the body, they are particularly vulnerable to crushing or pinching loads, which can partially or completely collapse the stent and thereby block fluid flow in the vessel.

As compared to a coronary stent, which is limited to radial loads, a peripheral stent must take into account the significant differences between pinching or crushing loads and radial loads, as documented in Duerig, Tolomeo, Wholey, *Overview of superelastic stent Design*, Min Invas Ther & Allied Technol 9(3/4), pp. 235-246 (2000) and Stoeckel, Pelton, Duerig, *Self-Expanding Nitinol Stents—Material and Design Considerations*, European Radiology (2003). The corresponding crushing and radial stiffness properties of the stent also can vary dramatically. As such, a stent that possesses a certain degree of radial stiffness does not, generally speaking, also indicate the degree of pinching stiffness possessed by the stent. The two stiffness properties are not the same, or even similar.

The amount of cross-sectional crush expected for a peripheral stent implanted within the femoral artery has been estimated to be about 5.8+/−7%, 6.5+/−4.9% and 5.1+/−6.4% at the top, middle and bottom portions of the femoral artery in older patients and 2.5+/−7.7%, −0.8+/−9.4% and −1.5+/−10.5% for younger patients. Other considerations for peripheral stents are the degree of bending and axial compression the stent can withstand without mechanical loss of strength/stiffness. As compared to coronary stents, a peripheral stent usually has lengths of between about 36 and 40 mm when implanted in the superficial femoral artery, as an example. As such, the stent must be flexible enough to withstand axial compression and bending loading without failure. The amount of bending and axial compression expected has been studied and reported in Nikanorov, Alexander, M. D. et al., *Assessment of self-expanding Nitinol stent deformation after chronic implantation into the superficial femoral artery.*

To date the most commonly used type of peripheral stent are self-expanding stents made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. Complications resulting from COF are discussed in Schwartz, Lewis B. et al. *Does Stent Placement have a learning curve: what mistakes do we as operators have to make and how can they be avoided?*, Abbott Laboratories; Abbott Park, Ill., USA. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF.

Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel. However, the prior art has concluded that plastically deformed stents, once collapsed, pinched or crushed in a peripheral artery will remain so, permanently blocking the vessel. The prior art has concluded, therefore, that plastically deformed stents pose an undesirable condition to the patient and should not be used to treat peripheral blood vessels.

A polymer scaffold, such as that described in US 2010/0004735 is made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. The polymer scaffold described in US 2010/0004735, as opposed to a metal stent, is intended to remain in the body for only a limited period of time. The scaffold is made from a biodegradable or bioerodable polymer. In many treatment applications, the presence of a stent in a body may be necessary for a limited period of time until its intended function of, for example, maintaining vascular patency and/or drug delivery is accomplished. Moreover, it is believed that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a polymer scaffold.

The art recognizes a variety of factors that affect a polymeric scaffold's ability to retain its structural integrity and/or shape when subjected to external loadings, such as crimping and balloon expansion forces. These interactions are complex and the mechanisms of action not fully understood. According to the art, characteristics differentiating a polymeric, bio-absorbable scaffold of the type expanded to a deployed state by plastic deformation from a similarly functioning metal scaffold are many and significant. Indeed, several of the accepted analytic or empirical methods/models used to predict the behavior of metallic scaffolds tend to be unreliable, if not inappropriate, as methods/models for reliably and consistently predicting the highly non-linear, time dependent behavior of a polymeric load-bearing structure of a balloon-expandable scaffold. The models are not generally capable of providing an acceptable degree of certainty required for purposes of implanting the scaffold within a body, or predicting/anticipating the empirical data.

Moreover, it is recognized that the state of the art in medical device-related balloon fabrication, e.g., non-compliant balloons for scaffold deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed polymeric scaffold. One difference, for example, is the propensity for fracture or cracks to develop in a polymer scaffold. The art recognizes the mechanical problem as too different to provide helpful insights, therefore, despite a shared similarity in class of material. At best, the balloon fabrication art provides only general guidance for one seeking to improve characteristics of a balloon-expanded, bio-absorbable polymeric scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bio-absorbable polymer such as PLLA or PLGA.

Processing steps performed on, and design changes made to a metal stent that have not typically raised concerns for, or required careful attention to unanticipated changes in the average mechanical properties of the material, therefore, may not also apply to a polymer scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping? As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different polymeric scaffold designs for improvement thereof, there are far less inferences, theories, or systematic methods of discovery available, as a tool for steering one clear of unproductive paths, and towards more productive paths for improvement, than when making changes in a metal stent.

The present inventors recognize, therefore, that, whereas inferences previously accepted in the art for stent validation or feasibility when an isotropic and ductile metallic material was used, those inferences would be inappropriate for a polymeric scaffold. A change in a polymeric scaffold pattern may affect not only the stiffness or lumen coverage of the scaffold in its deployed state supporting a lumen, but also the propensity for fractures to develop when the scaffold is crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a polymeric scaffold that is plastically deformed, both when crimped to, and when later deployed by a balloon, unfortunately, is not predictable to the same or similar degree as for a metal stent. Indeed, it is recognized that unexpected problems may arise in polymer scaffold fabrication steps as a result of a changed pattern that would not have necessitated any changes if the pattern was instead formed from a metal tube. In contrast to changes in a metallic stent pattern, a change in polymer scaffold pattern may necessitate other modifications in fabrication steps or post-fabrication processing, such as crimping and sterilization.

In addition to meeting the requirements described above, it is desirable for a scaffold to be radiopaque, or fluoroscopically visible under x-rays. Accurate placement is facilitated by real time visualization of the delivery of a scaffold. A cardiologist or interventional radiologist can track the delivery catheter through the patient's vasculature and precisely place the scaffold at the site of a lesion. This is typically accomplished by fluoroscopy or similar x-ray visualization procedures. For a scaffold to be fluoroscopically visible it must be more absorptive of x-rays than the surrounding tissue. Radiopaque materials in a scaffold may allow for its direct visualization. However, a significant shortcoming of a biodegradable polymer scaffold (and polymers generally composed of carbon, hydrogen, oxygen, and nitrogen) is that they are radiolucent with no radiopacity. Biodegradable polymers tend to have x-ray absorption similar to body tissue. One way of addressing this problem is to attach radiopaque markers to structural elements of the stent. A radiopaque marker can be disposed within a structural element in such a way that the marker is secured to the structural element. However, the use of stent markers on polymeric stents entails a number of challenges. One challenge relates to the difficulty of insertion of markers. These and related difficulties are discussed in US 2007/0156230.

There is a need to develop a prosthesis for treating peripheral blood vessels that possesses the desirable qualities of a balloon expanded stent, which does not exert residual outward forces on the vessel (as in the case of a self-expanding stent) while, at the same time, being sufficiently resilient to recover from a pinching or crushing load in a peripheral blood vessel, in addition to the other loading events expected within a peripheral blood vessel that are not typically experienced by a coronary scaffold. There is also a need to fabricate such a polymer scaffold so that the prosthesis also is capable of possessing at least a minimum radial strength and stiffness required to support a peripheral blood vessel; a low crossing profile; and a limited presence in the blood vessel. There is also a need for a scaffold that is easily monitored during its pendency using standard imaging techniques, and is capable of high yield production.

SUMMARY OF THE INVENTION

The invention provides a polymer scaffold suited to address the foregoing needs including high crush recoverability, e.g., at least about 90-95% after a 50% crushing load. The scaffold is cut from a polymer tube and crimped to a balloon. Accordingly, the invention provides a balloon expandable, plastically deformed scaffold cut from a tube and being suitable for use as a peripheral scaffold. As such, the drawbacks of self-expanding stents can be obviated by practicing the invention.

To date the art has relied on metals or alloys for support and treatment of peripheral blood vessels. As mentioned earlier, once a metallic stent is implanted it remains in the body permanently, which is not desired. A scaffold made from a material that dissolves after it treats an occluded vessel, therefore, would be preferred over a metal stent. A polymer, however, is much softer than a metal. If it will serve as a replacement to metal, a new design approach is needed.

High radial force, small crimped profile and crush recovery is needed in the polymer scaffold. If the material cannot be modified enough to meet these needs, then a modification to the design of the scaffold network of struts is required. There are a few known approaches to increase the radial yield strength. One is to increase the wall thickness and another is to increase the strut width. Both of these modifications, however, will result in greater profile of the device at the crimped state. A small crimped profile of the device and increased stiffness and strength is therefore necessary and heretofore not addressed in the art.

As will be appreciated, aspects of a polymer scaffold disclosed herein contradict conclusions that have been previously made in the art concerning the suitability of a balloon-expandable stent, or scaffold for use in peripheral blood vessels. The problems concerning self-expanding stents are known. Therefore a replacement is sought. However, the conventional wisdom is that a balloon expanded stent having sufficient radial strength and stiffness, as opposed to a self-expanding stent, is not a suitable replacement, especially in vessels that will impose high bending and/or crushing forces on the implanted prosthesis.

According to the invention, crush-recoverable polymer scaffolds possessing a desired radial stiffness and strength, fracture toughness and capability of being crimped down to a target delivery diameter will properly balance three competing design attributes: radial strength/stiffness verses toughness, in-vivo performance verses compactness for delivery to a vessel site, and crush recovery verses radial strength/stiffness.

Disclosed herein are embodiments of a scaffold that can effectively balance these competing needs, thereby providing an alternative to prostheses that suffer from chronic outward force. As will be appreciated from the disclosure, various polymer scaffold combinations were fabricated and tested in order to better understand the characteristics of a scaffold that might address at least the following needs:

Crush recoverability of the scaffold without sacrificing a desired minimal radial stiffness and strength, recoil, deployability and crimping profile;

Acute recoil at deployment—the amount of diameter reduction within ½ hour of deployment by the balloon;

Delivery/deployed profile—i.e., the amount the scaffold could be reduced in size during crimping while maintaining structural integrity;

In vitro radial yield strength and radial stiffness;

Crack formation/propagation/fracture when crimped and expanded by the balloon, or when implanted within a vessel and subjected to a combination of bending, axial crush and radial compressive loads;

Uniformity of deployment of scaffold rings when expanded by the balloon; and

Pinching/crushing stiffness.

Based on these studies, which have included in-vivo animal testing of a peripherally implanted scaffold, the invention provides the following relationships characterizing a polymer scaffold that exhibits the desired characteristics including crush recoverability:

a ratio of outer diameter to wall thickness;

a ratio of outer diameter to strut width;

a ratio of radial stiffness to pinching stiffness;

a ratio of pinching stiffness to scaffold diameter;

a ratio of radial stiffness to scaffold diameter;

a ratio of strut or link thickness to its width; and a ratio of pre-crimp scaffold diameter to strut moment of inertia.

Additional relationships characterizing mechanical properties of a scaffold meeting the above needs may be inferred from the disclosure.

According to one aspect of the invention, polymer scaffolds having crush recovery and good radial strength and stiffness possess one or more of the following relations between material properties and/or scaffold dimensions. It will be understand that these relationships, as disclosed herein and throughout the disclosure, include previously unknown relationships among scaffold structural properties, material and dimensions that reveal key characteristics of a scaffold needed for a crush-recoverable scaffold uniquely suited to achieve the clinical objective. As such, the invention includes the identification of a particular relationship, e.g., a dimensionless number used in combination with one or more additional scaffold dimensions, e.g., inflated diameter, aspect ratio, crown angle, wall thickness, to produce a crush-recoverable scaffold having the desired stiffness and strength property needed to support the vessel.

According to one aspect of the invention a strut forming a ring of the crush recoverable scaffold has an aspect ratio (AR) of between about 0.8 and 1.4. Aspect ratio (AR) is defined as the ratio of cross-sectional width to thickness. Thus for a strut having a width of 0.0116 and a wall thickness of 0.011 the AR is 1.05.

According to another aspect of the invention, the links connect rings of the scaffold. The AR of a link may be between about 0.4 and 0.9.

According to another aspect of the invention, the AR of both the link and the strut may between about 0.9 and 1.1, or about 1.

According to another aspect of the invention, a crush recoverable scaffold is crimped to a delivery balloon of a balloon catheter. The balloon has a maximum expanded diameter less than the diameter of the scaffold before crimping. The scaffold has a pre-crimping diameter of between 7-10 mm, or more narrowly 7-8 mm, and possesses a desired pinching stiffness while retaining at least a 80% recoverability from a 50% crush.

According to another aspect of the invention a crush-recoverable scaffold has a desirable pinching stiffness of at least 0.5 N/mm, radial strength of at least 0.3 N/mm and a wall thickness of at least 0.008", or between about 0.008" and 0.012". The scaffold is capable of recovering at least 80% of its diameter after at least an about 30% crush.

According to another aspect of invention a 9 mm scaffold (pre-crimp diameter) with wall thickness of between 0.008" and 0.014", or more narrowly 0.008" and 0.011" providing the desired pinching stiffness while retaining 50% crush recoverability. More generally, it was found that a ratio of pre-crimp or tube diameter to wall thickness of between about 30 and 60, or between about 20 and 45 provided 50% crush recoverability while exhibiting a satisfactory pinching stiffness and radial stiffness. And in some embodiments it was found that a ratio of inflated diameter to wall thickness of between about 25 and 50, or between about 20 and 35.

According to another aspect of the disclosure a crush-recoverable scaffold has a desirable pinching stiffness to wall thickness ratio of 0.6-1.8 N/mm².

According to another aspect of the disclosure a crush-recoverable scaffold has a desirable pinching stiffness to wall thickness*tube diameter ratio of 0.08-0.18 N/mm³.

According to another aspect of invention a crush-recoverable scaffold has a ratios of pinching stiffness to radial stiffness of between about 4 to 1, 3 to 1, or more narrowly about 2 to 1; ratios of pinching stiffness to wall thickness of between about 10 to 70, or more narrowly 20 to 50, or still more narrowly between about 25 and 50; and ratios of scaffold inflated diameter to pinching stiffness of between about 15 and 60 or more narrowly between about 20 to 40.

According to another aspect of the invention a crush recoverable polymer scaffold has rings comprising 9 or 8 crowns. For a 9 crown pattern and 7-9 mm outer diameter a crown angle is less than 115 degrees and more preferably crown angles between 105 and 95 degrees. For a 8 crown pattern and 7-9 mm outer diameter the angle is about less than 110 degrees.

According to another aspect of invention, a crush-recoverable scaffold has a radial strength of greater than about 0.3 N/mm, or between about 0.32 and 0.68 N/mm, and a radial stiffness of greater than about 0.5 N/mm or between about 0.54 N/mm and 1.2 N/mm. The scaffold may have a wall thickness of about 0.008" to 0.014" and configured for being deployed by a 6.5 mm non-compliant balloon from about a 2 mm crimped profile, or deployed to a diameter of between about 6.5 mm and 7 mm from about a 2 mm crossing profile on a balloon catheter. The scaffold strut and/or link elements may have an AR of equal to or greater than 1.0.

According to another aspect of the invention, a crush-recoverable polymer scaffold recovers greater than 80% of its diameter after being pinched to 50% of its diameter and the pinched state is maintained for 1-5 minutes.

According to another aspect of the invention, a crush-recoverable polymer scaffold recovers greater than 90% of its diameter after being pinched to 25% of its diameter and the pinched state is maintained for 1-5 minutes.

According to another aspect of the invention, a crush-recoverable polymer scaffold includes a marker structure including a pair of markers arranged circumferentially on a connecting link and spaced from adjacent rings of the scaffold so that the crimped profile is the same with or without the markers. Alternatively, according to another aspect of the invention, a radiopaque foil is wrapped around a link of the scaffold and held in place In another aspect of invention, a polymer scaffold having a wall thickness of between about 0.008" and 0.014" and outer diameter of between about 7 mm and 10 mm was capable of meeting the foregoing needs.

In another aspect of the invention, a crush recoverable scaffold was crimped from a 7 mm, 8 mm and 9 mm outer diameter to a 2 mm outer diameter and deployed without fracture and/or excessive cracking of struts that are a typical concern when a polymer, especially a brittle polymer like PLLA, is used to form the scaffold structure.

A scaffold has a pre-crimp diameter ($SD_{PC}$) meaning the diameter of the scaffold before it is crimped to its delivery balloon, and an inflated diameter ($SD_I$). The scaffold is crimped to the balloon-catheter and intended for delivery to a vessel within the body. The average vessel diameter where the scaffold is to be implanted is VD. $SD_I$ is about 1.2 times greater than VD. For purposes of the disclosure, VD can range from about 5 mm to 10 mm and $SD_{PC}$ can range between about 6 to 12 mm. According to another aspect of invention:

$$1.1 \times (VD) \leq SD_{PC} \leq 1.7 \times (VD) \quad (EQ. 1)$$

$$1.1 \times (SD_I) \times (1.2)^{-1} \leq SD_{PC} \leq 1.7 \times (SD_I) \times (1.2)^{-1} \quad (EQ. 2)$$

Scaffold satisfying EQS. 1 and 2 can yield a crush-recoverable scaffold having at least 90% recovery after at least a 25% crush, while also having favorable radial stiffness, pinching stiffness, acceptable recoil, radial strength and/or crossing profile. In a preferred embodiment the scaffold is made from PLLA. The partial inequalities in EQS. 1 and 2 are intended to refer to approximate ranges.

It is contemplated that a polymer scaffold according to the invention may be used to treat conditions in the Femoral artery, Popliteal artery, Tibial artery, Pudendal artery, Brachial artery, Caroitid artery, Jugular vein, Abdominal arteries and veins.

In another aspect of the invention a symmetric, closed cell for a scaffold improves deployment uniformity and reduces fracture problems for a scaffold having crush recoverability.

In another aspect of invention a balloon-expandable medical device for being implanted in a peripheral vessel of the body includes a scaffold formed from a polymer tube,— configured for being crimped to a balloon,—the scaffold having a pattern of interconnected elements and—the scaffold having an expanded diameter when expanded from a crimped state by the balloon, wherein the scaffold attains greater than about 90% of its diameter after being crushed to at least 33% of its expanded diameter; and wherein the scaffold has a radial stiffness greater than 0.3 N/mm.

In another aspect of invention a balloon-expandable medical device for being implanted in a peripheral vessel of the body includes a crimped scaffold that when deployed by a balloon forms a scaffold having an expanded diameter; wherein the scaffold is capable of regaining more than 90% of its diameter after being crushed to at least 75% of its expanded diameter; and wherein the scaffold comprises—a radial stiffness greater than about 0.3 N/mm, and—a radial strength, pinching strength, pinching stiffness and fracture toughness of a pre-crimp scaffold having a pre-crimp diameter between 300-400% greater than a diameter of the crimped scaffold.

In another aspect of invention a radially expandable stent includes a balloon expandable scaffold formed from a PLLA tube,—the scaffold including a plurality of radially expandable undulating cylindrical rings of struts, wherein the undulating rings of struts comprise crowns, wherein adjacent rings of struts are connected by longitudinal links, wherein a ring has no more than 9 crowns and 3 links around its circumference, and the angle at any crown is less than 115 degrees;—the scaffold has an outer diameter of 8 to 10 mm; and—the scaffold has a wall thickness at least about 0.008".

In another aspect of invention a peripherally implantable medical device includes a crimped scaffold that when expanded by a balloon forms a scaffold having a diameter;— the scaffold regains more than 90% of the diameter after being crushed to at least 67% of the diameter,—the scaffold is formed from PLLA,—the scaffold has a diameter to wall thickness ratio of between about 30 and 60;—the scaffold has struts and links, wherein a strut and/or link has a width to thickness ratio of between about 0.8 and 1.4, and—the scaffold has a radial stiffness greater than or equal to about 0.3 N/mm.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIGS. 6A and 6B are tables showing examples of scaffold features in accordance with aspects of the disclosure.

FIG. 9A shows the expanded configuration and FIG. 9B shows the location of the radiopaque markers relative to folded struts of the scaffold rings in the crimped configuration.

FIG. 10A shows the expanded configuration and FIG. 10B shows the location of the radiopaque marker relative to folded struts of the scaffold rings in the crimped configuration.

FIGS. 11A, 11B and 11E depict examples of locations for a cylindrical marker while FIGS. 11C and 11D depict locations for a strip of marker material.

FIG. 12A shows a cross-section of a scaffold in its un-deformed (unloaded) state and deformed state when subjected to a pinching load (drawn in phantom). FIGS. 12B-12C are models of equivalent half-cylinder shells of different thickness to show the effects of wall thickness on crush-recoverability when a scaffold is subject a pinching load.

FIG. 14D shows an asymmetric weakened link portion and FIG. 14F shows a symmetric weakened link portion.

DETAILED DESCRIPTION OF EMBODIMENTS

Figure 1:
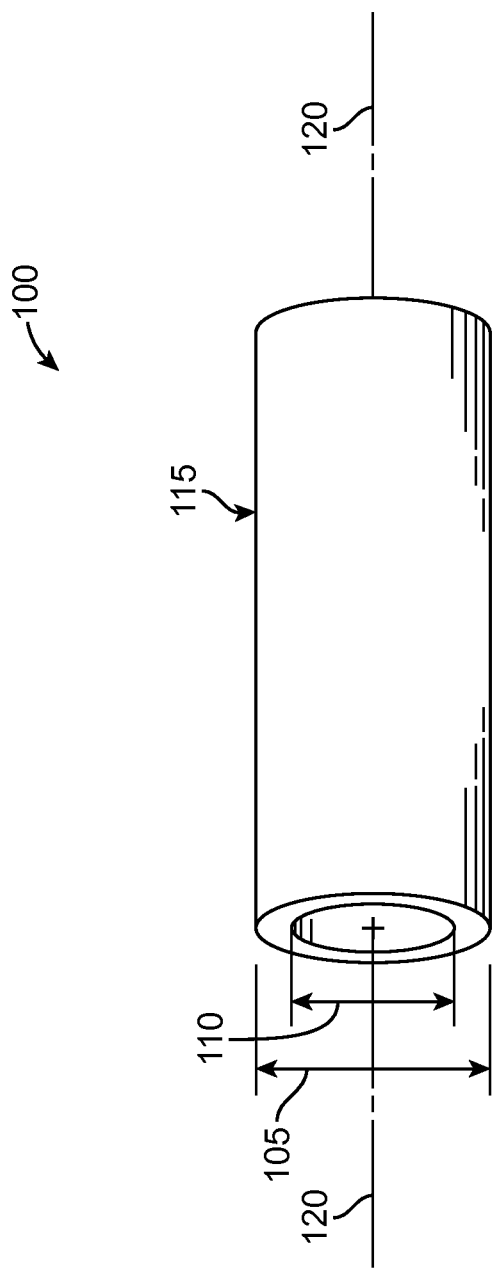
FIG. 1 is a perspective view of a deformed polymer tube. The tube is formed into a scaffold.

The disclosure proceeds as follows. First, definitions of terms that may be used during the course of the subsequent disclosure are explained. Embodiments of processes for forming a deformed polymer tube from a precursor are provided. According to the disclosure, the crush recoverable and balloon expandable scaffold is cut from a tube (FIG. 1) formed through a process intended to enhance mechanical properties of the scaffold including fracture toughness. Discussion of the scaffold patterns according to several embodiments are discussed next. Examples of the scaffold patterns are provided. During this discussion, reference is made to aspects of a scaffold found to play an important role in the stiffness, strength, crimping and deployment of a polymer scaffold, as well as other properties as they relate to crush recoverability of a load-bearing polymer structure. Included herein are aspects of the scaffold that are contrary and, in some cases, surprising and unexpected, particularly when compared to aspects of a comparable, peripheral metal stent having a similar pattern of struts. Finally, bench and in-vivo test results are discussed, including exemplary examples of embodiments of invention and explanation of the results observed and problems overcome. In these examples there may be gained a further appreciation of aspects of invention—a crush recoverable and balloon-expandable polymer scaffold having desirable radial strength and stiffness properties and capable of being crimped to a diameter suitable for delivery through a blood vessel via a balloon catheter.

For purposes of this disclosure, the following terms and definitions apply:

"Inflated diameter" or "expanded diameter" refers to the maximum diameter the scaffold attains when its supporting balloon is inflated to expand the scaffold from its crimped configuration to implant the scaffold within a vessel. The inflated diameter may refer to a post-dilation diameter which is beyond the nominal balloon diameter, e.g., a 6.5 mm semi-compliant PEBAX balloon has about a 7.4 mm post-dilation diameter. The scaffold diameter, after attaining its inflated diameter by balloon pressure, will to some degree decrease in diameter due to recoil effects and/or compressive forces imposed by the wall of the vessel after the balloon is removed. For instance, referring to an expansion of the V59 scaffold having the properties in Table 6B, when placed on a 6.5 mm PEBAX balloon and the balloon is expanded to a post-dilation condition outside a vessel, the scaffold inner diameter will be about 7.4 mm and about (0.955)×(7.4 mm) before and after, respectively, acute-recoil has occurred. The inflated diameter may be about 1.2 times the average vessel diameter and peripheral vessel sizes typically range from about 4 to 10 mm for purposes of this disclosure.

"Theoretical minimum diameter" means the smallest diameter for a scaffold based on its geometry of strut lengths, thickness and widths. A "theoretical minimum diameter" is not defined in terms of a minimum crimped profile for a scaffold or stent that can be later deployed and work properly as a balloon-expanded prosthesis. Rather, it is only a definition defined by the geometry, or minimum volume of space that a device can occupy following a uniform reduction in diameter. As a formula, the "theoretical minimum diameter" (Dmin) may be expressed as follows:

$$Dmin = (\Sigma Swi + \Sigma Crj + \Sigma Lwk)*(1/\pi) + 2*WT \quad (EQ. 3)$$

Where the quantities above are taken from a cross-sectional slice of the scaffold, $\Sigma$ Swi (i=1 . . . n) is the sum of n ring struts having width Swi;

$\Sigma$ Crj (j=1 . . . m) is the sum of m crown inner radii having radii Crj (times 2);

$\Sigma$ Lwk (k=1 . . . p) is the sum of p links having width Lwk; and

WT is the scaffold wall thickness.

Figure 7A:
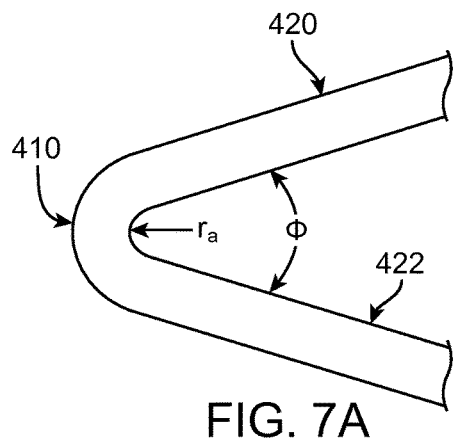
FIG. 7A-7B shows a scaffold crown formation in its expanded and crimped states.

EQ. 3 assumes the width for a folded pair of struts, e.g., struts 420, 422 in FIG. 7A, is the same whether measured near the crown 410 or the strut mid width. When the crown is built up more, so that the width is wider there than ring strut mid-width, Swi would be measured by the width at the crown. Also, the minimum space between struts is defined by twice the inner radius of the adjacent crown (or valley), i.e., Crj.

For the scaffold dimensions of FIG. 6B the crown width is wider than the strut mid-width. Therefore, using EQ. 3 Dmin is $[16*(0.013)+12*(0.0005)+4*(0115)]*(1/\pi)+2*(0.011)=0.1048"$ or 2.662 mm (minimum diameter computed at cross-section passing through crowns). If, instead the cross-section were taken at the strut mid width (0.0116 instead of 0.013) EQ. 3 gives 0.0976" or 2.479 mm.

It should be noted that EQ.3 assumes the struts have essentially a square cross-section. This is the case for the scaffold of FIG. 6B (strut cross-sectional dimension at the crown is 0.011×0.013). For a scaffold having struts with a trapezoidal cross section, e.g., a scaffold cut from a smaller diameter so that the ratio of wall thickness to outer diameter is much higher than in the case of FIG. 1, a more accurate approximation for Dmin would be $(\Sigma Swi+\Sigma Crj+\Sigma Lwk)*(1/\pi)$ since the edges of the struts at the outer surface would abut at Dmin before the surfaces extending over the thickness of a strut abut each other.

The glass transition temperature (referred to herein as "Tg") is the temperature at which the amorphous domains of a polymer change from a brittle vitreous state to a solid deformable or ductile state at atmospheric pressure. In other words, Tg corresponds to the temperature where the onset of segmental motion in the chains of the polymer occurs. Tg of a given polymer can be dependent on the heating rate and can be influenced by the thermal history of the polymer. Furthermore, the chemical structure of the polymer heavily influences the glass transition by affecting mobility of polymer chains.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e radial strength.

The term "crush recovery" is used to describe how the scaffold recovers from a pinch or crush load, while the term "crush resistance" is used to describe the force required to cause a permanent deformation of a scaffold. A scaffold or stent that does not possess good crush recovery does not substantially return to its original diameter following removal of a crushing force. As noted earlier, a scaffold or stent having a desired radial force can have an unacceptable crush recovery. And a scaffold or stent having a desired crush recovery can have an unacceptable radial force.

Figure 2:
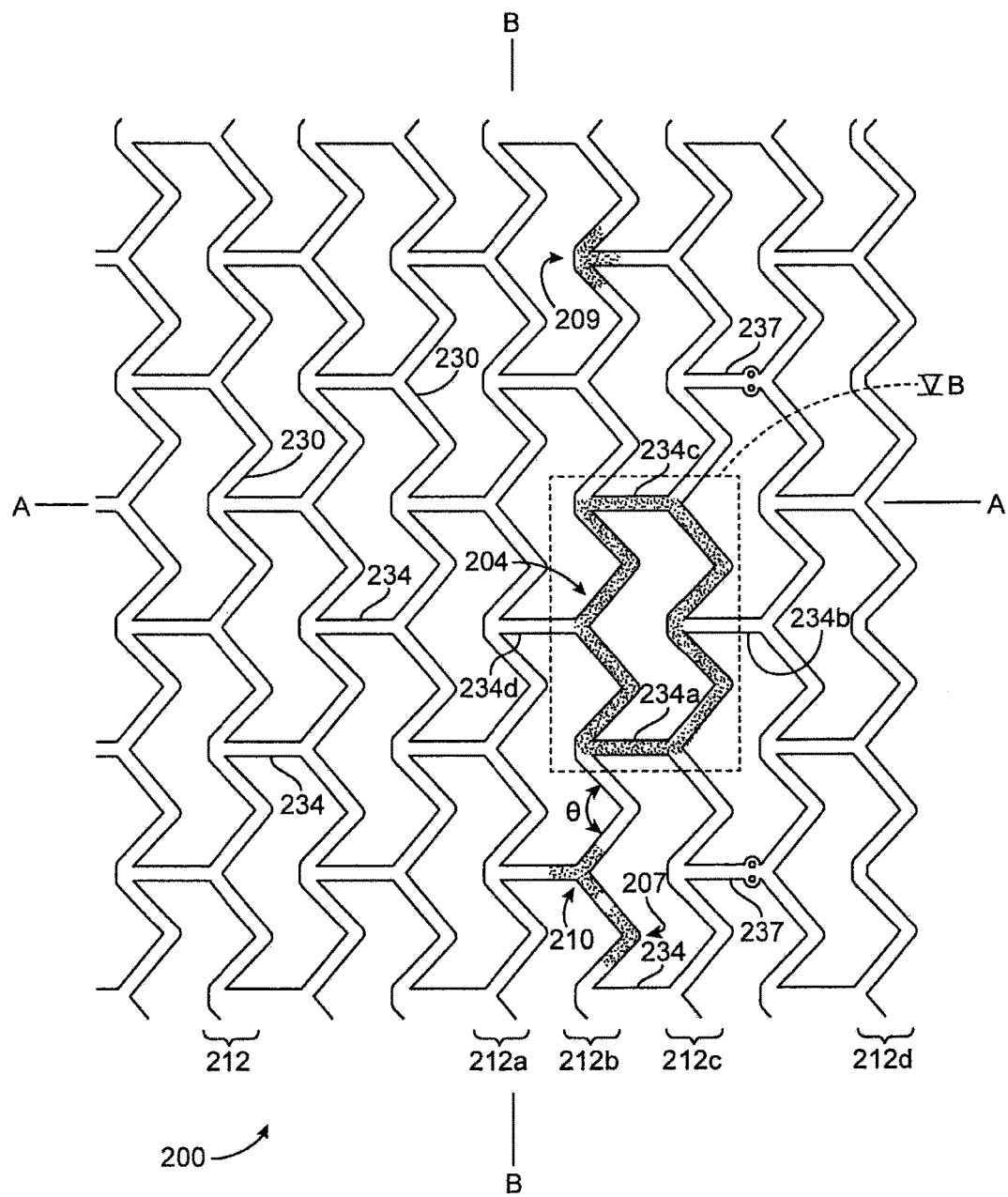
FIG. 2 is a partial planar view of a scaffold pattern according to a first embodiment of a scaffold.

The polymer scaffold illustrated in FIG. 2 is formed from a poly(L-lactide) ("PLLA") tube. The process for forming this PLLA tube may be the process described in U.S. patent application Ser. No. 12/558,105. Reference is made to a precursor that is "deformed" in order to produce the tube of FIG. 1 having the desired scaffold diameter, thickness and material properties as set forth below. Before the tube is deformed or, in some embodiments, expanded to produce the desired properties in the starting tube for the scaffold, the precursor is formed. The precursor may be formed by an extrusion process which starts with raw PLLA resin material heated above the melt temperature of the polymer which is then extruded through a die. Then, in one example, an expansion process for forming an expanded PLLA tube includes heating a PLLA precursor above the PLLA glass transition temperature (i.e., 60-70 degrees C.) but below the melt temperature (165-175 degrees C.), e.g., around 110-120 degrees C.

A precursor tube is deformed in radial and axial directions by a blow molding process wherein deformation occurs progressively at a predetermined longitudinal speed along the longitudinal axis of the tube. As explained below, the deformation improves the mechanical properties of the tube before it is formed into the scaffold of FIG. 2. The tube deformation process is intended to orient polymer chains in radial and/or biaxial directions. The orientation or deformation causing re-alignment is performed according to a precise selection of processing parameters, e.g. pressure, heat (i.e., temperature), deformation rate, to affect material crystallinity and type of crystalline formation during the deformation process.

In an alternative embodiment the tube may be made of poly(L-lactide-co-glycolide), poly(D-lactide-co-glycolide) ("PLGA"), polycaprolactone ("PCL"), any semi-crystalline copolymers combining any of these monomers, or any blends of these polymers. Material choices for the scaffold should take into consideration the complex loading environment associated with many peripheral vessel locations, particularly those located close to limbs.

The femoral artery provides a dynamic environment for vascular implants as various forces may crush, twist, extend, or shorten the device simultaneously. The force application may vary between point load to distributed load or a combination thereof and also as a function of time. Recent results have shown that bioresorbable scaffolds made from highly crystalline PLLA can provide crush recovery without causing a permanent and constant outward radial force on the vessel. The permanent and constant outward radial force may be the cause of late clinical issues with nitinol self-expandable stents. However, a remaining challenge with bioresorbable scaffolds is to make them optimally fracture resistant as a function of time; that is, to improve their fatigue life or survivability under a variety of dynamic loading environments. There is a continuing need to improve fracture toughness for a scaffold; and in particular a peripherally implanted scaffold.

The fracture resistance of a vascular scaffold depends not only on the design and the material, but is also the manufacturing process and deployment parameters. Therefore it is in particular necessary to have a process, design, and a delivery system that allows the scaffold to be uniformly expanded and deployed. As a consequence of non-uniform deployment the various struts and crowns of a scaffold will potentially be exposed to very different forces and motions, which has a deleterious effect on the fatigue life.

An useful dimensionless number useful for characterizing a material's fracture toughness is called a Deborah number (Ratio of intrinsic material damping time constant and time constant of external applied force). The higher the Deborah number, the greater is the expected potential of an implant to fracture under a transient load or fatigue load of a given amplitude.

Toughening domains can be introduced into an implant design in several ways: a) backbone alteration to include low Tg blocks, e.g. block copolymers, b) polymer blends and c) introducing light crosslinks into the backbone.

Fracture toughness of a homopolymer such as PLLA can also be improved by controlling the microstructure of the final implant. Variables such as % crystallinity, size and/or distribution of crystallites, spatial distribution, and gradient and shape of the crystalline domains. A combination of these micro-structural controls in combination with a macroscopic design, e.g., scaffold pattern, crimping process, etc. may improve fracture toughness without significant adverse affects on other scaffold material properties, e.g., radial and/or pinching stiffness.

An alternative to providing elastomeric properties is the use of a multilayered structure having "soft" and "hard" layers, where the soft layer/layers would be made from a low Tg material and the hard layers would have a high Tg material. In a similar way high and low Tg domains can generate typical rubber-toughened morphologies through the use of block copolymers or polymer blends. The Tg of a given domain/block could be generated from a given monomer or by the use of several monomers in a random co-polymer. Typical low Tg materials can be made from caprolactone, lactone derivatives, carbonate, butylsuccinate, trimethylene carbonate, dioxanone or other known monomers in accordance with the disclosure. Other low Tg materials that could be used, would be a material that clears the kidneys through dissolution rather than degradation. Such material may include polyethylene glycol (PEG), polyvinylpyrrolidone (PVP), or polyvinylalochol (PVA), or other known polymers in accordance with the disclosure.

Alternative ways to improve the fatigue properties are through introduction of axial flexibility and the use of pre-designed fracture points, in particular in the connector links. The fracture points could function as precursors of actual fractures, e.g., crazes and cracks or small dimension of fracture distributed in the implant. A distribution or pattern of cracks or crazes may dictate or inform one of an expected toughness of the scaffold when subjected to a particular loading, e.g., torsion, radial force, tensile etc. Although it is understood that, due to the generally highly non-linear relationship between crack formation and a coupled loading environment, that is, simultaneously applied and time varying bending, torsion and axial loading, such predictive methods may not be applicable to all situations.

Alternative ways to improve the fatigue properties are through introduction of axial flexibility and the use of pre-designed fracture points, in particular, fracture points in or near connector links as discussed in greater detail below.

For a tube of FIG. 1 having a diameter about 7 mm and a wall thickness above 200 micro-meters and more specifically a diameter of 8 mm and a wall thickness of 280 micro-meters, the temperature at expansion is 235+/−5 degrees Fahrenheit, the expansion pressure is 110+/−10 psi and the expansion speed is 0.68+/−0.20 mm/sec.

The degree of radial expansion that the polymer tube undergoes can partially characterize the degree of induced circumferential molecular and crystal orientation as well as strength in a circumferential direction. The degree of radial expansion is quantified by a radial expansion ("RE") ratio, defined as RE Ratio=(Inside Diameter of Expanded Tube)/(Original Inside Diameter of the tube). The RE ratio can also be expressed as a percentage, defined as RE %=(RE ratio−1).times.100%. The degree of axial extension that the polymer tube undergoes can partially characterize induced axial molecular or crystal orientation as well as strength in an axial direction. The degree of axial extension is quantified by an axial extension ("AE") ratio, defined as AE Ratio=(Length of Extended Tube)/(Original Length of the Tube). The AE ratio can also be expressed as a percentage, defined as AE %=(AE ratio−1).times.100%. In a preferred embodiment the RE is about 400% and the AE is 40-50%.

Figure 3:
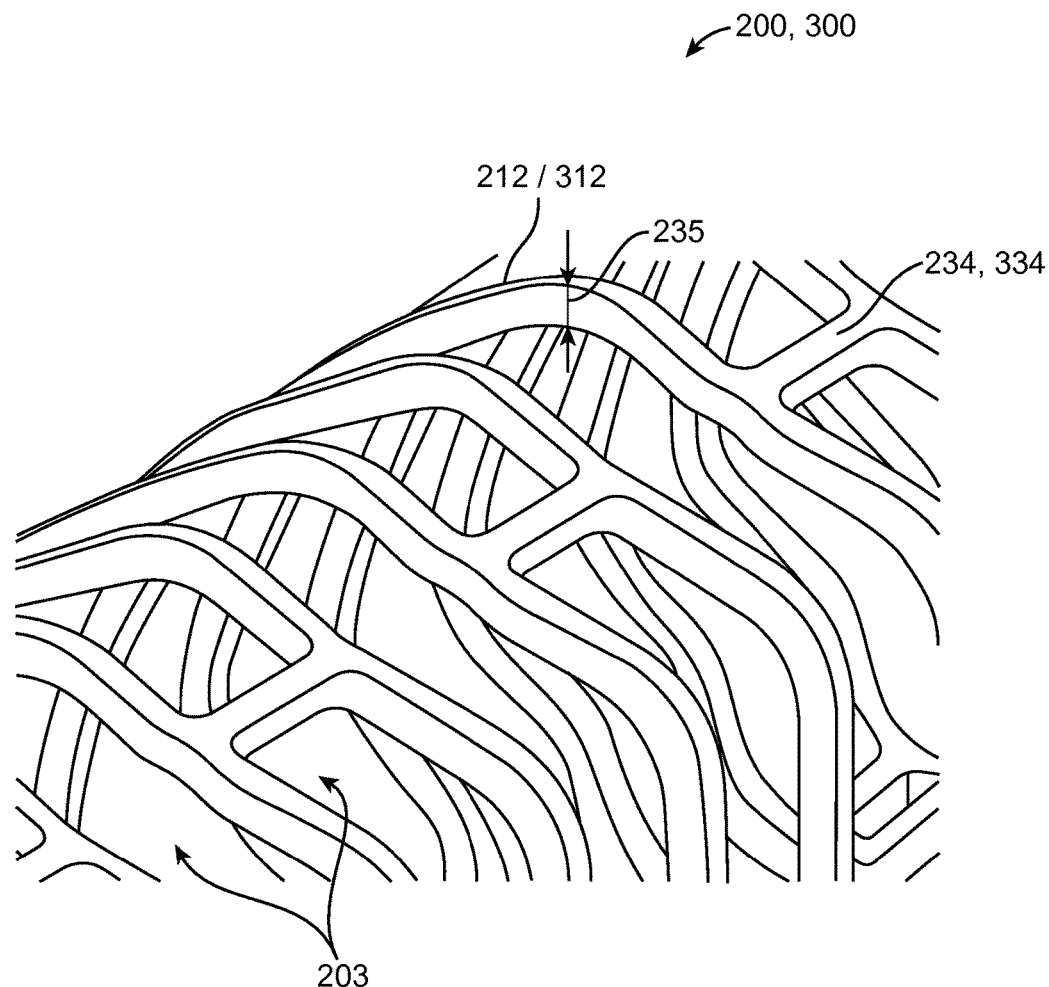
FIG. 3 is a partial perspective view of a scaffold structure.

The strengthened and toughened cylindrical, polymer tube of FIG. 1 is formed into a scaffold structure, in one embodiment a structure having a plurality of struts 230 and links 234 forming a pattern 200 as shown in FIG. 2 (pattern 200 is illustrated in a planar or flattened view), which is about the pattern for the scaffold before crimping and after the scaffold is plastically, or irreversibly deformed from its crimped state to its deployed state within a vessel by balloon expansion. The pattern 200 of FIG. 2, therefore, represents a tubular scaffold structure (as partially shown in three dimensional space in FIG. 3), so that an axis A-A is parallel to the central or longitudinal axis of the scaffold. FIG. 3 shows the scaffold in a state prior to crimping or after deployment. As can be seen from FIG. 3, the scaffold comprises an open framework of struts and links that define a generally tubular body. The cylindrical, deformed tube of FIG. 1 may be formed into this open framework of struts and links described in FIGS. 2-3 by a laser cutting device, preferably, a pico-second green light laser that uses Helium gas as a coolant during cutting.

Details of a suitable laser process can be found in U.S. application Ser. No. 12/797,950. The Helium gas is necessary to avoid melting or altering properties of the scaffold structure adjacent the laser's cutting path. Exemplary laser machining parameters are provided in Table 1.

TABLE 1

Laser Machining Parameters for a crush recoverable polymer scaffold having a wall thickness of between about .008" and .014"

| Parameter | Range |
|---|---|
| Scaffold length (mm) | 8-200 |
| No. of passes to cut | 2-4 |
| Cutting speed (in/min) | 4-10 |
| Fast jog speed (in/min) | 10-14 |
| Max accel/decal (in/min$^2$) | 0-6 |
| Tube outer diameter | 6-12 |
| Laser spot size | 14-20 |
| Laser rep rate (kHz) | 25-50 |
| Laser power setting (W) | .8-1.22 |
| Helium gas flow (scfh) | 11-17 |

Referring to FIG. 2, the pattern 200 includes longitudinally-spaced rings 212 formed by struts 230. A ring 212 is connected to an adjacent ring by several links 234, each of which extends parallel to axis A-A. In this first embodiment of a scaffold pattern (pattern 200) four links 234 connect the interior ring 212, which refers to a ring having a ring to its left and right in FIG. 2, to each of the two adjacent rings. Thus, ring 212b is connected by four links 234 to ring 212c and four links 234 to ring 212a. Ring 212d is an end ring connected to only the ring to its left in FIG. 2.

A ring 212 is formed by struts 230 connected at crowns 207, 209 and 210. A link 234 is joined with struts 230 at a crown 209 (W-crown) and at a crown 210 (Y-crown). A crown 207 (free-crown) does not have a link 234 connected to it. Preferably the struts 230 extend from a crown 207, 209 and 210 at a constant angle from the crown center, i.e., the rings 212 are approximately zig-zag in shape, as opposed to sinusoidal for pattern 200, although in other embodiments a ring having curved struts is contemplated. As such, in this embodiment a ring 212 height, which is the longitudinal distance between adjacent crowns 207 and 209/210 may be derived from the lengths of the two struts 230 connecting at the crown and a crown angle e. In some embodiments the angle e at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 2). The struts 212 centroidal axes lie primarily at about the same radial distance from the scaffold's longitudinal axis. Ideally, substantially all relative movement among struts forming rings also occurs axially, but not radially, during crimping and deployment. Although, as explained in greater detail, below, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the axially and radially expanded tube from which the scaffold is cut) is always greater than a maximum expanded scaffold diameter that the delivery balloon can, or is capable of producing when inflated. According to one embodiment, a pre-crimp diameter is greater than the scaffold expanded diameter, even when the delivery balloon is hyper-inflated, or inflated beyond its maximum use diameter for the balloon-catheter.

Pattern 200 includes four links 237 (two at each end, only one end shown in FIG. 2) having structure formed to receive a radiopaque material in each of a pair of transversely-spaced holes formed by the link 237. These links are constructed in such a manner as to avoid interfering with the folding of struts over the link during crimping, which, as explained in greater detail below, is necessary for a scaffold capable of being crimped to a diameter of about at most Dmin or for a scaffold that when crimped has virtually no space available for a radiopaque marker-holding structure.

Figure 4:
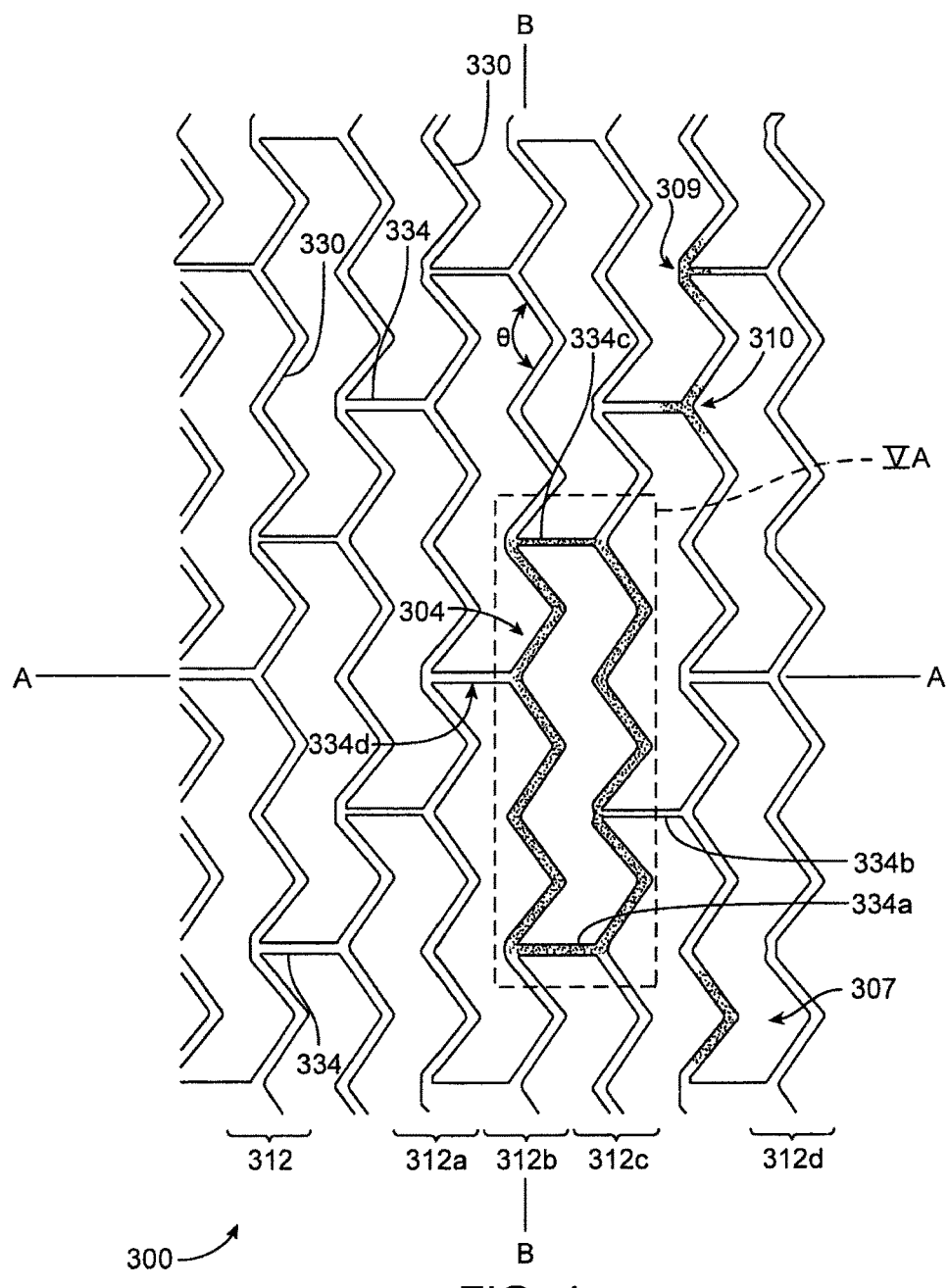
FIG. 4 is a partial planar view of a scaffold pattern according to a second embodiment of a scaffold.

A second embodiment of a scaffold structure has the pattern 300 illustrated in FIG. 4. Like the pattern 200, the pattern 300 includes longitudinally-spaced rings 312 formed by struts 330. A ring 312 is connected to an adjacent ring by several links 334, each of which extends parallel to axis A-A. The description of the structure associated with rings 212, struts 230, links 234, and crowns 207, 209, 210 in connection with FIG. 2, above, also applies to the respective rings 312, struts 330, links 334 and crowns 307, 309 and 310 of the second embodiment, except that in the second embodiment there are only three struts 334 connecting each adjacent pair of rings, rather than four. Thus, in the second embodiment the ring 312b is connected to the ring 312c by only three links 234 and to the ring 312a by only three links 334. A link formed to receive a radiopaque marker, similar to link 237, may be included between 312c and ring 312d.

Figure 5A:
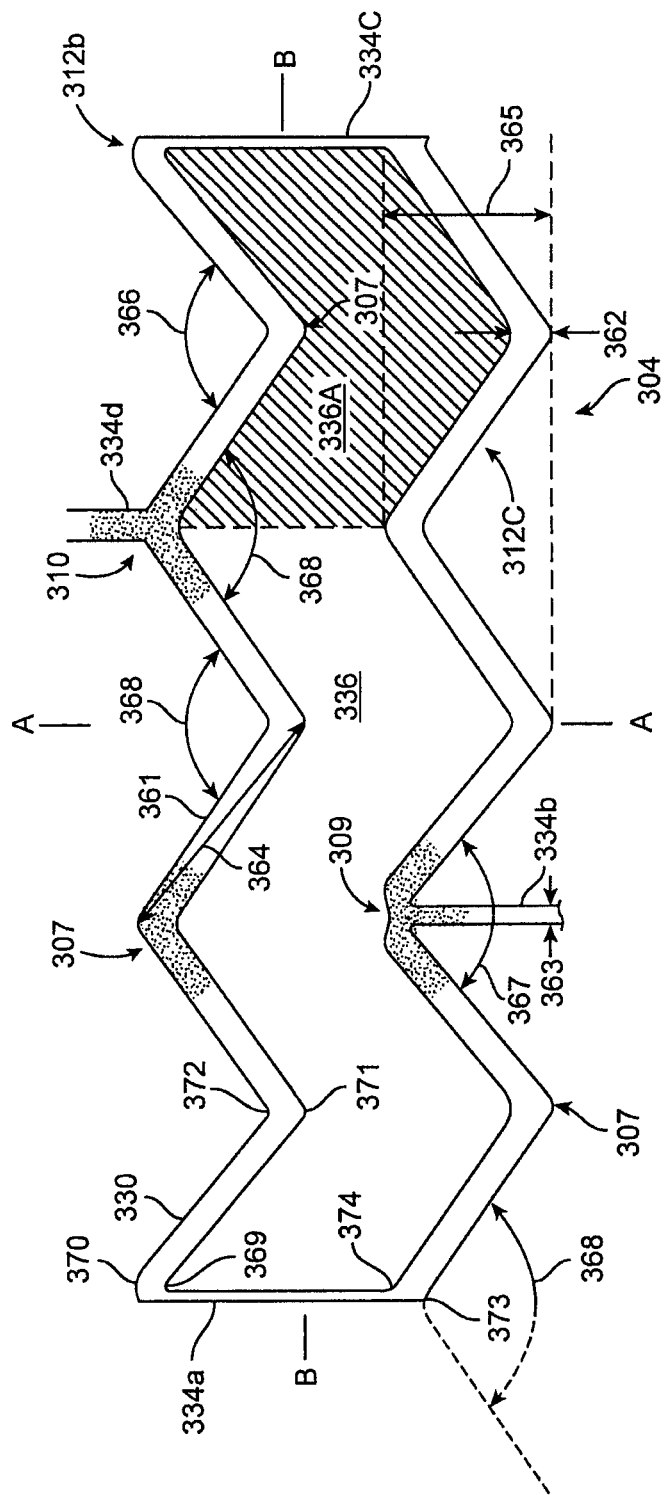
FIG. 5A is a planar view of a portion of the scaffold pattern of FIG. 4 taken at section VA-VA.
Figure 5B:
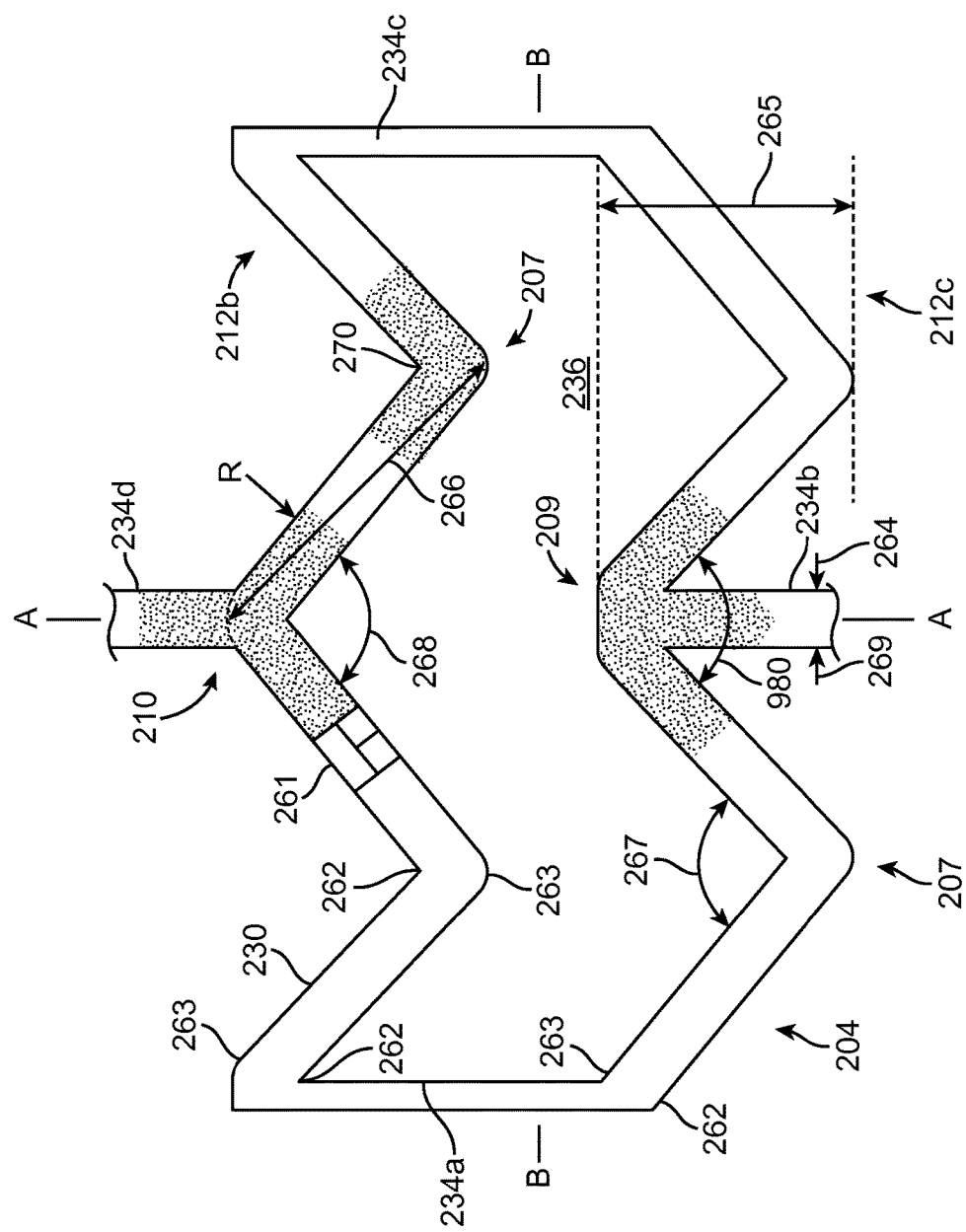
FIG. 5B is a planar view of a portion of the scaffold pattern of FIG. 2 taken at section VB-VB.

FIGS. 5A and 5B depict aspects of the repeating pattern of closed cell elements associated with each of the patterns 300 and 200, respectively. FIG. 5A shows the portion of pattern 300 bounded by the phantom box VA and FIG. 5B shows the portion of pattern 200 bounded by the phantom box VB. Therein are shown cell 304 and cell 204, respectively. In FIGS. 5A, 5B the vertical axis reference is indicated by the axis B-B and the longitudinal axis A-A. There are four cells 204 formed by each pair of rings 212 in pattern 200, e.g., four cells 204 are formed by rings 212b and 212c and the links 234 connecting this ring pair, another four cells 204 are formed by rings 212a and 212b and the links connecting this ring pair, etc. In contrast, there are three cells 304 formed by a ring pair and their connecting links in pattern 300.

Referring to FIG. 5A, the space 336 and 336a of cell 304 is bounded by the longitudinally spaced rings 312b and 312c portions shown, and the circumferentially spaced and parallel links 334a and 334c connecting rings 312b and 312c. Links 334b and 334d connect the cell 304 to the right and left adjacent ring in FIG. 3, respectively. Link 334b connects to cell 304 at a W-crown 309. Link 334d connects to cell 304 at a Y-crown 310. A "Y-crown" refers to a crown where the angle extending between a strut 330 and the link 334 at the crown 310 is an obtuse angle (greater than 90 degrees). A "W-crown" refers to a crown where the angle extending between a strut 330 and the link 334 at the crown 309 is an acute angle (less than 90 degrees). The same definitions for Y-crown and W-crown also apply to the cell 204. There are eight connected or free crowns 307 for cell 304, which may be understood as eight crowns devoid of a link 334 connected at the crown. There are one or three free crowns between a Y-crown and W-crown for the cell 304.

Additional aspects of the cell 304 of FIG. 5A include angles for the respective crowns 307, 309 and 310. Those angles, which are in general not equal to each other (see e.g., FIG. 6A for the "V2" and "V23" embodiments of scaffold having the pattern 300), are identified in FIG. 5A as angles 366, 367 and 368, respectively associated with crowns 307, 309 and 310. For the scaffold having the pattern 300 the struts 330 have strut widths 361 and strut lengths 364, the crowns 307, 309, 310 have crown widths 362, and the links 334 have link widths 363. Each of the rings 312 has a ring height 365. The radii at the crowns are, in general, not equal to each other. The radii of the crowns are identified in FIG. 5A as radii 369, 370, 371, 372, 373 and 374.

Cell 304 may be thought of as a W-V closed cell element. The "V" portion refers to the shaded area 336a that resembles the letter "V" in FIG. 6A. The remaining unshaded portion 336, i.e., the "W" portion, resembles the letter "W".

Referring to FIG. 5B, the space 236 of cell 204 is bounded by the portions of longitudinally spaced rings 212b and 212c as shown, and the circumferentially spaced and parallel links 234a and 234c connecting these rings. Links 234b and 234d connect the cell 204 to the right and left adjacent rings in FIG. 2, respectively. Link 234b connects to cell 236 at a W-crown 209. Link 234d connects to cell 236 at a Y-crown 210. There are four crowns 207 for cell 204, which may be understood as four crowns devoid of a link 234 connected at the crown. There is only one free crown between each Y-crown and W-crown for the cell 204.

Additional aspects of the cell 204 of FIG. 5B include angles for the respective crowns 207, 209 and 210. Those angles, which are in general not equal to each other (see e.g., FIG. 6B for the "V59" embodiment of a scaffold having the pattern 200), are identified in FIG. 5B as angles 267, 269 and 268, respectively associated with crowns 207, 209 and 210. For the scaffold having the pattern 200 the struts 230 have strut widths 261 and strut lengths 266, the crowns 207, 209, 210 have crown widths 270, and the links 234 have link widths 264. Each of the rings 212 has a ring height 265. The radii at the crowns are, in general, not equal to each other. The radii of the crowns are identified in FIG. 5B as inner radii 262 and outer radii 263.

Cell 204 may be thought of as a W closed cell element. The space 236 bounded by the cell 204 resembles the letter "W".

Comparing FIG. 5A to FIG. 5B one can appreciate that the W cell 204 is symmetric about the axes B-B and A-A whereas the W-V cell 304 is asymmetric about both of these axes. The W cell 204 is characterized as having no more than one crown 207 between links 234. Thus, a Y-crown crown or W-crown is always between each crown 207 for each closed cell of pattern 200. In this sense, pattern 200 may be understood as having repeating closed cell patterns, each having no more than one crown that is not supported by a link 234. In contrast, the W-V cell 304 has three unsupported crowns 307 between a W-crown and a Y-crown. As can be appreciated from FIG. 5A, there are three unsupported crowns 307 to the left of link 334d and three unsupported crowns 307 to the right of link 334b.

The mechanical behavior of a scaffold having a pattern 200 verses 300 differs in the following ways. These differences, along with others to be discussed later, have been observed in comparisons between the scaffold of FIGS. 6A-6B, which include in-vivo testing. In certain regards, these tests demonstrated mechanical aspects of scaffold according to the invention that were both unexpected and contrary to conventional wisdom, such as when the conventional wisdom originated from state of the art metallic stents, or coronary scaffold. For a particular design choice, whether driven by a clinical, production yield, and/or delivery profile requirement, therefore, the following characteristics should be kept in mind.

In general, a polymer scaffold that is crush-recoverable, possesses a desired radial stiffness and strength, fracture toughness and is capable of being crimped down to a target delivery diameter, e.g., at least about Dmin, balances the three competing design attributes of radial strength/stiffness verses toughness, in-vivo performance verses compactness for delivery to a vessel site, and crush recovery verses radial strength/stiffness.

In-vivo performance verses compactness for delivery to the vessel site refers to the ability to crimp the scaffold down to the delivery diameter. The ring struts 230 connecting crowns to form the W-cell 204 are more restrained from rotating about an axis tangent to the abluminal surface (axis A-A). In the case of the W-V cell the V portion, the crown may tend to twist about the axis A-A under particular configurations due to the reduced number of connecting links 336. The ring portions can in effect "flip", which means rotate or deflects out-of-plane as a result of buckling (please note: "out-of-plane" refers to deflections outside of the arcuate, cylindrical-like surface of the scaffold; referring to FIG. 5A "out-of-plane" means a strut that deflects normal to the surface of this figure). When there is a link 234 at each of a crown or valley as in FIG. 5B, any tendency for the crown to buckle or flip is reduced because the ring struts are more restrained by the link 236. Essentially, the link serves to balance the load across a ring more evenly.

The "flipping" phenomenon for a scaffold constructed according to pattern 300 has been observed during crimping, as explained and illustrated in greater detail in U.S. application Ser. No. 12/861,719. The W-V cell 304 is devoid of a nearby link 334 at a crown 307 to restrain excessive twisting of the adjacent crown or valley. In essence, when there are two crowns 307 between a link 334 the restraint preventing flipping or buckling of the V portion of the ring depends on the buckling strength of the individual ring strut 330, i.e., the strength and stiffness of the polymer strut in torsion. When there is a link 234 connected to each adjacent crown/valley (FIG. 5B), however, out of plane deflections at the crown 207 is restrained more, due to the bending stiffness added by the connected link 234, which restrains twisting at the adjacent crown 207.

A scaffold according to pattern 200 is correspondingly stiffer than a similarly constructed scaffold according to pattern 300. The scaffold according to pattern 200 will be stiffer both axially and in longitudinal bending, since there are more links 236 used. Increased stiffness may not, however, be desirable. Greater stiffness can produce greater crack formation over a less stiff scaffold. For example, the stiffness added by the additional links can induce more stress on rings interconnected by the additional links 234, especially when the scaffold is subjected to a combined bending (rings moving relative to each other) and radial compression and/or pinching (crushing). The presence of the link 234 introduces an additional load path into a ring, in addition to making the ring more stiff.

In-vivo requirements can favor a scaffold according to pattern 200, but a scaffold according to pattern 300 may be more easily crimped down to the delivery diameter. Other factors also affect the ability to crimp a scaffold. According to the disclosure, it was found that crown angles less than about 115 degrees for the pre-crimp scaffold can produce less fracture and related deployment problems (e.g., uneven folding/unfolding of ring struts) than scaffold with higher crown angles (relative to the inflated diameter, in one case 6.5 mm). The scaffold is crimped to a balloon that can be inflated up to about 7.4 mm. Thus, when the balloon is hyper-inflated the scaffold attains about up to about a 7 mm inflated diameter. For a balloon catheter-scaffold assembly according to the disclosure the largest inflated diameter for the balloon is less than or equal to the scaffold diameter before crimping. As mentioned above, it is preferred that the maximum inflated diameter for the scaffold is less than the scaffold diameter before crimping.

During the course of designing a crush recoverable polymer scaffold having a desired crimped profile, it was found that when forming the scaffold at the 8 mm diameter it was difficult to crimp the scaffold to a desired crimped profile, e.g., to crimp the scaffold from the 8 mm diameter to about 2 mm profile, for two reasons. First, by imposing the 350-400% diameter reduction requirement, the polymer material was more susceptible to crack formation and propagation, simply due to strain levels experienced by the scaffold when subjected to this extensive diameter reduction. This concern was addressed by adjusting stiffness, e.g., reducing the strut angle, wall thickness and/or number of crowns. Additionally, the process steps used to form the tube (FIG. 1) was found to help improve the scaffold's resistance to crack formation and propagation, as explained earlier.

Second, even when the scaffold dimensions were adjusted to limit crack formation, there was the problem of limited space for scaffold within the crimped profile. Due to the mass of material associated with the crimped scaffold, the available space for compression of the rings to the desired crimped profile was not achievable without creating unacceptable yield stresses or fracture. Thus, even when a 350-400% diameter reduction was achievable without crack or deployment problems, the scaffold pattern would not allow further reduction without exceeding the range of articulation that the scaffold design would allow.

According to another aspect of the disclosure, there are modified crown designs for a scaffold intended to improve the fracture toughness and/or reduce the delivery diameter of the scaffold. It was discovered that a design change to an existing scaffold pattern that would overcome a limitation on reduced profile, and which could be implemented using a brittle polymer like PLLA of PLGA, was a significant reduction in the size of the inner radius of the crown or valley bridging the struts that form the crown/valley.

Figure 7B:
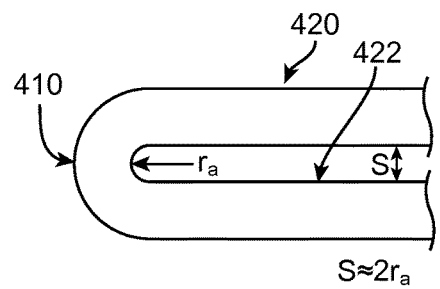

FIGS. 7A and 7B illustrate a pair of struts 420, 422 near a crown 410. In the pre-crimp state, the struts 420, 422 are separated by the crown angle φ and the crown is formed with an inner radius $r_a$. This is a typical design for a crown. The inner radius is selected to avoid stress concentrations at the crown. As the art has taught when there is a dramatic change in geometry at a hinge point, such as a crown, there is a greater likelihood cracks or yielding will form at the hinge point (thereby affecting radial strength) since the moment of inertia in bending across the crown is discontinuous.

In the case of a metal stent, the angle φ before crimping is less than the angle when the stent is deployed. By forming the stent with the reduced diameter, the stent may be more easily crimped to a small profile. Due to the presence of the inner radius, the angle φ is capable of being exceeded at deployment without loss of radial stiffness. If this radius is too small, however, and the strut angle at deployment exceeds φ, there is a greater chance of yielding or other problems to develop due to stress concentrations at the inner radius. Due to the ductility and resiliency of metal, stents made from metal may also be crimped down further than shown in FIG. 7B. The struts 420, 422 may touch each other, i.e., S is less than $2 \times r_a$, and yet the stent can still recover and maintain its radial stiffness despite the over crimped condition.

Figure 8A:
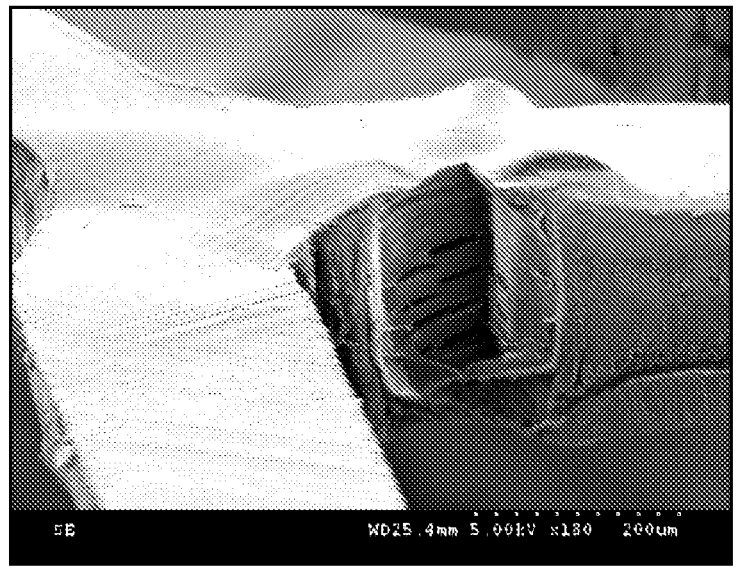
FIGS. 8A, 8F and 8G are scanning electron microscope (SEM) photographs of scaffold crowns having an inner radius substantially higher than the inner radius of the scaffold crowns in FIGS. 8B, 8C and 8D. The photographs are taken after the scaffold was expanded by a balloon.
Figure 8B:
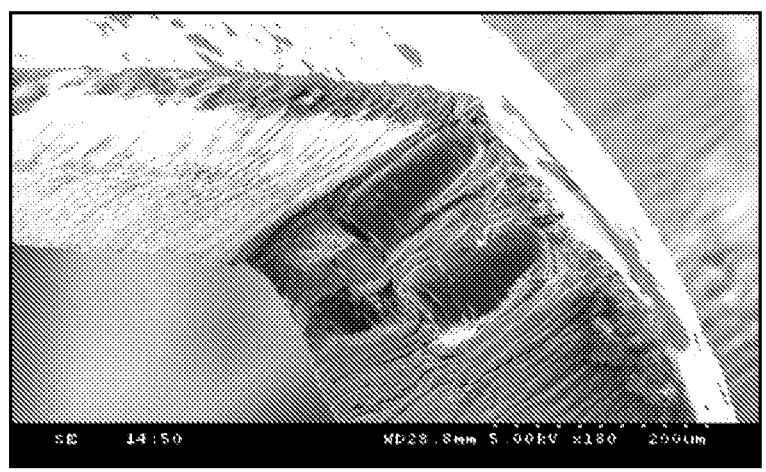
FIGS. 8B, 8C and 8D are scanning electron microscope (SEM) photographs of scaffold crowns. The crowns have an inner radius of about 0.00025 inches. The photographs are taken after the scaffold was expanded by a balloon.
Figure 8C:
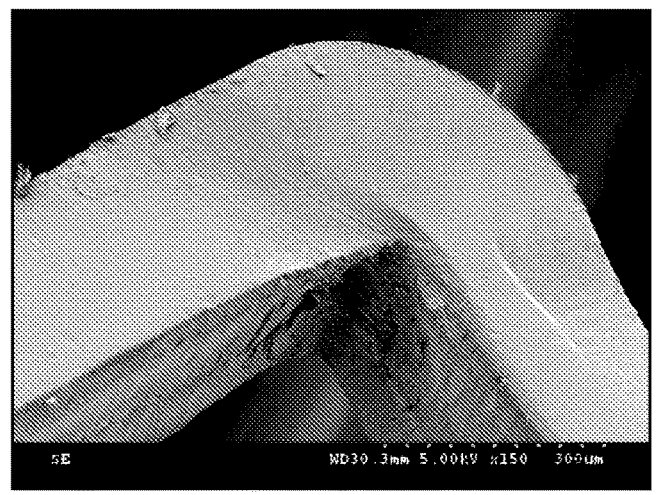
Figure 8D:
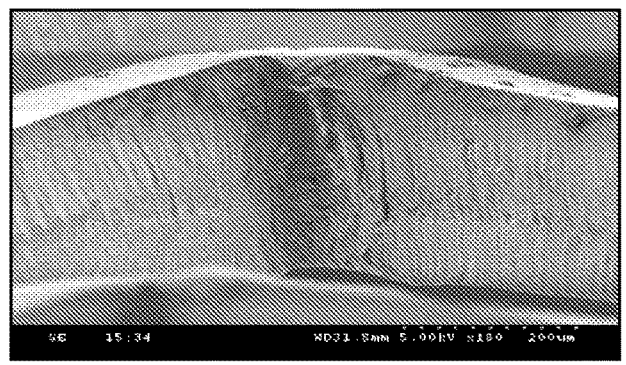
Figure 8E:
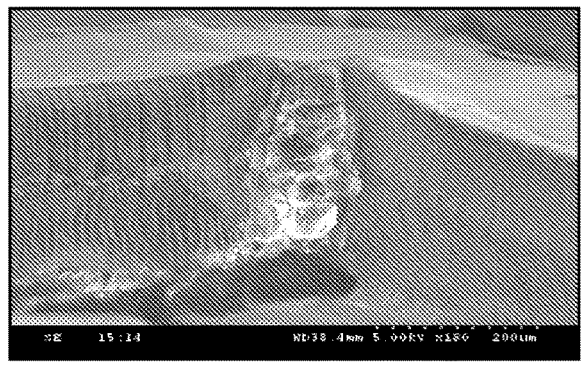
FIG. 8E is another scanning electron microscope (SEM) photographs of a scaffold crown.
Figure 8F:
Figure 8G:
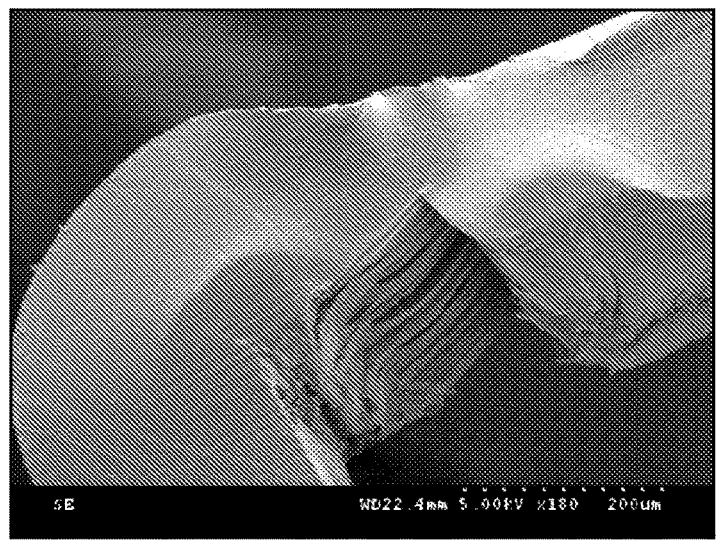

For polymer scaffold, however, it has been found that the distance S (FIG. 7B) should not generally be smaller than allowed for the radius $r_a$, i.e., S greater than or equal to 2 $r_a$. For a polymer scaffold, if the struts 420, 422 are brought closer to each other, i.e., S becomes less than $2 \times r_a$, the brittleness of the material can likely result in fracture problems when the scaffold is deployed. The scaffold may not therefore be able to maintain its radial stiffness if crimped beyond the allowable distance for the radius. The scanning electron microscope (SEM) photographs included as FIGS. 8A, 8F and 8G show fractures at crowns when the distance S in FIG. 7B is less than $2 \times r_a$. As can be seen in these photographs, there is significant material failure in a W crown, free crown and Y crown.

With the objective of decreasing the distance S between struts 420, 422 (FIG. 7B) the inventors decided to reduce down the radius $r_a$ as small as possible, despite the advice offered by the art. It was discovered, to their surprise, that the scaffold was able to recover from the crimped condition to the expanded condition without significant, noticeable, reoccurring or prohibitive loss in radial strength. The SEMs provided as FIGS. 8B, 8C and 8D show crowns/valleys having reduced radii after being crimped, then expanded by the balloon. In these examples the crown inner radii were made as small as the cutting tool (a green light pico-second laser, described above) was able to produce. As can be seen by comparing FIGS. 8A, 8F and 8G with FIGS. 8B, 8C and 8D the scaffold having reduced radii produced some voids but there is no crack propagation. Structural integrity was maintained. The deployed scaffold in these photos maintained good radial stiffness.

Figure 7C:
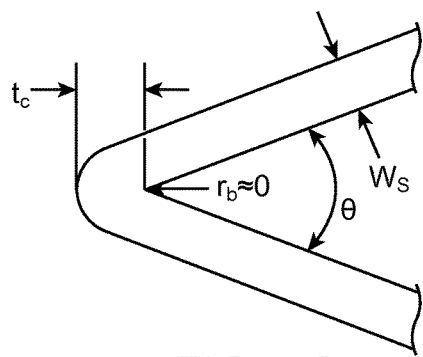
FIG. 7C-7D shows a scaffold crown formation in its expanded and crimped states for a scaffold according to the first embodiment.
Figure 7D:
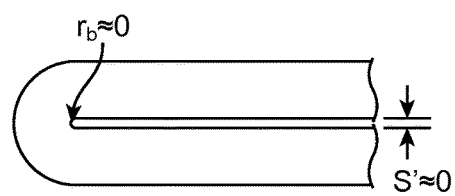

FIGS. 7C and 7D illustrate embodiments of a crown formation that produced these unexpected results. An example of a W cell having a reduced radii type of crown formation just described is illustrated in FIGS. 5B and 6B. The radius $r_b$ is about 0.00025 inches, which corresponds to the smallest radius that could be formed by the laser. The 0.00025 inch radius is not contemplated as a target radius or limit on the radius size, although it has produced the desired result for this embodiment. Rather, it is contemplated that the radius may be as close to zero as possible to achieve a reduced profile size. The radius, therefore, in the embodiments can be about 0.00025 (depending on the cutting tool), greater than this radius, or less than this radius to practice the invention in accordance with the disclosure, as will be appreciated by one of ordinary skill in the art. For instance, it is contemplated that the radii may be selected to reduce down the crimped size as desired.

An inner radius at about zero, for purposes of the disclosure, means the minimum radius possible for the tool that forms the crown structure. An inner radius in accordance with some embodiments means the radius that allows the distance S to reduce to about zero, i.e., struts are adjacent and/or touch each other as shown in FIG. 7D (S' is about, or zero).

Without wishing to be tied to a particular theory for how the scaffold according to the invention is capable of being reduced down to the theoretical minimum diameter and then expanded without loss of strength, it is believed that the selection of starting diameter being greater than the inflated diameter played a role in the favorable outcome. In contrast to the previous example where a metal stent is formed from a diameter less than its inflated diameter, which smaller diameter may be selected to facilitate a smaller crimped profile, a polymer scaffold according to preferred embodiments is formed from a starting diameter greater than the maximum inflated diameter for the balloon catheter-scaffold assembly (a larger starting diameter may be preferred to reduce acute recoil, as explained below, and/or to enhance radial strength characteristics in the deployed state as explained earlier in the tube processing steps for the tube of FIG. 1). As such, the strut angle pre-crimp is preferably greater than the maximum crown/strut angle when the scaffold is deployed. Stated differently, the crown angle in FIG. 7C (pre-crimp angle) is never exceeded when the balloon expands the scaffold from the crimped to deployed state. This characteristic of the crush recoverable polymer scaffold, i.e., pre-crimp crown angle greater than the deployed crown angle, is believed to provide clues as to how the polymer scaffold in the SEM photographs was able to retain radial strength when a minimum inner radius was used for the crown formation, contrary to the prior art. Compression, but not expansion of the scaffold when loaded by the vessel, it is believed, will not induce further weakening, despite the presence of voids. When the crown experiences only a compressive deformation relative to its pre-crimp shape (FIG. 7C), the potentially weakened area near the inner radius is subjected to only compressive stresses, which do not tend to tear the crown apart, i.e., induce crack propagation.

Crimping of the scaffold, as detailed in U.S. application Ser. No. 12/861,719, includes heating the polymer material to a temperature less than, but near to the glass transition temperature of the polymer. In one embodiment the temperature of the scaffold during crimping is raised to about 5 to 10 degrees below the glass transition temperature for PLLA. When crimped to the final, crimped diameter, the crimping jaws are held at the final crimp diameter for final dwell period. This method for crimping a polymer scaffold having crush recovery is advantageous to reduce recoil when the crimp jaws are released. Another, unexpected outcome, however, was found relating to the reduced inner radius aspect of the disclosure. It was found that during the dwell period the polymer scaffold crimped profile could be reduced to a profile less than the theoretical minimum profile.

From the example given earlier for the scaffold of FIG. 6B, the value for Dmin is 0.1048" or 2.662 mm. When crimping this scaffold according to the crimping procedure summarized above and described in U.S. application Ser. No. 12/861,719, it was found that the scaffold could be reduced down to a crimped profile of 0.079" or 2.0066 mm. Hence, the crimped profile was less than Dmin for this scaffold. With this profile a protective sheath of 0.085" OD could be placed over the scaffold. When a drug coating was disposed over the scaffold, the profile of the scaffold with sheath was 0.092". For this scaffold the range of radial strength was 0.45-0.65 N/mm, range of radial stiffness was 1.00-1.20 N/mm and the crush recoverability was about 90% (50% crush).

It is believed that a reduced profile less than Dmin was achieved due to a compression of the material during the dwell period. Essentially, the pressure imposed by the crimping jaws during the dwell period at the raised temperature caused the struts forming the ring to be squeezed together to further reduced the crimped scaffold profile. According to these embodiments, the crimped scaffold having a profile less than its theoretical minimum profile was successfully deployed and tested in vivo. This scaffold possessed the desired radial stiffness properties, in addition to the desired crush recovery of above about 90% following a 50% reduction in diameter.

Figure 7E:
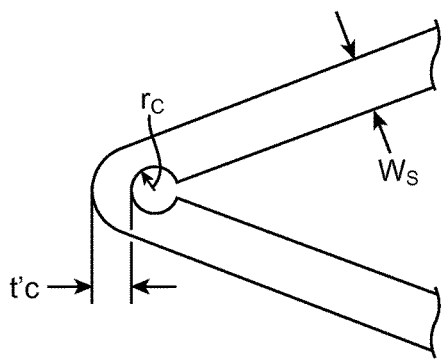
FIG. 7E-7F shows a scaffold crown formation in its expanded and crimped states for a scaffold according to an alternative embodiment.

In another aspect of this disclosure, the strut and crown formation for a crush recoverable polymer scaffold is formed to take the shape depicted in FIG. 7E, for purposes of achieving a crimped profile less than the crimped profile for the scaffold having the crown formation shown in FIG. 7A. According to these embodiments, the crown is formed with a radius $r_c$ as shown. When this scaffold is crimped, the struts may be brought close together so that the distance separating them is near zero (S" is about, or zero). In contrast to the embodiments of FIG. 7C, the radius $r_c$ is made some finite or larger radii than by forming a hole or enlarged area between the ends of the struts and crown. The thickness at the crown, $t_c'$ forming the inner radius along its inner surface may be less than the strut width (in the example of FIG. 7C and FIG. 16 the crown thickness may be larger than the strut width). This can allow a larger inner radius to be used at the crown without increasing the crimped profile.

Figure 7F:
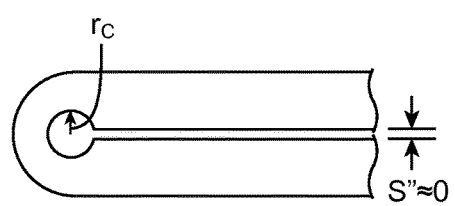

In these embodiments, a scaffold having the crown formation depicted in FIGS. 7E-7F is referred to as a "key-hole" crown formation. The name will be understood without further clarification by reference to FIG. 7F, which shows a key-hole slot or opening formed by the inner wall surfaces. In the crimped profile, the struts near the crown may be brought closer together while a hole or opening having radius $r_c$ is more or less maintained at the crown. The distance S" is less than twice the radius $r_c$ for the "key-hole" crown formation.

Examples of scaffold embodying patterns 300 and 200 are provided in FIGS. 6A-6B (referred to as the V2 embodiment, which has a 0.008 inch wall thickness, V23 embodiments having 0.008 and 0.014 inch wall thickness and the V59 embodiment, which has a 0.011 inch wall thickness). Specific values for the various cell attributes of FIGS. 5A-5B are provided.

The scaffold V59 (pattern 200) having a pre-crimp diameter of 8 mm is capable of being crimped to a non-compliant balloon wherein the crimped profile is about 2 mm. The inflated diameter is about 6.5 mm in this example. The scaffold V2, V23 having pre-crimp diameters 7 and 9, respectively, are expanded to about 6.5 mm by a non-compliant balloon. The V2 and V23 scaffold are capable of being crimped to diameters of about 0.092 inches (2.3 mm).

According to the disclosure, it was found that the aspect ratio (AR) of a strut of a scaffold may be between about 0.8 and 1.4, the AR of a link may be between about 0.4 and 0.9, or the AR of both a link and a strut may between about 0.9 and 1.1, or about 1. Aspect ratio (AR) is defined as the ratio of width to thickness. Thus for a strut having a width of 0.0116 and a wall thickness of 0.011 the AR is 1.05.

According to the disclosure, the radial strength of a balloon expanded polymer scaffold having crush recoverability has a radial strength of greater than about 0.3 N/mm, or between about 0.32 and 0.68 N/mm, and a radial stiffness of greater than about 0.5 N/mm or between about 0.54 N/mm and 1.2 N/mm. According to the disclosure, a crush-recoverable scaffold has these ranges of stiffness and strength for a scaffold having a wall thickness of about 0.008" to 0.014" and configured for being deployed by a 6.5 mm non-compliant balloon from about a 2 mm crimped profile, or deployed to a diameter of between about 6.5 mm and 7 mm from about a 2 mm crossing profile on a balloon catheter.

A biodegradable polymer, such as PLLA (and polymers generally composed of carbon, hydrogen, oxygen, and nitrogen) is radiolucent with no radiopacity. It is desirable for a scaffold to be radiopaque, or fluoroscopically visible under x-rays, so that accurate placement within the vessel may be facilitated by real time visualization of the scaffold body, preferably the end rings. A cardiologist or interventional radiologist typically will track a delivery catheter through the patient's vasculature and precisely place the scaffold at the site of a lesion using fluoroscopy or similar x-ray visualization procedures. For a scaffold to be fluoroscopically visible it must be more absorptive of x-rays than the surrounding tissue. Radiopaque materials in a scaffold may allow for its direct visualization. One way of including these materials with a biodegradable polymer scaffold is by attaching radiopaque markers to structural elements of the scaffold, such as by using techniques discussed in U.S. application Ser. No. 11/325,973. However, in contrast to other stent or scaffold, a biodegradable, bioabsorbable, bioresorbable, or bioerodable, and peripherally implanted scaffold having crush recoverability according to the disclosure has special requirements not adequately addressed in the known art.

There is the unmet need of maintaining a desired stiffness property in the vicinity of the marker-holding material (marker structure) without increasing the minimum crimped diameter, e.g., Dmin. The marker-holding material must not interfere with the extremely-limited space available for achieving the required crossing profile or delivery diameter for the crimped scaffold on the delivery catheter, particularly in the case of a scaffold that has a diameter reduction of 300-400% or more when crimped from the starting, pre-crimp diameter to the delivery diameter, and/or where the target delivery diameter is about at most a theoretical minimum diameter (Dmin) for the scaffold. It has been found that in order to be capable of achieving a desired delivery diameter, e.g., 300-400% or more diameter reduction during crimping, the marker material (when located on a link) should not interfere with the folding of the struts forming rings of the scaffold. However, when addressing this need without consideration for the effect on radial stiffness, it was found that there was an unacceptable loss in stiffness in the vicinity of the marker structure.

Figure 9A:
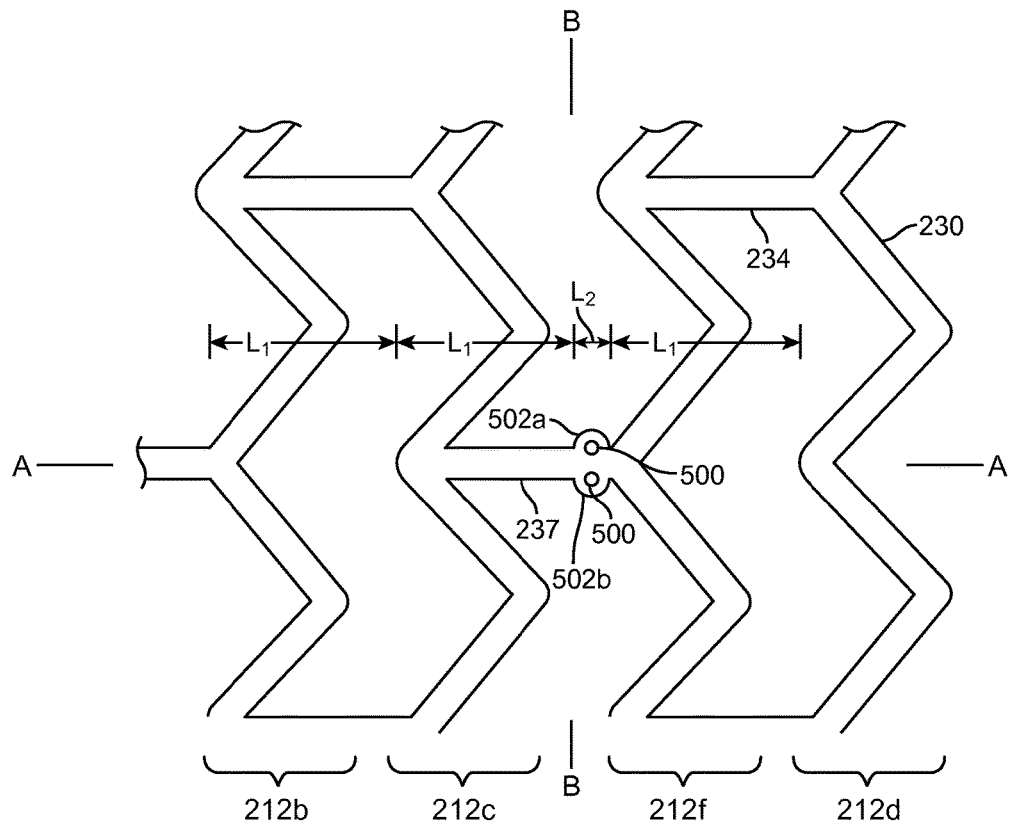
FIGS. 9A-9B show the first embodiment of a scaffold including a radiopaque marker structure formed on a link connecting rings.
Figure 9B:
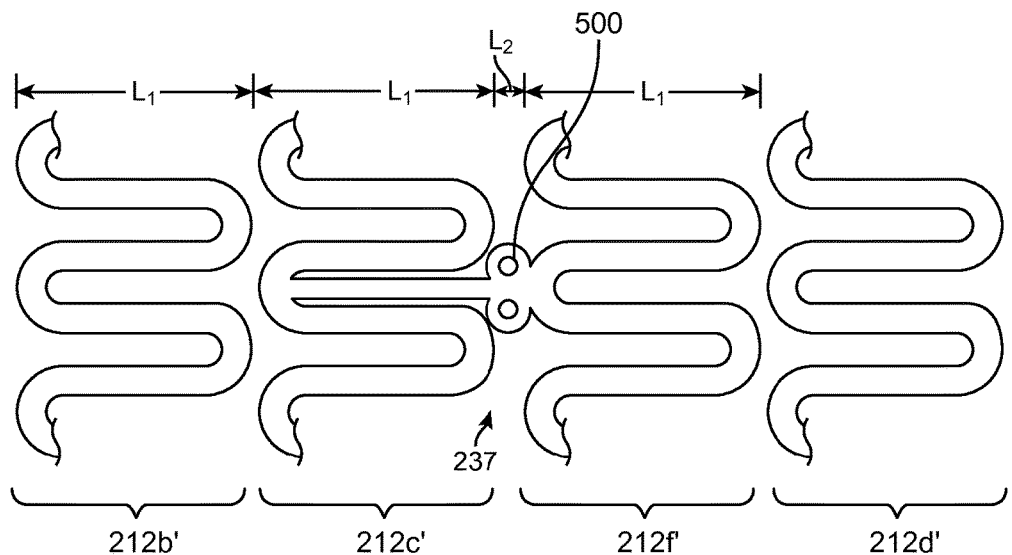

Referring to FIGS. 9A and 9B there are shown portions of the scaffold according to pattern 200. FIG. 9A shows the portion of the scaffold where the link 237 holding a radiopaque material 500 (marker 500) is located. FIG. 9B shows this same portion of the scaffold when configured in a crimped configuration. The rings 212b, 212c, 212d and 212f are shown in their compressed, folded or compact configuration as crimped rings 212b', 212c', 212d' and 212f', respectively. So that each of the rings 212 may have the same radial stiffness properties (ignoring link connections), the pair of markers 500 is preferably located on the link 237, as opposed to on a ring strut 230. In other embodiments the marker 500 may be located on the ring 212 by making suitable accommodation in the ring structure.

As can be appreciated from FIG. 9B, in order to maintain the minimum diameter, e.g., about at least the theoretical minimum crimped diameter (Dmin) for the crimped scaffold, the presence of marker structure preferably has no effect on the distance between folded struts 230. To achieve this result, the length of the link 237 may be increased, ($L_{237}=L_1+L_2$,) over the length $L_1$ of the other links 234 that do not have the markers to carry (the length $L_2$ being about the length needed to accommodate marker structure (depots 502 and the pair of markers 500), without interfering or limiting the folding of struts 230 as necessary to achieve a 300-400% or more diameter reduction. Stents or scaffold that do not have a tight crimped diameter requirement or minimum space between structural elements of a scaffold, by contrast, may have the link connecting rings increased in size beneath the fold struts to hold a marker 500, since there remains available space for marker structure in the crimped configuration.

The depots 502 may be formed when the scaffold is cut from the tube. The depots 502 provide a hole sized slightly smaller than a diameter of a marker 500 sphere, e.g., a platinum sphere, so that the sphere may be placed in the hole and secured therein as a drug-polymer coating is applied over the scaffold. The drug-polymer coating can serve as an adhesive or barrier retaining the marker 500 within the hole of a depot 502.

In one aspect of the disclosure the diameter of a sphere forming the marker 500 necessary to achieve adequate illumination is less than the wall thickness (235, FIG. 3) of the polymer scaffold. As such, the sphere may be placed within the hole and then a coating applied over it. Since the sphere diameter is about equal to or less than the wall thickness 235 no reforming, or shaping of the sphere is necessary to achieve a flat profile. A process of applying the marker, therefore, is simplified.

When the length of a link having marker structure is increased to maintain the minimum crimped diameter according to the embodiments of FIG. 9, however, the combined radial stiffness properties of the nearby rings is reduced since they are spaced further apart. To minimize this loss in stiffness, particularly with respect to the end ring (which is inherently less stiff since it is connected to only one neighboring ring), the marker structure is located between links 212c and 212f, as opposed to rings 212d and 212f. Additionally, the marker structure is arranged so that the marker pair 500 is placed in depots 502a, 502b orientated along the vertical axis B-B as opposed to longitudinally (axis A-A). By placing the depots 502a and 502b along axis B-B the length $L_2$ is preferably less than if the markers 500 were disposed longitudinally, so that the undesirable loss in the combined radial stiffness of the adjacent rings 212c, 212f (resulting from the increased length of link 237) and the end ring 212d is minimal.

Figure 10A:
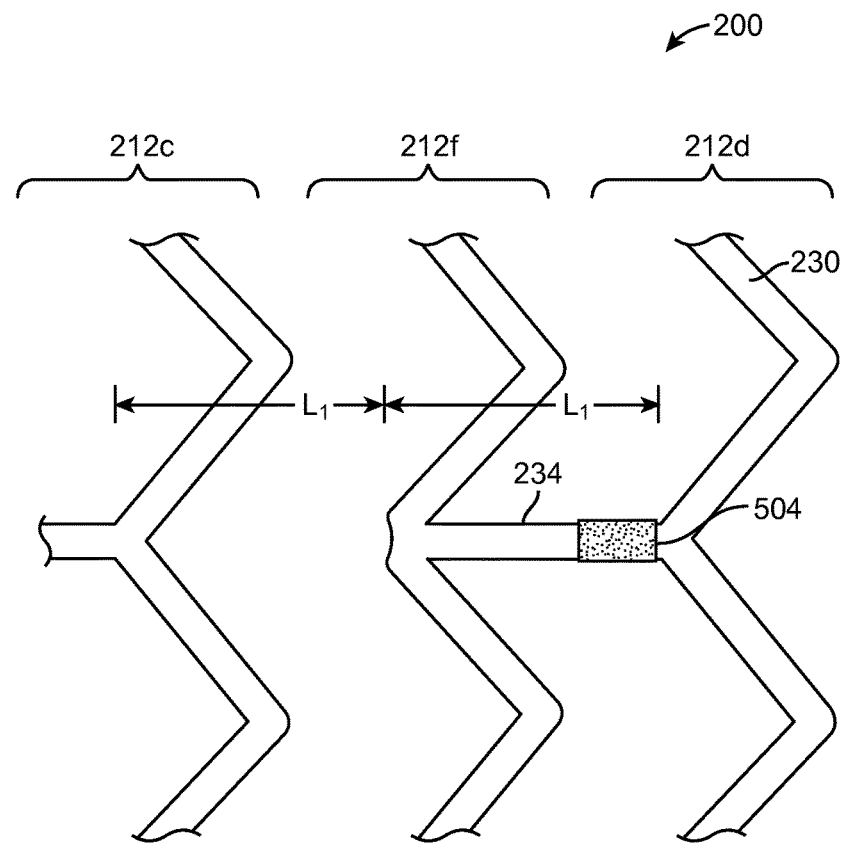
FIGS. 10A-10B show an alternative embodiment of a scaffold including a radiopaque marker disposed on a link connecting rings.
Figure 10B:
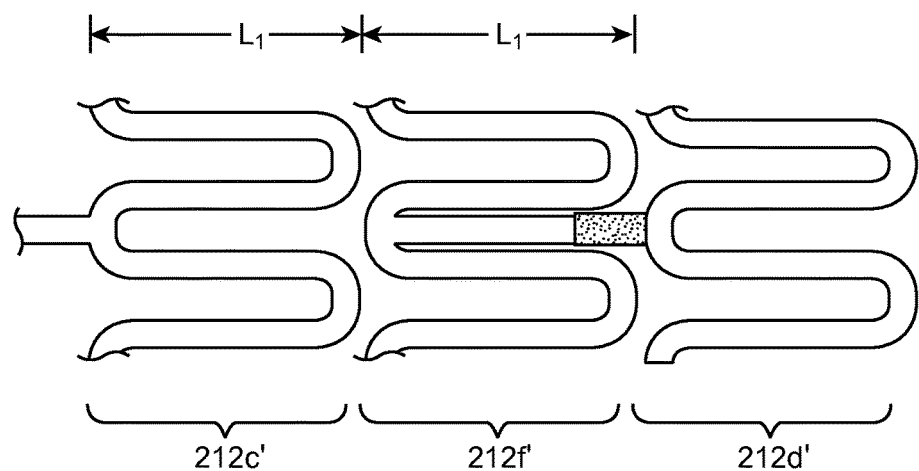

According to another embodiment of a marker for the polymer scaffold, a scaffold according to the pattern 200 may be devoid of link 237 having the marker structure and increased length needed to accommodate crimping requirements. Referring to FIGS. 10A and 10B, instead, a radiopaque sheet of material 504, e.g., a 0.025" length and 0.004" thick gold, platinum or Iridium foil, is wrapped around a link 234 and held in place by, e.g., a drug-polymer coating deposited over the scaffold. Since the thickness of the foil may be negligible, or the material compressible during crimping, the scaffold may be capable of maintaining at least about a Dmin crimped diameter despite the presence of the marker 504 between folded struts 230. According to these embodiments, since the foil does not affect scaffold function—the link length may be about the same as other links 234—the foil may be preferably placed nearer to the end of the scaffold to facilitate easier identification of the scaffold end within the vessel. For example, the marker 504 may be located on the link connecting ring 212d to ring 212f since stiffness properties are not affected by the presence of the marker 504.

Figure 11A:
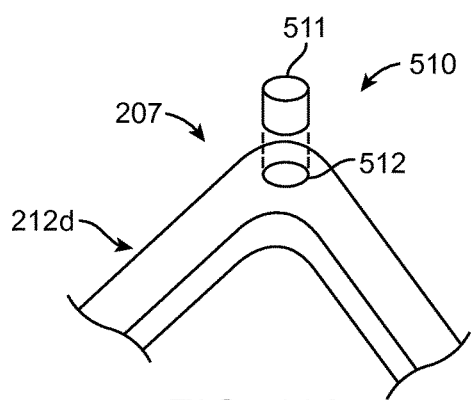
FIGS. 11A-11E are several alternative embodiments of a scaffold including a radiopaque marker. For these embodiments the radiopaque marker(s) are located on or near the crown of a crown, as opposed to on a link connecting rings.
Figure 11B:
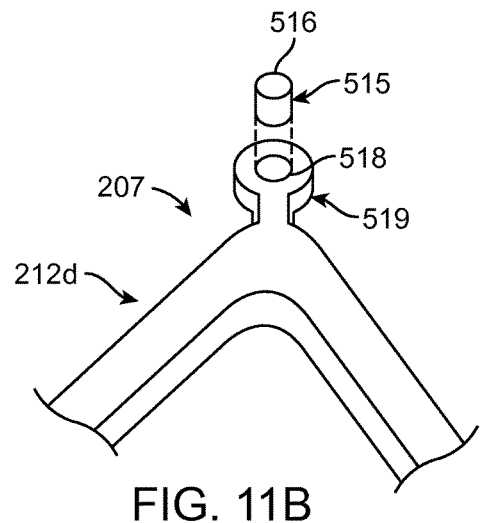
Figure 11C:
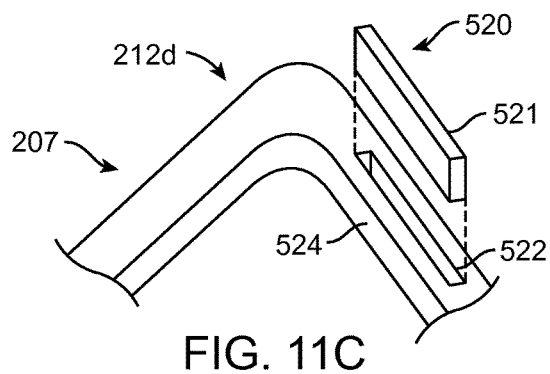
Figure 11D:
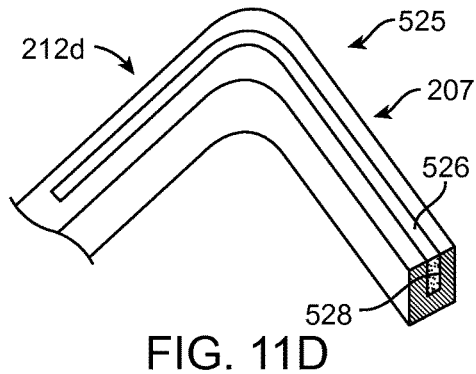
Figure 11E:
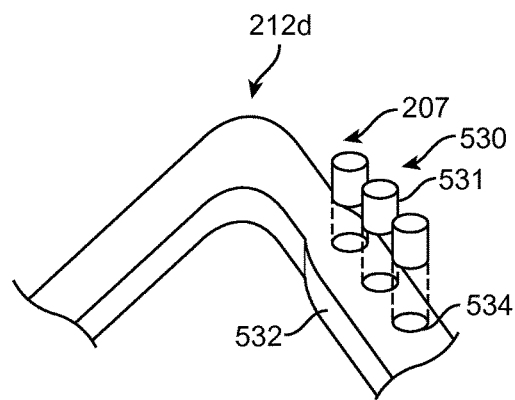

According to other embodiments of a marker for the polymer scaffold, as depicted in FIGS. 11A and 11E, a scaffold according to the pattern 200 is modified in the ring structure to hold a radiopaque marker. By placing marker(s) material on or near a crown 207 of the end ring 212d, as shown in FIGS. 11A-11E, the location of the end ring 212d in the vessel can be more easily located (since the marker is located on the end ring). According to the embodiments depicted in FIGS. 11A, 11B and 11E one or more cylindrically shaped markers 511, 516, 531, respectively, may be located at the crown 207 (FIGS. 11A and 11B) or near the crown 207 as in FIG. 11E. According to the embodiments depicted in FIGS. 11C and 11D one or more strips of radiopaque material 521, 526 are placed near the crown (FIG. 11C) or around the crown (FIG. 11D).

A single marker 511 may be received in a hole 512 formed at the crown 207, in the case of FIG. 11A, or received in a hole provided by an eyelet 519 that extends from the crown 207, as shown in FIG. 11B. In the later case, it may be necessary to increase the ductility, or fracture toughness of the material forming the extension 519 to avoid the eyelet breaking off from the crown 207. Since there is no strength/stiffness requirements for this eyelet, it may be practical to alter the material locally so that it is more fracture resistant without affecting the stiffness of the crown. For example, Toughness could be achieved by local heat treatment, local plasticization, or a local coating application. Local heat treatment could be particularly useful if a polymer blend or a block copolymer is used in the backbone of the scaffold. FIG. 11E shows three radiopaque pieces 531 received in three holes formed in the strut 532, which has been made thicker to accommodate for the loss in strength of the strut 230 due to the presence of the holes 534.

FIGS. 11C and 11D show examples of a strip of radiopaque material 521, 526 received in slots 522, 528, respectively, formed in the ring 212b. The strip 521 may be located in the strut 524, or the strip 526 may be located about the crown 207 to increase visibility of the crown. These design choices should also take into account the affect on the bending stiffness of this crown, which is also true of the embodiment of FIG. 11A. Preferably the slot 522, 528 coincides with the neutral axis of the strut and/crown to minimize the effect on bending stiffness at the crown.

In other embodiments the strips 521, 526 may be made from a material consisting of radiopaque particles dispersed in a bioresorbable material, e.g., 60% Tungsten particles. This embodiment has the advantage of dispersing the radiopaque material within the vessel after the scaffold has biodegraded.

In another embodiment a scaffold may have links connecting the end rings lengthened to accommodate a marker, e.g., as shown in FIG. 9A-9B, without losing substantial radial strength or stiffness at the end ring (due to the increased length of the link) by having metallic spring elements inserted into the crowns. Thus, according to this embodiment there is a marker element.

Figure 11F:
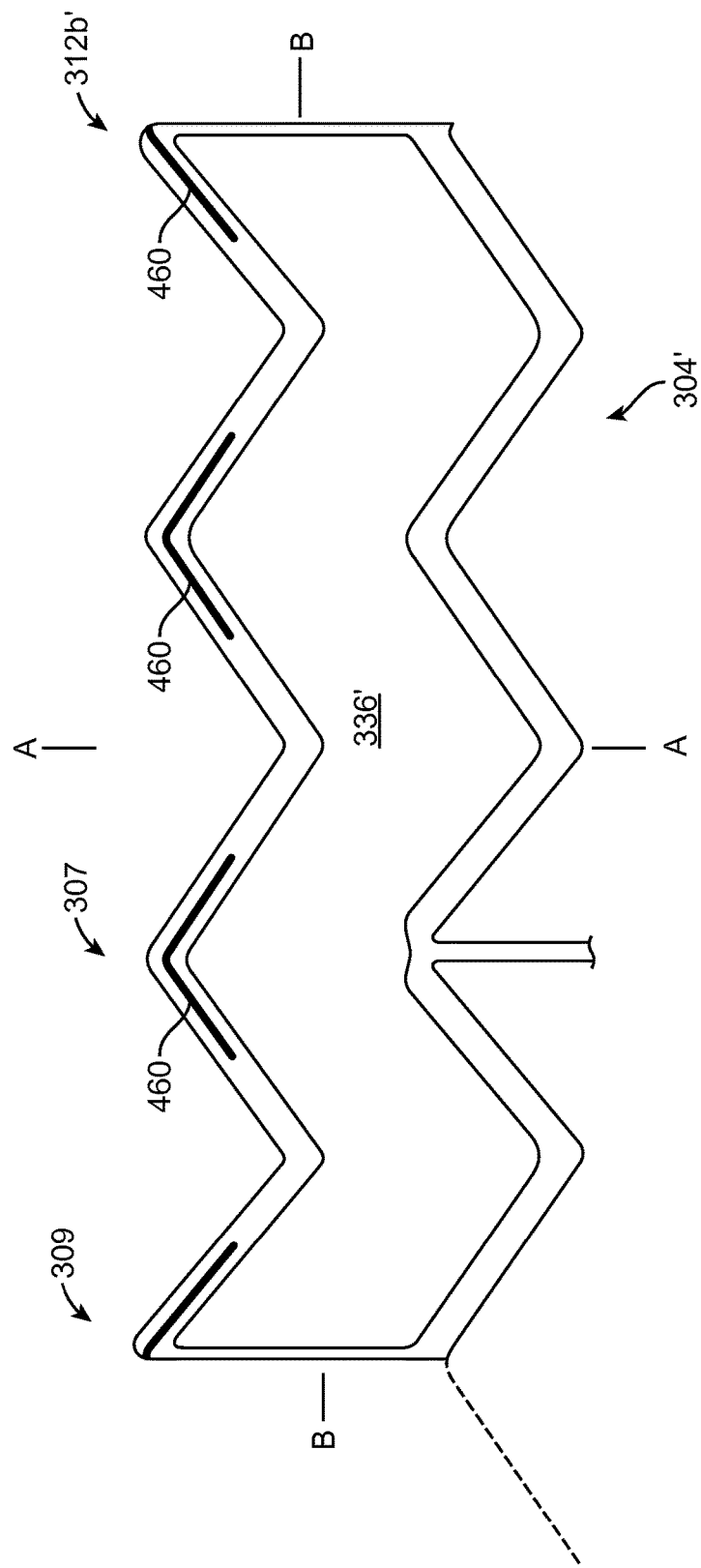
FIG. 11F depicts an alternative embodiment of a scaffold having a radiopaque marker. In this example the radiopacity is provided through material used to strengthen the crown at an end ring. As such, the embodiments provide more visibility at the end ring while also strengthening the end ring.

In another embodiment a metallic or composite metal-polymer spring may serve a dual role of providing greater visibility and strengthening the end ring. Referring to FIG. 11F there is shown a modified form of the non-symmetric cell 304' when the end ring 312b' forms one of its sides. At the free crown 307, Y-crown 309 and W crown 310 there is an arched strengthening element, or spring 460 embedded in the crown. The material for member 460 may be, or may include, e.g., Iron, Magnesium, Tungsten to provide, in addition to added strength/stiffness at the crown, greater visibility of the end of the scaffold when implanted within the body as these materials are radiopaque. The positioning of the member 460 relative to a strut's neutral axis may be closest to its edge such as nearest the outer end of the crown, e.g., furthest from the inner radius of the crown so that the tensile ultimate stress across the strut when the ring is under compression is increased mostly due to the presence of the member 460. The member 460 is preferably located at each of the crowns at the end ring to serve a dual role of providing greater visibility and adding additional radial strength and stiffness to the end ring (which would otherwise have less radial stiff than interior ring structure since the end ring is connected to only one neighboring ring).

Design Process

As mentioned earlier, the problem may be stated in general terms as achieving the right balance among three competing design drivers: radial strength/stiffness verses toughness, in-vivo performance verses compactness for delivery to a vessel site, and crush recovery verses radial strength/stiffness.

Embodiments having patterns 200 or 300 were found to produce desired results with particular combinations of parameters disclosed herein, or readily reproducible in light of the disclosure. It will be recognized there were no known predecessor balloon-expandable stents having adequate crush recovery to use as a guide (indeed, the art had discouraged such a path of development for a peripheral stent). As such, various polymer scaffold combinations were fabricated based and the following properties evaluated to understand the relationships best suited to achieve the following objectives:

Crush recoverability of the scaffold without sacrificing a desired minimal radial stiffness and strength, recoil, deployability and crimping profile;

Acute recoil at deployment—the amount of diameter reduction within ½ hour of deployment by the balloon;

Delivery/deployed profile—i.e., the amount the scaffold could be reduced in size during crimping while maintaining structural integrity;

In vitro radial yield strength and radial stiffness;

Crack formation/propagation/fracture when crimped and expanded by the balloon, or when implanted within a vessel and subjected to a combination of bending, axial crush and radial compressive loads;

Uniformity of deployment of scaffold rings when expanded by the balloon; and

Pinching/crushing stiffness.

These topics have been discussed earlier. The following provides additional examples and conclusions on the behavior of a scaffold according to the disclosure, so as to gain additional insight into aspects of the disclosed embodiments.

A scaffold fabricated with a pattern similar to pattern 300 (FIG. 4) possessed a good amount of crush recoverability, however, this scaffold's other properties were not ideal due to memory in the material following balloon expansion. The scaffold, which was initially formed from a 6.5 mm tube and deployed to about the same diameter, had acute recoil problems—after deployment to 6.5 mm it recoiled to about a 5.8 mm diameter. The scaffold also exhibited problems during deployment, such as irregular expansion of scaffold rings.

One attempt at solving the design problem proceeded in the following manner. The scaffold's properties were altered to address stiffness, strength, structural integrity, deployment and recoil problems while maintaining the desired crush recoverability. Ultimately, a scaffold was designed (in accordance with the disclosure) having the desired set of scaffold properties while maintaining good crush recovery properties after a 50% pinch deformation, which refers to the scaffold's ability to recover its outer diameter sufficiently, e.g., to about 90-95%, following a crushing load that depresses the scaffold to a height about equal to 50% of its un-deformed height.

The pinching stiffness (as opposed to the radial stiffness) is most influenced or most sensitive to changes in the wall thickness of the scaffold. As the wall thickness increases, the pinching stiffness increases. Moreover, the crush recoverability of a scaffold is most affected by the stresses created at the regions that deflect most outward in response to the applied load. As explained below, as the wall thickness is increased, the crush recoverability decreases due to an increased concentration of strain energy at the outwardly deflected ends of the scaffold. A design for a crush recoverable scaffold, therefore, must balance the wall thickness for increased pinching stiffness against the reduction in crush recoverability resulting from an increased pinching stiffness. Similarly, although radial stiffness is less affected by changes in wall thickness (since loads are more predominantly in-plane loading as opposed to out of plane during pinching) when wall thickness is altered to affect crush recoverability the radial stiffness must be taken into consideration. Radial stiffness changes when the wall thickness changes.

Figure 12A:
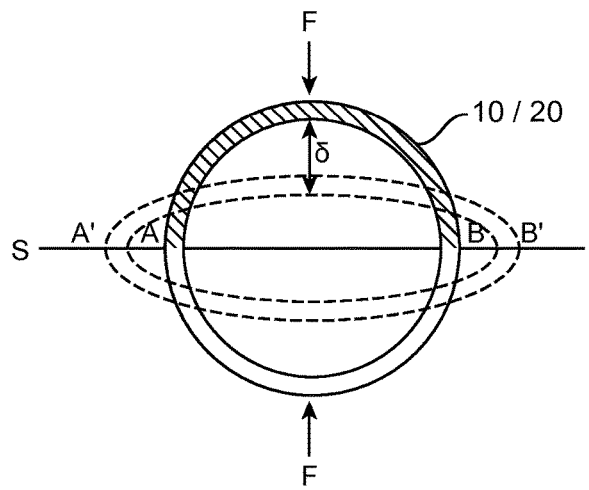
FIGS. 12A, 12B and 12C are diagrams describing a relationship between crush recoverability and wall thickness for a scaffold.
Figure 12B:
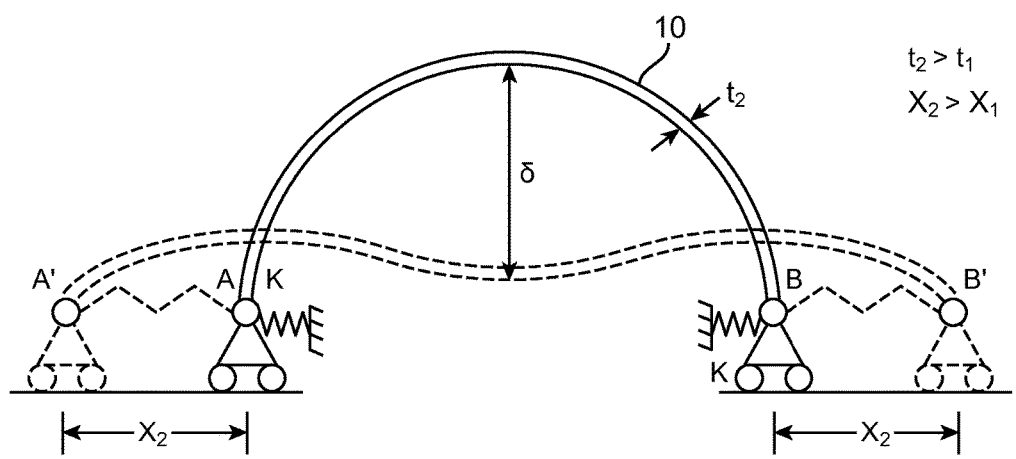
Figure 12C:
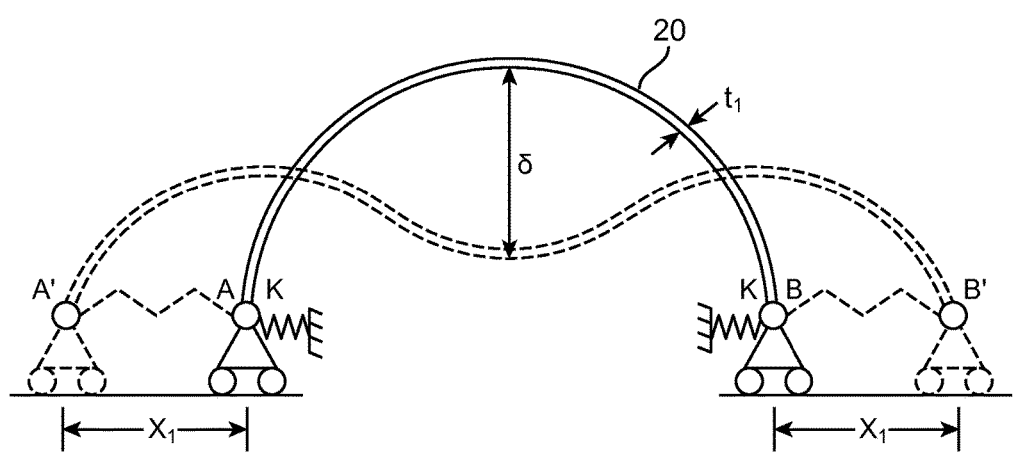

The diagrams drawn in FIGS. 12A, 12B and 12C are offered to assist with explaining a relationship between wall thicknesses and crush recoverability. FIG. 12A shows a cross-section of a scaffold in its un-deformed (unloaded) state and deformed state when subjected to a pinching load (drawn in phantom). The ends of the scaffold designated by "S" and "S'" refer to regions with the highest strain energy, as one can appreciate by the high degree of curvature in these areas when the scaffold is under the pinching load. If the scaffold will not recover or have reduction in recovery from the pinching load (F), it will be because in these regions the material has yielded, which precludes or reduces recovery back to the pre-crush diameter. The equal and opposite crushing forces in force F in FIG. 12A deflect the scaffold height from its un-deformed height, i.e., the scaffold diameter, to a deformed height as indicated by δ. The region of the scaffold that will contain the highest degree of strain energy when the crushing force F is being applied is near the axis of symmetry for the deformed shape, which is shown in phantom. In the following discussion, the load reaction or material stress/strain state at the scaffold regions S and S' will be expressed in terms of the strain energy.

FIGS. 12B and 12C are simplified models of the loaded structure intended to illustrate the effects on the strain energy in region S when the scaffold has different wall thickness. Essentially, the model attempts to exploit the symmetry of the deformed shape in FIG. 12A to construct a linear stress-strain representation at region S in terms of a spring have a spring constant K. Accordingly, the scaffold properties are modeled as arcs 10/20 (½ of a hoop or ring) or half-cylinder shells supported at the ends. The arc cannot displace downward (Y-direction) when the enforced displacement 6 is applied, which is believed acceptable as a boundary condition due to the symmetry in FIG. 12A. Movement in the x-direction is restrained by the spring having spring constant K. The hemispherical arc 10 in FIG. 12C has a thickness $t_1$ and the hemispherical arc 20 in FIG. 12B has a thickness of $t_2 \gg t_1$.

As the pinching load is applied in FIGS. 12B and 12C, the arcs 10 and 20 are deformed (as shown in phantom). This is modeled by an enforced displacement of the arcs 10/20 at their center by about the amount delta (δ) as in FIG. 12A.

The arc 10 deforms less than arc 20, however, in terms of its curvature when the enforced displacement is applied, because its flexural rigidity is higher than arc 20. Since the curvature is less changed in arc 10, more of the % strain energy resulting from the enforced displacement will be carried by the spring at the ends, where the spring force is restraining outward movement at S. For arc 20 more % strain energy is carried in the arc, as the greater changes of curvature are intended to show, as opposed to the spring restraining movement at the ends.

Consequently, for a given applied force the % strain energy at the ends will be greater for arc 10, since the flexural rigidity of the arc 10 is greater than the arc 20. This is depicted by the displacement of the spring ($x_2 > x_1$). The % strain energy in the spring restraining arc 20 (i.e., ½ $K(x_2)^2$/(total strain energy in arc 20)×100) is greater than the % strain energy in the arc 10 restraining spring (i.e., ½ $K(x_1)^2$/(total strain energy in arc 10)×100). From this example, therefore, one can gain a basic appreciation for the relationship between wall thicknesses and crush recoverability.

In a preferred embodiment it was found that for a 9 mm scaffold pre-crimp diameter a wall thickness of between 0.008" and 0.014", or more narrowly 0.008" and 0.011" provided the desired pinching stiffness while retaining 50% crush recoverability. More generally, it was found that a ratio of pre-crimp (or tube) diameter to wall thickness of between about 30 and 60, or between about 20 and 45 provided 50% crush recoverability while exhibiting a satisfactory pinching stiffness and radial stiffness. And in some embodiments it was found that a ratio of inflated diameter to wall thickness of between about 25 and 50, or between about 20 and 35 provided 50% crush recoverability while exhibiting a satisfactory pinching stiffness and radial stiffness.

Wall thickness increases for increasing pinching stiffness may also be limited to maintain the desired crimped profile. As the wall thickness is increased, the minimum profile of the crimped scaffold can increase. It was found, therefore, that a wall thickness may be limited both by the adverse effects it can have on crush recoverability, as just explained, as well as an undesired increase in crimped profile.

Testing

Provided below are results from various tests conducted on scaffolds and stents for purposes of measuring different mechanical properties and making comparisons between the properties of the stents and scaffolds. The stents used in the tests were the Cordis® S.M.A.R.T.® CONTROL® Iliac self-expanding stent (8×40 mm) ("Control stent"), the REMEDY Stent (6×40 mm) by Igaki-Tamai ("Igaki-Tamai stent"), and the Omnilink Elite® stent (6×40 mm).

The data presented in Tables 2-6 for the scaffolds V2, V23 and V59 are for scaffolds having the properties listed in Tables 6A and 6B, respectively. The scaffolds were crimped to a delivery balloon, then expanded to their inflated diameter using a process similar to the process described at paragraphs [0071]-[0091] of U.S. application Ser. No. 12/861,719.

The data presented in Tables 2-6 refer to scaffolds and stent properties after they were expanded by their delivery balloons. For each of the tests reported in Tables 2-6, infra, unless stated otherwise the statistic is a mean value.

Table 2 presents data showing the percentage of crush recovery for various scaffold compared with other types of stents. The scaffolds and stents were crushed using a pair of opposed flat metal plates moved together to crush or pinch the stents and scaffold by the respective amounts shown in the tables. The test was conducted at 20 degrees Celsius.

Table 2 compares the crush-recoverability of the V2, V23 and V59 scaffold to the Igaki-Tamai stent and Omnilink Elite® (6 mm outer diameter and 40 mm length) balloon expandable stent. The crush period was brief (about 0 seconds).

TABLE 2

Approximate crush recovery using flat plate test at 20 Deg. Celsius (as percentage of starting diameter, measured 12 hours following crush)

| Stent/scaffold type | when crushed to 18% of starting diameter | when crushed to 33% of starting diameter | when crushed to 50% of starting diameter | when crushed to 65% of starting diameter |
| --- | --- | --- | --- | --- |
| V23 (.008" wall thickness) | 99% | 96% | 89% | 79% |
| V23 (.014" wall thickness) | 99% | 93% | 84% | 73% |
| V59 (.011" wall thickness) | 99% | 96% | 88% | 80% |
| Igaki-Tamai | 99% | 94% | 88% | 79% |
| Omnilink Elite(R) | 93% | 80% | 65% | 49% |

As can be seen in the results there is a dramatic difference between the V2, V23 and V59 crush recovery compared with the Omnilink Elite® coronary stent. The best results are achieved by the V23 (0.008" wall thickness) and V59 scaffold when taking into consideration the radial strength and stiffness properties of these scaffold compared with the Igaki-Tamai stent (see Table 5).

Table 3 compares the crush recovery behavior for a V23 scaffold with 0.008" wall thickness (FIG. 6A) following a 50% crush. The data shows the percent crush recovery of the V23 scaffold following a brief (approximately 0 seconds), 1 minute and 5 minute crush at 50% of the starting diameter.

TABLE 3

Approximate crush recovery of V23 (.008" wall thickness) using flat plate test at 20 Deg. Celsius (as percentage of starting diameter, measured 24 hours following crush)

| Crush duration | when crushed to 25% of starting diameter | when crushed to 50% of starting diameter |
| --- | --- | --- |
| 0 second crush | 100% | 99% |
| 1 minute crush | 99% | 86% |
| 5 minute crush | 92% | 83% |

Figure 13:
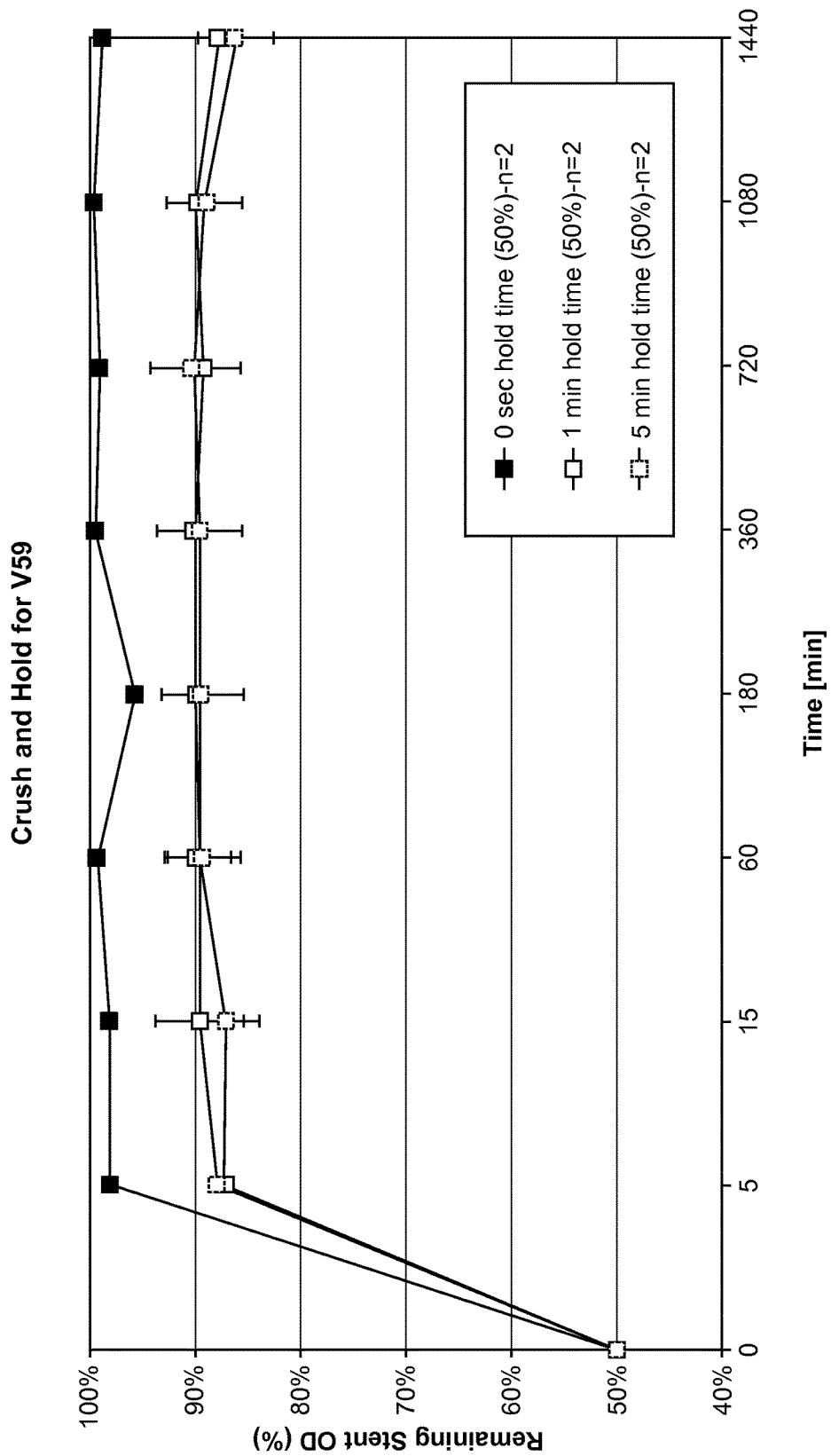
FIG. 13 is a plot showing the crush-recovery for a scaffold after a 50% crush. The plot shows the percentage recovered over a 24 hour period following a brief, 1 minute and 5 minute crush at 50%.

FIG. 13 shows the crush recovery properties for the V59 scaffold when crushed to 50% of its starting diameter over a 24 hour period following removal of the flat plates. There are three plots shown corresponding to the recovery of the scaffold following a 0 second, 1 minute and 5 minute crush duration. The scaffold diameter was measured at different time points up to 24 hours after the flat plates were withdrawn. As can be seen in these plots, most of the recovery occurs within about 5 minutes after the flat plates are withdrawn. It is contemplated, therefore, that an about 90% crush recovery is possible for longer periods of crush, e.g., 10 minutes, ½ hour or one hour, for scaffold constructed according to the disclosure.

When the pinching or crushing force is applied for only a brief period (as indicated by "0 sec hold time (50%)" in FIG. 13) tests indicate a recovery to about 95-99% of its initial diameter. When the force is held for 1 minute or 5 minute, tests indicate the recoverability is less. In the example of FIG. 13, it was found that the scaffold recovered to about 90% of its initial diameter. The 1 minute and 5 minute time periods being about the same suggests that any effects of the visco-elastic material succumbing to a plastic or irrecoverable strain when in a loaded state has mostly occurred.

In accordance with the disclosure, a crush-recoverable polymer scaffold (having adequate strength and stiffness properties, e.g., the stiffness and strength properties of the scaffold in Table 4, infra) has a greater than about 90% crush recoverability when crushed to about 33% of its starting diameter, and a greater than about 80% crush recoverability when crushed to about 50% of its starting diameter following an incidental crushing event (e.g., less than one minute); a crush-recoverable polymer scaffold has a greater than about 90% crush recoverability when crushed to about 25% of its starting diameter, and a greater than about 80% crush recoverability when crushed to about 50% of its starting diameter for longer duration crush periods (e.g., between about 1 minute and five minutes, or longer than about 5 minutes).

An acute recoil problem was observed. In one example, a scaffold was formed from a 7 mm deformed tube having a 0.008" wall thickness. When the scaffold was balloon deployed to 6.5 mm, the scaffold recoiled to about 5.8 mm. To address this problem, the scaffold was formed from larger tubes of 8 mm, 9 mm and 10 mm. It was found that a larger pre-crimp diameter relative to the intended inflated diameter exhibited much less recoil when deployed to 6.5 mm. It is believed that the memory of the material, formed when the deformed tube was made, reduced the acute recoil.

A starting tube diameter of 10 mm, for example, for a scaffold having a 7.4 mm inflated diameter should exhibit less recoil than, say, a 8 mm tube, however, this larger diameter size introduced other problems which discouraged the use of a larger tube size. Due to the larger diameter it became difficult, if not infeasible to reduce the diameter during crimping to the desired crimped diameter of about 2 mm. Since there is more material and a greater diameter reduction, there is less space available to reduce the diameter. As such, when the starting diameter exceeds a threshold, it becomes infeasible to maintain the desired crimped profile. It was found that a 9 mm tube size produced acceptable results in that there was less recoil and a crimped profile of about 2 mm could still be obtained.

An excessive starting diameter can introduce other problems during deployment. First, when the diameter reduction from starting diameter to crimped diameter is too great, the local stresses in the scaffold hinge elements, crowns or troughs correspondingly increase. Since the polymer material tends to be brittle, the concern is with cracking or fracture of struts if stress levels are excessive. It was found that the diameter 9 mm starting diameter scaffold (in combination with other scaffold dimensions) could be reduced down to 2 mm then expanded to the 7.4 mm inflated diameter without excessive cracking or fracture.

Table 4 compares the acute recoil observed in the V2, V23 and V59 scaffold of FIGS. 6A and 6B.

TABLE 4

Acute recoil comparisons

| Stent/scaffold type | percent recoil |
| --- | --- |
| V2 (.008" wall thickness) | 11.3% |
| V23 (.008" wall thickness) | 3.9% |
| V23 (.014" wall thickness) | 4.3% |
| V59 (.011" wall thickness) | 4.5% |

As discussed earlier, unlike a metal stent, a design for a polymer scaffold must take into consideration its fracture toughness both during crimping and when implanted within a vessel. For a scaffold located within a peripheral artery the types of loading encountered are in general more severe in terms of bending and axial loading than a coronary scaffold, in addition to the pinching or crush forces experienced by the scaffold, due to the scaffold's proximity to the surface of the skin, and/or its location within or near an appendage of the body. See e.g. Nikanorov, Alexander, M. D. et al., *Assessment of self-expanding Nitinol stent deformation after chronic implantation into the superficial femoral artery.*

As is known in the art, a scaffold designed to have increased radial stiffness and strength properties does not, generally speaking, also exhibit the fracture toughness needed for maintaining structural integrity. The need to have a peripherally implanted polymer scaffold with adequate fracture toughness refers both to the need to sustain relatively high degrees of strain in or between struts and links of the scaffold and to sustain repeated, cyclical loading events over a period of time, which refers to fatigue failure.

The methods of manufacture, discussed earlier, of the tube from which the scaffold is formed are intended to increase the inherent fracture toughness of the scaffold material. Additional measures may, however, be employed to reduce instances of fracture or crack propagation within the scaffold by reducing the stiffness of the scaffold in the links, or by adding additional hinge points or crown elements to the ring. Alternatively or in addition, pre-designated fracture points can be formed into the scaffold to prevent fracture or cracks from propagating in the more critical areas of the scaffold. Examples are provided.

As mentioned above, a peripherally implanted polymer scaffold is subjected, generally speaking, to a combination of radial compressive, pinching or crushing, bending and axial compression loads. Test results indicate that a majority of cracks can occur in the struts forming a ring, as opposed to the links connecting rings for a peripherally implanted polymer scaffold. Indeed, while bench data may suggest that a scaffold is quite capable of surviving cyclical radial, bending and axial loadings when implanted in a peripheral vessel, when the scaffold is in-vivo subjected to combined axial, flexural and radial loading in a peripheral vessel there is nonetheless unacceptable crack formation, fracture or significant weakening in radial strength.

With this in mind, alternative embodiments of a scaffold pattern seek to weaken, or make more flexible the scaffold in bending and axial compression without significantly affecting the radial strength or stiffness of the scaffold. By making links connecting rings more flexible, relative movement between a ring and its neighbor, which occurs when a scaffold is placed in bending or axial compression when rings are not axially aligned with each other, e.g., when the scaffold resides in a curved vessel, does not produce as a high a loading between the ring and its neighbor since the link tends to deflect more in response to the relative movement between the rings, rather than transfer the load directly from one ring to another.

Figure 14A:
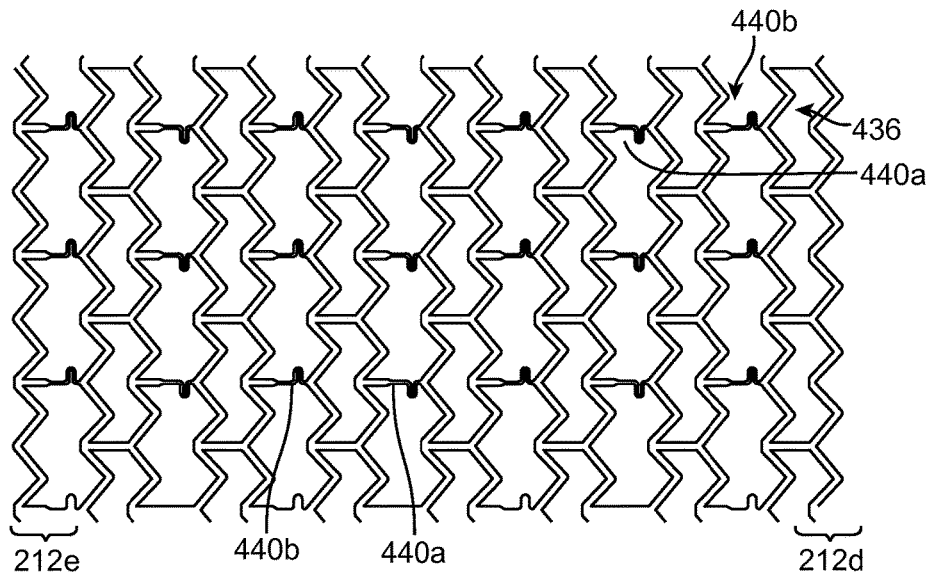
FIGS. 14A and 14B are partial planar views of a scaffold pattern according to an alternate embodiment of a scaffold including a first embodiment of a weakened or flexible link element connecting rings.
Figures 14B, 14C:
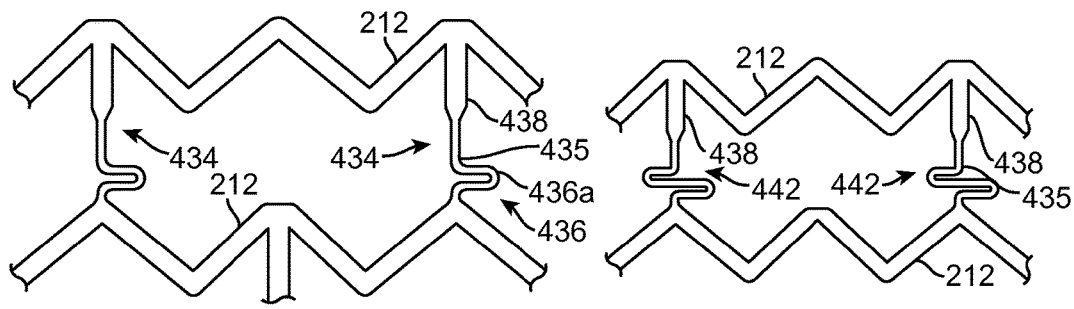
FIG. 14C is a second embodiment of a weakened or flexible link element connecting rings of the scaffold.

Referring to an alternative embodiment of pattern 200, a scaffold is constructed according to the pattern depicted in FIGS. 14A and 14B. Pattern 400 is similar to pattern 200 except that a link 434/440 connecting the rings 212 is modified to create greater flexibility in the scaffold in bending and axial compression (or tension). Referring to FIG. 14B, the link 434 includes a first portion 435 having a first moment of inertia in bending ($MOI_1$) nearest a Y-crown of a ring and a second portion 438 having a second moment of inertia ($MOI_2$) in bending nearest a W-crown of the neighboring ring, where $MOI_1 < MOI_2$. Additionally, a U-shaped portion 436 is formed in the portion 435 to create, in effect, a hinge or articulation point to reduce bending stiffness further. The U-shape portion 436 opens when the ring 212 rotates clockwise in FIG. 14B. As such, the link is very flexible in clockwise bending since the bending stiffness about the hinge 436a is very low. For counterclockwise rotation, the ends of the U-shaped portion abut, which in effect negates the effect of the hinge 436a.

To construct a scaffold that is equally flexible for both clockwise and counterclockwise bending of the scaffold, the U-shaped portions 434 may be removed so that the increased flexibility is provided solely by the reduced MOI portions of the links, such as by replacing the U-shaped portion 436 in FIG. 14B with a straight section having a reduced MOI. An alternative is depicted in FIG. 14A, which shows alternating inverted U-Links 440b and U-links 440a. When the scaffold is subject to a clockwise bending moment (i.e., ring 212d is displaced downwardly in FIG. 14A relative to ring 212e) the U-shaped portions of the U-links 440a act as hinge points. The "U" opens in response to the relative movement between the adjacent rings 212, whereas the inverted U-links 440b function, essentially, as straight sections since the ends of the inverted "U" will contact each other. Similarly, when the scaffold is subject to a counterclockwise bending moment (i.e., ring 212d is displaced upwardly in FIG. 14A relative to ring 212e) the inverted U-shaped portions of the inverted U-links 440b act as hinge points. The inverted "U" opens in response to the relative movement between the adjacent rings 212, whereas the U-links 440a function, essentially, as straight sections since the ends of the "U" each other when the scaffold deflects.

In another embodiment a reduced MOI may be achieved by increasing the distance between each ring, or preferably every other ring. For example, the distance between ring 212a and 212b in FIG. 2 may be increased (while the distance between rings 212c, 212b remains the same). In this example, a link connecting rings 212a and 212b can have the same MOI as the link connecting rings 212b and 212c yet the former link will be less stiff in bending since its length is longer than the later link.

In another alternative, the pattern 400 includes a link 442 with opposing "U" shaped portions or an "S" portion, as depicted in FIG. 14C. The S-link 442 has the $MOI_1$ and $MOI_2$ as before, except that the portion 435 of the link 442 has two hinge points, 444a and 444b, instead of the one in FIG. 14B. With this arrangement, the link 442 provides a hinge point to increase bending flexibility for both clockwise and counterclockwise bending. As such, for a pattern 400 having links 442 the same link 442 may be used everywhere to achieve greater bending flexibility for both clockwise and counterclockwise bending.

Figure 14D:
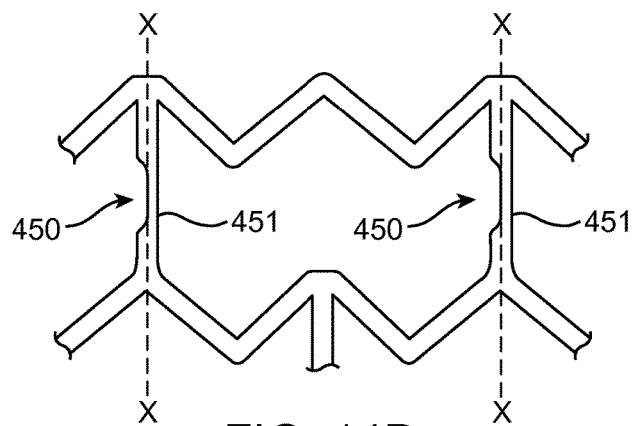
FIGS. 14D and 14F shows an alternate embodiment of a weakened portion of a link connecting rings.
Figure 14E:
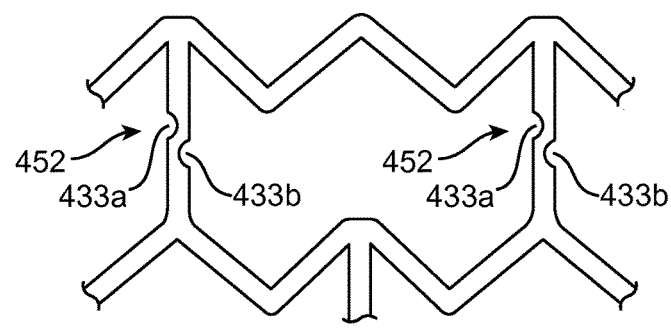
FIG. 14E shows an example of a link structure where voids are formed in the link to create a point of fracture for the link at the voids.
Figure 14F:
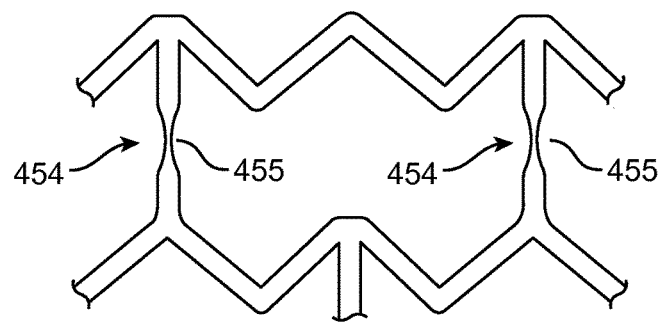

FIGS. 14D through 14F illustrate additional embodiments of a link 442 extending between and connecting the Y and W crowns. These examples show links having variable MOIs, either by shaping the link as the pattern is cut from a tube or by modifying the link after the scaffold has been cut from the tube.

FIGS. 14D and 14F show links 450 and 454, respectively, formed to have a section having a lower MOI than sections located adjacent the connecting crowns. In the case of link 450 the section 451 having the low MOI is offset from, or non-symmetric about the neutral axis "X" in bending for the sections adjacent crowns. In the case of link 454 the section 455 is symmetric about the neutral axis for the sections adjacent the crowns. This symmetry/non-symmetry contrast for sections 451 and 452 may also be described with respect to an axis of symmetry for the crowns. Thus, for an axis of symmetry "X" for a Y-crown (210) or W crown (209), which can be readily identified from the figures, section 451 is asymmetric about the X axis, whereas the necked section 455 of the link 454 is symmetric about this axis, which may be considered a crown axis.

FIG. 14E illustrates an example where material between the ends of the links are removed to form two curved voids 433a, 433b in the link 452. These embodiments may function in a similar manner as the "S" link discussed earlier. According to this embodiment, a pre-designated fracture point (to fail before the rings fail) is between the voids 433a, 433b. The material forming the voids 433a, 433b may be about the same so as to retain symmetry about the axis X, or they may be a different size to cause the axis of symmetry to not be co-linear with this axis, as in the case of FIG. 14D. The selection of the void size is based on the desired fracture characteristics relative to the ring and whether it is preferred to have a link less stiff for bending in the clockwise or counterclockwise direction, as explained earlier.

Figure 15:
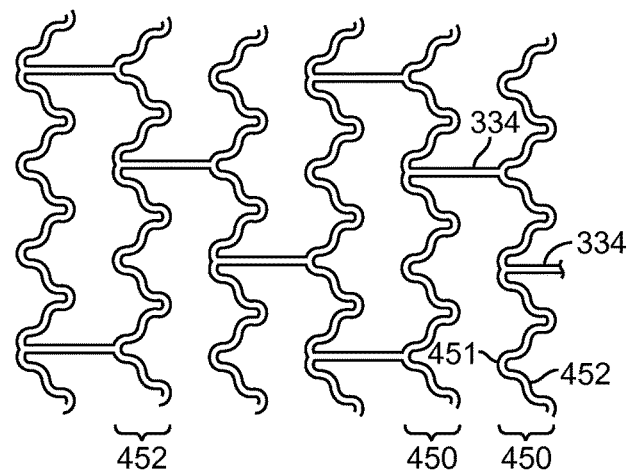
FIG. 15 is a partial planar view of a scaffold pattern according to an alternate ring structure for a scaffold where the ring structure has curved struts extending between crowns.

In another embodiment, greater fatigue and/or fracture toughness may be achieved by modifying the struts of the ring. Referring to FIG. 15, there is shown a pattern similar to pattern 300 except that the rings 450 are formed by curved struts 452 connected at crowns 451. In this example the struts 452 have a shape approximating one sinusoidal period. By replacing the straight struts of FIG. 4 with sinusoidal struts there is essentially additional hinge points created in the ring.

The number of modified link elements, as discussed in connection with FIGS. 14A-14C may be between 5-100% of the links used to connect rings of the scaffold. The U-links or S-links as described may be placed between each ring, or may be placed between every-other ring pair. Additionally, the links may be modified by having their MOI reduced without U or S links. Additionally, one or more connecting links can be removed. When there are less connecting links, e.g., 3 verses 4, the scaffold should generally have a reduced bending and axial stiffness (assuming everything else in the scaffold is unchanged). However, as mentioned earlier, the end-to-end or overall effects on performance, reproducibility, quality control and production capacity for such change in a scaffold is, unfortunately, not as easy to predict as in the case of a metal stent.

In another aspect of the disclosure, there is a scaffold pattern having rings formed by closed cells. Each of the closed cells of a ring share a link element that connects the longitudinally-spaced and circumferentially extending strut portions of the closed cell. Each of these closed cell rings are interconnected by a connecting link e.g., links, 434, 442, 450, 452 or 454, having a reduced bending moment of inertia (MOI) to reduce the flexural rigidity of the structure connecting the closed cell rings. Alternatively, the connecting link can include a pre-designated fracture point, such as by forming an abrupt change in geometry near a high strain region. Returning again to FIG. 14A, the scaffold pattern depicted has links 440a connected to each closed cell ring. For each closed cell 204 there is a first and second connecting link, which are co-linear with each other. The first link has a $MOI_1$ disposed adjacent the crown and the second link has a $MOI_2$ disposed distal the crown to produce the pattern shown in FIG. 14A. Alternatively the links connecting the closed cell rings may have the $MOI_1$ disposed equidistant from the interconnected closed cell rings.

According to an additional aspect of the disclosure, there is a scaffold that includes pre-designated fracture points in the links connecting rings. The fracture points are intended to relive the inter-ring loading through crack formation in the links connecting rings. Since the loading on a crown is reduced or eliminated when there is sufficient crack propagation through the link (load cannot transfer across a crack), by including a pre-designated crack location, one may maintain the integrity of the ring structure at the expense of the links, e.g., links 450, 452, in the event in-vivo loading exceeds the design, particularly with respect to fatigue loading. According to this aspect of the disclosure a link has a reduced MOI near a high strain region and includes an abrupt geometry change, e.g., about 90 degrees mid-span. These pre-designated fracture point in the scaffold may extend between closed cell rings, as described above, or between each ring strut.

Cracking/fracture problems are also observed as a consequence of irregular crimping and/or deployment of the scaffold. Irregular deployment is problematic, not only from the viewpoint of the scaffold not being able to provide a uniform radial support for a vessel, but also from the viewpoint of crack propagation, fracture and yielding of structure resulting in loss of strength and/or stiffness in vivo. Examples of irregular deployment include crowns being expanded beyond their design angles and in extreme cases, flipping or buckling of crowns during deployment or crimping. These problems were observed during crimping process and during deployment, examples of which are described in greater detail in U.S. application Ser. No. 12/861,719.

Pattern 300 may be susceptible to more of these types of problems than pattern 200. The links of the pattern provide less support for the ring struts forming the V segment of the W-V closed cell 304, as compared to pattern 200. It is believed that the w-shaped closed cell 204 was more capable of deploying without irregularities, such as flipping, due to its symmetry. The asymmetric loading inherent in the W-V cell 304 was more susceptible to buckling problems during crimping or deployment. These potential problems, however, should they arise, may be addressed by adopting modifications to the crimping process.

For example, a scaffold having a diameter of 7 mm and asymmetric closed cells (pattern 300) was crimped then deployed without any flipping of struts observed. A second scaffold of 9 mm diameter was then crimped to a balloon and deployed. This scaffold had the same pattern 300 as the 7 mm scaffold. The strut or crown angle was increased by the ratio of the diameters, i.e., increased by a factor of 9/7, to compensate for the change in radial stiffness resulting from the increased diameter. When the 9 mm scaffold was crimped, however, flipping occurred in the scaffold struts (primarily in the V section of the W-V closed cell). To correct this problem the W closed cell (pattern 200) was tested. This modification helped to reduce instances of flipped struts. Surprisingly, the same irregular crimping/deployment problems have not been observed for the comparable metal stent having a W-V closed cell pattern. It was concluded, therefore, that the flipping problem (in particular) is a phenomenon unique to a polymer scaffold.

To avoid flipping phenomena, should it occur in a metal stent, one might consider simply adjusting the moment of inertia of a strut to prevent out of plane (outside of the arcuate, abluminal surface) deflection of a strut. However, as noted earlier, the polymer material introduces constraints or limitations that are not present with a metallic material. In the case of minimizing undesired motion of a strut by modifying bending inertia properties of the strut one needs to be mindful that polymer struts must, generally speaking, be thicker and/or wider than the equivalent metal strut. This means there is less space available between adjacent struts and already higher wall thicknesses than the metal counterpart. This problem of space is further compounded for embodiments that form a polymer scaffold from a tube that is the deployed, or larger than deployed size. It is desirable to have the scaffold reduced in diameter during crimping for passage to the same vessel sites as in the case of the metal stent. Thus, the delivery profile for the crimped scaffold should be about the same as the metal stent.

A metal stent may be cut from a tube that is between the deployed and crimped diameters. As such, the spacing between struts is greater and the stent is more easily compressed on the balloon because the stent pre-crimp has a diameter closer to the crimped diameter. A polymer scaffold, in contrast, may be cut from a diameter tube equal to or greater than the deployed state. This means there is more volume of material that must be packed into the delivery profile for a polymer scaffold. A polymer scaffold, therefore, has more restraints imposed on it, driven by the crimped profile and starting tube diameter, that limits design options on strut width or thickness.

A well known design requirement for a vessel supporting prosthesis, whether a stent or scaffold, is its ability to maintain a desired lumen diameter due to the inward radial forces of the lumen walls including the expected in vivo radial forces imparted by contractions of the blood vessel. Referring to the examples in FIGS. 6A-6B, the radial stiffness and radial strength of the scaffold is influenced by the width of struts, crown radii and angles, length of ring struts extending between crowns and valleys, the number of crowns and the wall thickness (thickness 235, FIG. 3) of the scaffold. The latter parameter (wall thickness) influences the pinching stiffness, as explained earlier. During the design process, therefore, this parameter was altered to affect pinching stiffness and crush recoverability, although it also has an effect on radial stiffness. In order to affect the radial stiffness, one or more of the foregoing parameters (crown angle, crown radius, ring strut length, crown number, and strut width) may be varied to increase or decrease the radial stiffness.

To take one example, when it was found that a 7 mm scaffold's recoil problem could be overcome by increasing the starting tube diameter to 8 mm, 9 mm or perhaps even 10 mm, an initial approximation to the corresponding changes to the scaffold pattern dimensions involved increasing characteristics such as ring strut length, crown angle and link by the ratio of the diameters, e.g., 8/7 when increasing OD from 7 mm to 8 mm. However, this rough approximation was found to be insufficient in retaining other desired properties, such as crush recoverability. Thus, further refinements were needed.

The relationships between radial stiffness and above mentioned parameters are well known. However, the relationship of these stiffness-altering parameters to crush recoverability of a balloon expandable stent, much less a balloon expandable scaffold is not well known, if known at all in the existing art. Accordingly, the design process required the constant comparison or evaluation among radial stiffness, pinching stiffness and crush recoverability (assuming the changes did not also introduce yield or fracture problems during crimping and deployment) when the stiffness parameters were altered to determine whether these and related scaffold properties could be improved upon without significant adverse effects to crush recoverability.

When varying these parameters to affect stiffness the following observations were made for a 9 crown and 8 crown scaffold. For a 9 crown pattern and 7-9 mm outer diameter an angle exceeding 115 degrees, while producing a high radial stiffness, also exhibited fracture problems when deployed and an unsatisfactory reduction in crush recoverability. Strut or crown angles found to produce acceptable results were between about 105 and 95 degrees. For a 8 crown scaffold a smaller angle than 115 degrees was preferred for the crown. For the 8 crown scaffold the angle is about less than 110 degrees. Generally speaking, the more crowns the more compliant becomes the scaffold radially and the higher the crown angle the less radially complaint becomes the scaffold.

Comparisons were made among mean radial strength (N/mm) and radial stiffness (N/mm) values after e-beam sterilization of a V2, V23 and V59 constructed scaffold (having the properties summarized in FIGS. 6A-6B) with the Control stent, Igaki-Tamai stent, and Absolute stent (8.5 mm outer diameter, 36 mm length). Table 5 summarizes the findings.

TABLE 5

Radial strength and stiffness comparisons

| Stent/scaffold type | Radial strength (sterilized) | Radial stiffness (sterilized) |
| --- | --- | --- |
| Cordis ® | 0.82 | 0.58 |
| Igaki-Tamai | 0.04 | 0.09 |
| Absolute 8.5 ProLL | 0.51 | 0.22 |
| V2 (.008" wall thickness) | 0.32 | 0.54 |
| V23 (.014" wall thickness) | 0.49 | 1.2 |
| V23 (.008" wall thickness) | 0.4 | 0.59 |
| V59 (.011" wall thickness) | 0.6 | 0.91 |

The V2, V23, and V59 had far superior strength and stiffness values over the Igaki-Tamai stent. The V23 with 0.014" had the highest radial stiffness. The V2, V23 and V59 strength and stiffness values were comparable to the self-expanding stent.

Comparisons were also made between the pinching stiffness of scaffold according to the disclosure. The values represent average values in units of N/mm based on three samples. The stiffness values were computed from the measured force required to crush the scaffold to ½ or 50% of its starting diameter, e.g., expanded or inflated diameter, using a flat plate test at 20 Deg Celsius.

TABLE 6

Pinching Stiffness

| Stent/scaffold type | average stiffness | standard deviation |
| --- | --- | --- |
| V2 (.008" wall thickness; 36 mm length) | 0.151 | .005 |
| V23 (.008" wall thickness; 38 mm length) | 0.202 | .004 |
| V23 (.014" wall thickness; 38 mm length) | 0.394 | .052 |
| V59 (.011" wall thickness; 36.5 mm length) | 0.537 | .037 |

According to one aspect of the disclosure a crush-recoverable scaffold has a ratios of pinching stiffness to radial stiffness of between about 4 to 1, 3 to 1, or more narrowly about 2 to 1; ratios of pinching stiffness to wall thickness of between about 10 to 70, or more narrowly 20 to 50, or still more narrowly between about 25 and 50; and ratios of scaffold inflated diameter to pinching stiffness of between about 15 and 60 or more narrowly between about 20 to 40.

According to another aspect of the disclosure a crush-recoverable scaffold has a desirable pinching stiffness to wall thickness ratio of 0.6-1.8 N/mm$^2$.

According to another aspect of the disclosure a crush-recoverable scaffold has a desirable pinching stiffness to wall thickness*tube diameter ratio of 0.08-0.18 N/mm$^3$.

Animal Studies

Two animal studies ("Study 1" and "Study 2") were conducted for the scaffolds described in FIGS. 6A-6B. The scaffolds were implanted into the iliofemoral artery of a healthy porcine model at 28, 90 and 180 days to evaluate the effectiveness of the polymer scaffold.

Study 1: compares the V2 with a Cordis® S.M.A.R.T.® CONTROL® Iliac self-expanding stent having an 8 mm outer diameter and a 40 mm length (hereinafter the "control stent"). Among the features of the implanted V2 and control stent investigated in the study was the degree of, and related complications caused by a chronic outward force effect of the implanted prostheses on the healthy artery at 28, 90 and 180 days following implantation.

Study 2: compares the V23-008 and V23-014 to determine the effect wall thickness has on scaffold performance, principally loss in lumen area, scaffold area and growth in neointimal thickness.

During the course of the studies the implanted prostheses was subject to various degrees of hip extension and flexion by the swine, which is believed to impose about 10-12% bending, and about 13-18% axial compression of the implanted scaffold and control stent during a maximum hip and knee flexion.

Figure 16:
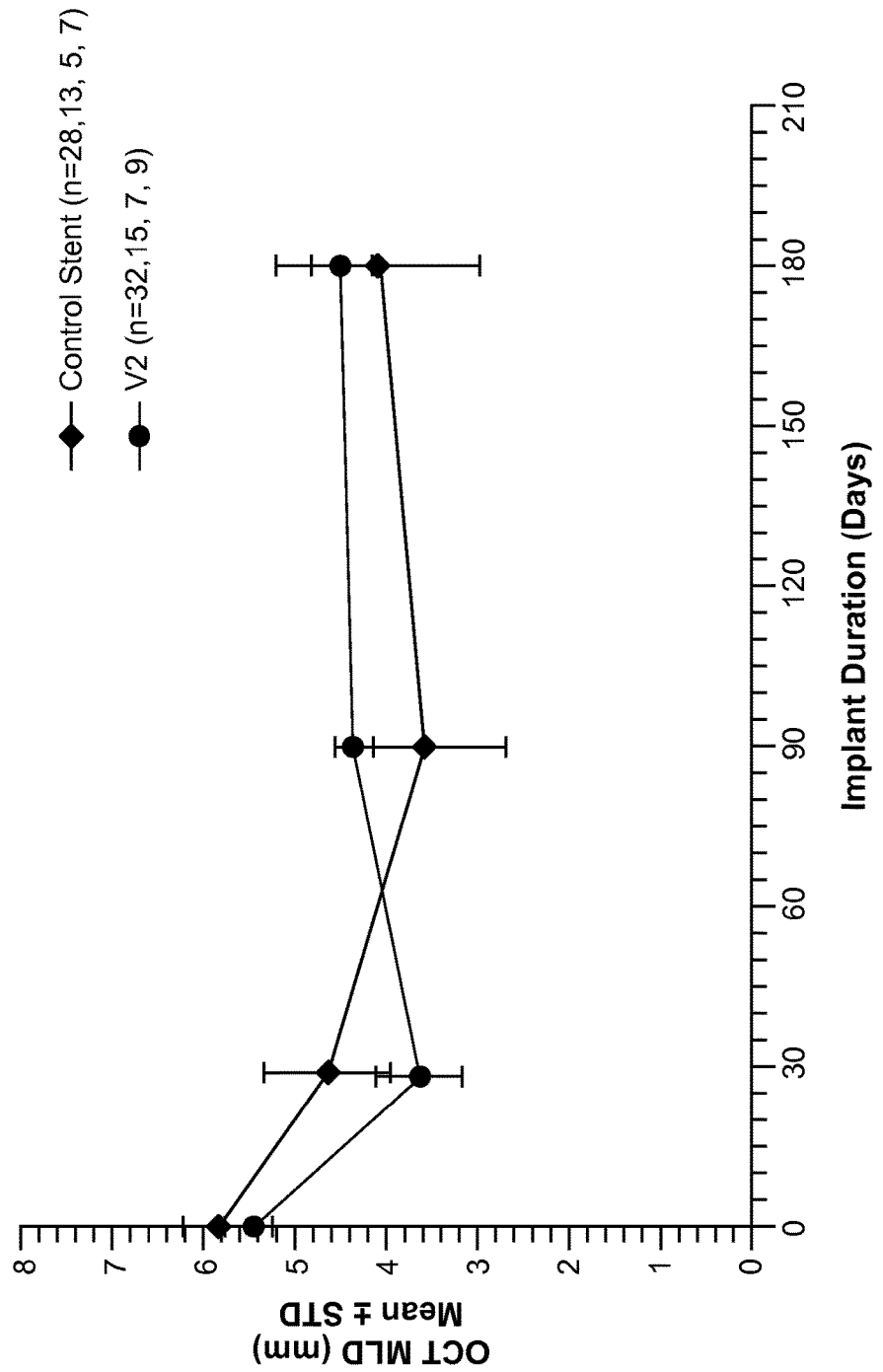
FIGS. 16-23 are plots showing results from a first animal study for an implanted scaffold at 30, 90 and 180 days following implantation. The scaffold performance is compared to a self-expanding metal stent implanted within the same animal.

FIG. 16 is a plot showing the mean minimal lumen diameter (MLD) of the artery for the control stent and scaffold as measured using optical coherence tomography (OCT). The measurements were taken after 28, 90 and 180 days. After 28 days, the scaffold average MLD was about 3.6 mm (15 samples) while the control stent mean MLD was about 4.7 mm (13 samples). After 90 days the scaffold mean MLD was about 4.4 mm (7 samples) and the control stent mean MLD was about 3.6 mm (5 samples). After 180 days the scaffold mean MLD was about 4.4 mm (9 samples) and the control stent mean MLD was about 4.0 mm (7 samples). The variance in mean MLD after 28, 90 and 180 days for the control stent was much larger than the variance in mean MLD for the scaffold.

Figure 17:
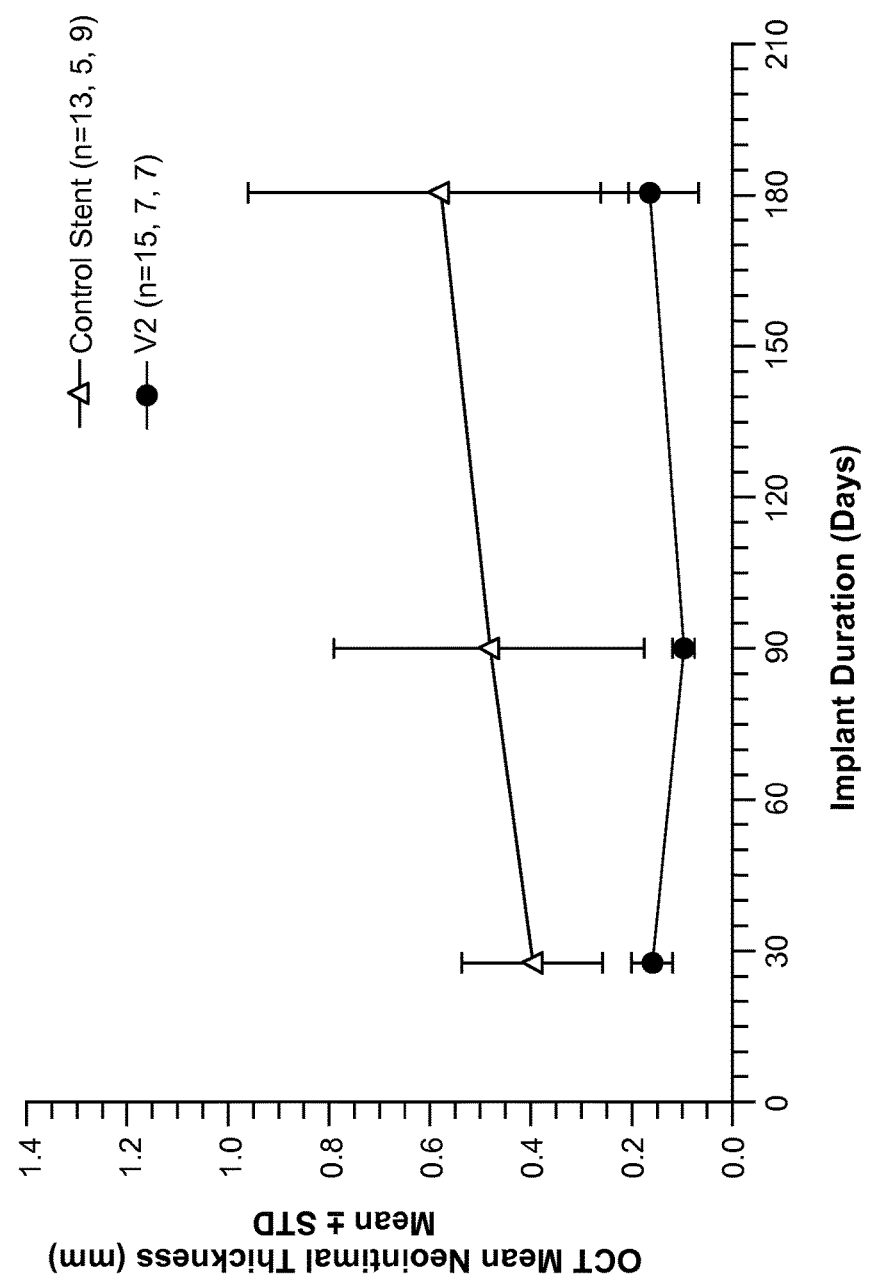

FIG. 17 shows the mean neointimal thickness (as measured by OCT) after 28, 90 and 180 days. At 28 days the mean control stent neointimal thickness was about 0.4 mm (15 samples) while the mean scaffold neointimal thickness was less than 0.2 mm (13 samples). At 90 days the mean neointimal thickness for the control stent had increased to about 0.43 (7 samples) whereas the mean neointimal thickness for the scaffold had decreased to about 0.1 mm (5 samples). At 180 days the control stent's mean neointimal thickness had increased to 0.55 mm whereas the scaffold mean neointimal thickness had increased to about 0.19 mm. At the 28, 90 and 180 days the variance in neointimal thickness for the control stent was much higher than for the scaffold. It should be noted that the PLLA scaffold included a drug coating to reduce tissue growth, whereas the control stent did not have a similar drug coating on it.

Figure 18:
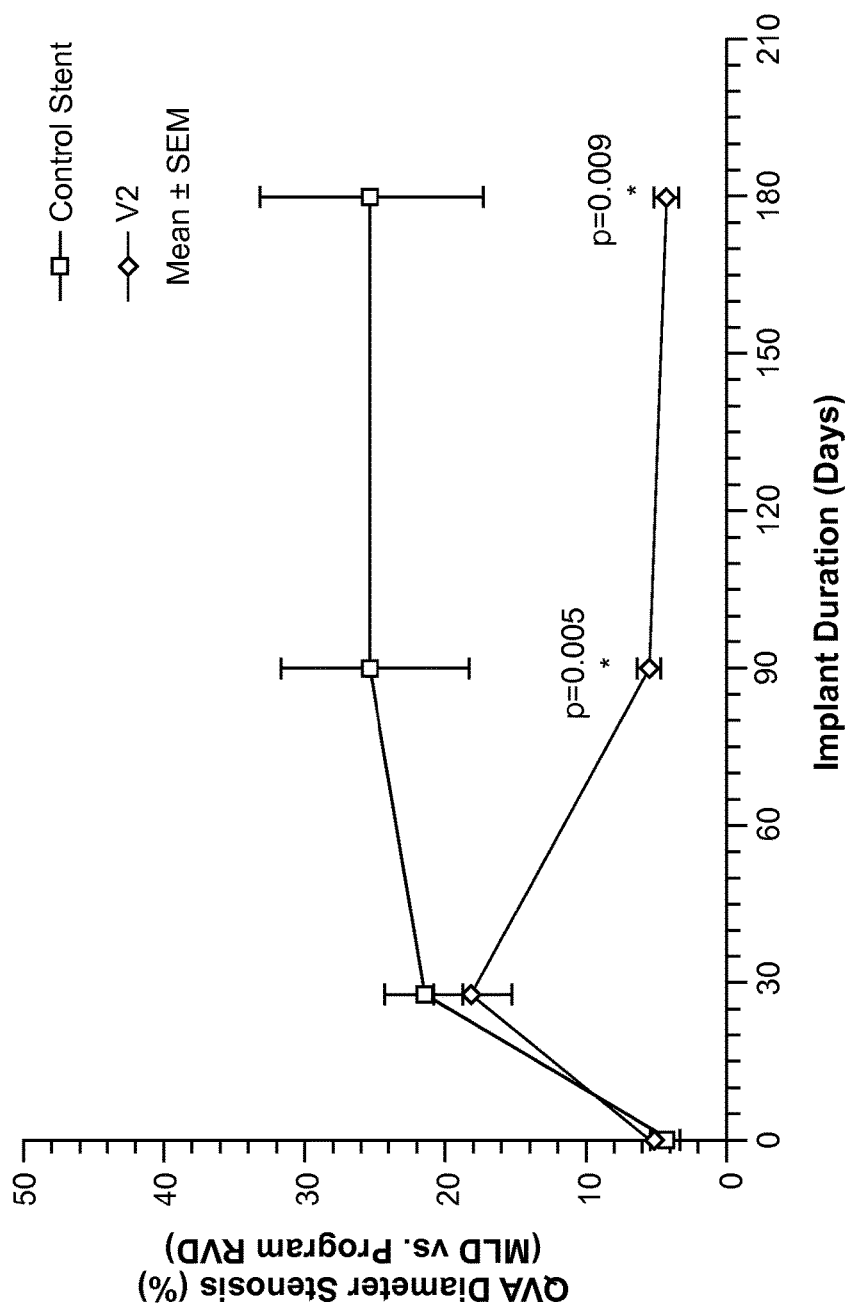

FIG. 18 shows the amount of stenosis measured after 28, 90 and 180 days using OCT. The amount of stenosis was about 22% and 18% for the control stent and scaffold, respectively, after 28 days. After 90 days the amount of stenosis for the control stent had increased to about 25% whereas the scaffold stenosis had decreased to about 5%. After 180 days the amount of stenosis for the control stent remained at about 25% whereas the scaffold stenosis had decreased to about 4%. The variance in stenosis for the control stent was far greater than the scaffold after 28, 90 and 180 days.

Figure 19:
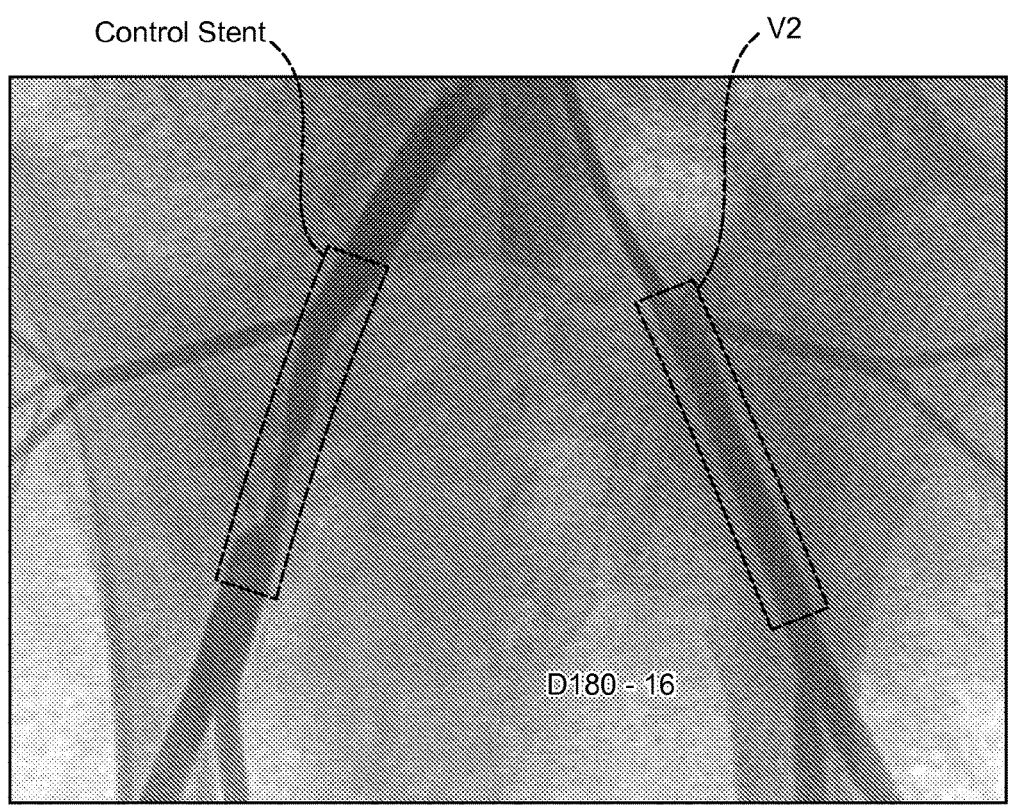

FIG. 19 shows angiography images of the implanted scaffold and control stent, respectively, taken 180 days after implantation. The dark areas indicate the size of the lumen where the prostheses were implanted. As can be appreciated from these images, the lumen in the vicinity of the control stent has narrowed considerably. It is believed the increase in neointimal thickness, reduced MLD and increased stenosis measured in the vicinity of the control stent, FIGS. 16, 17 and 18, respectively, are symptoms of the chronic outward force imposed on the artery by the self-expanding control stent.

Figure 20:
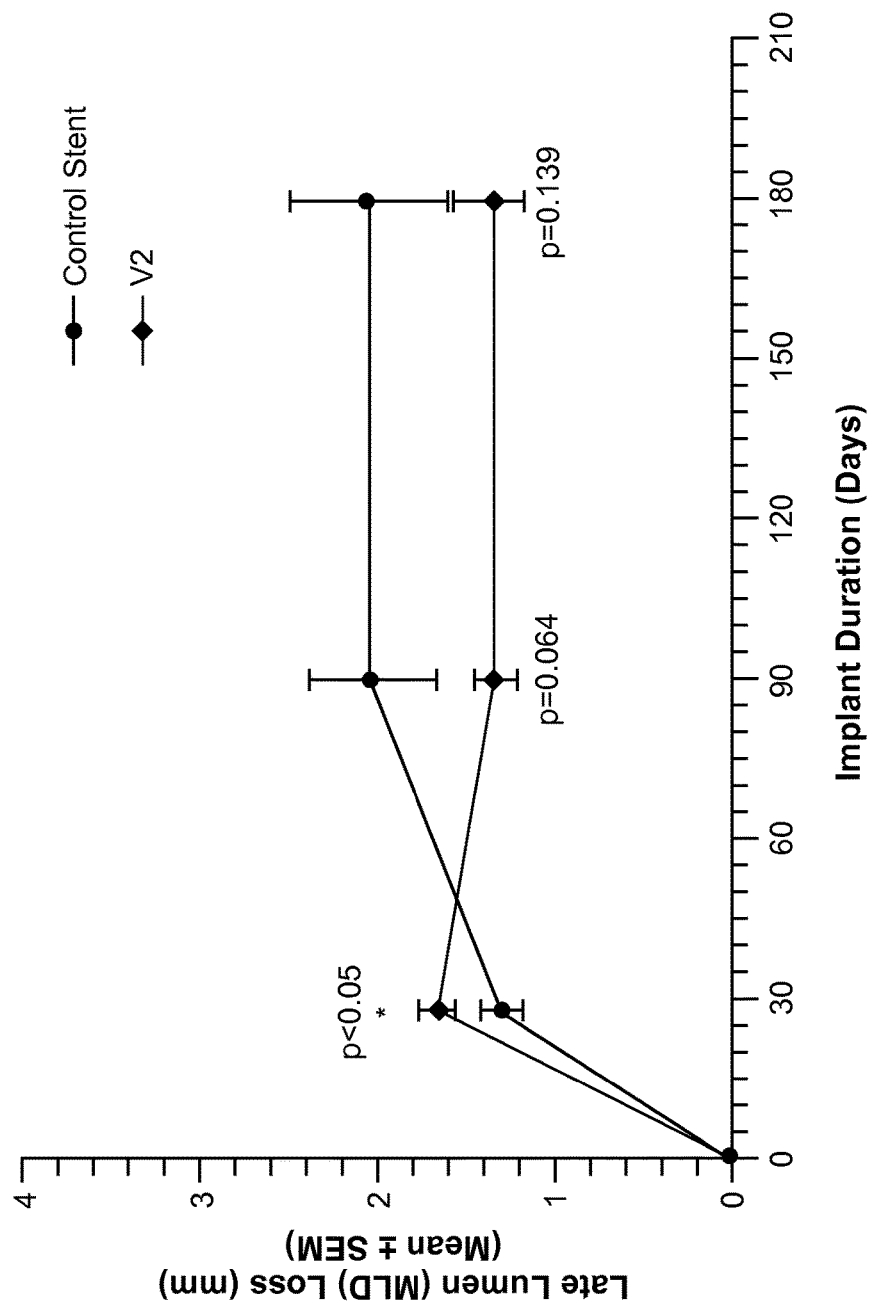
Figure 21:
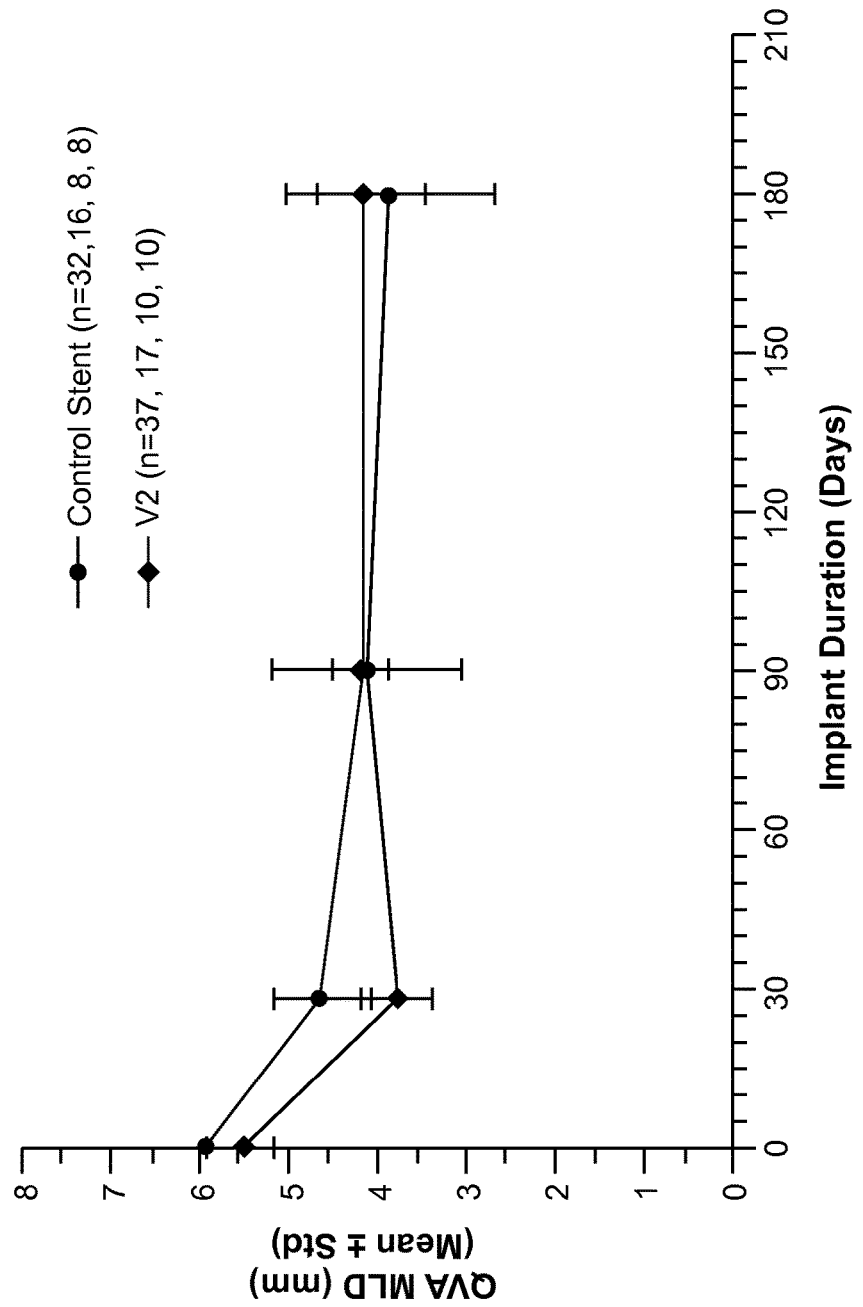

FIGS. 20 and 21 are plots at 28, 90 and 180 days using the QVA measurement technique (commonly used by physicians). FIG. 20 depicts the mean and variance late loss (loss in lumen diameter after implantation) for the control stent and scaffold. FIG. 21 shows the mean and variance for the MLD for the control stent and scaffold.

Figure 22:
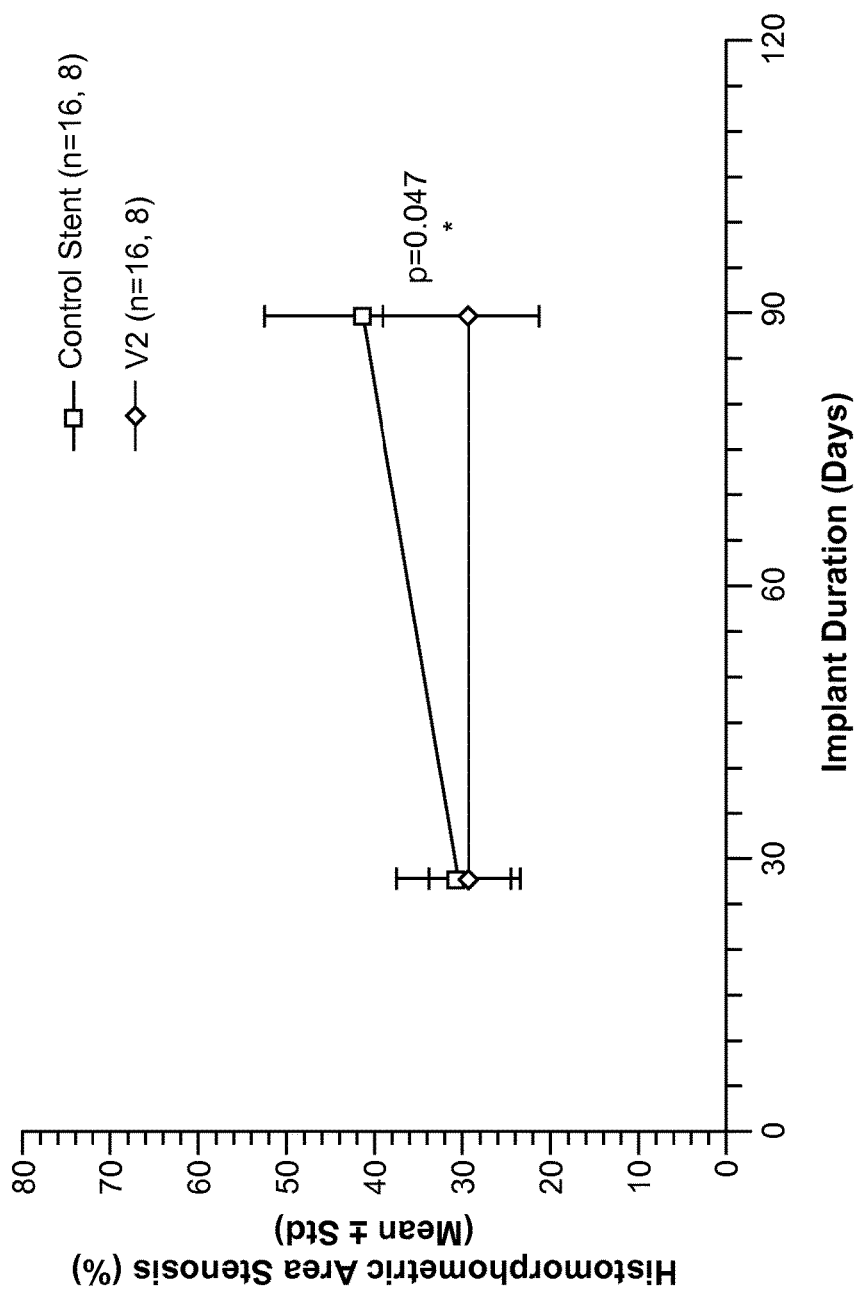
Figure 23:
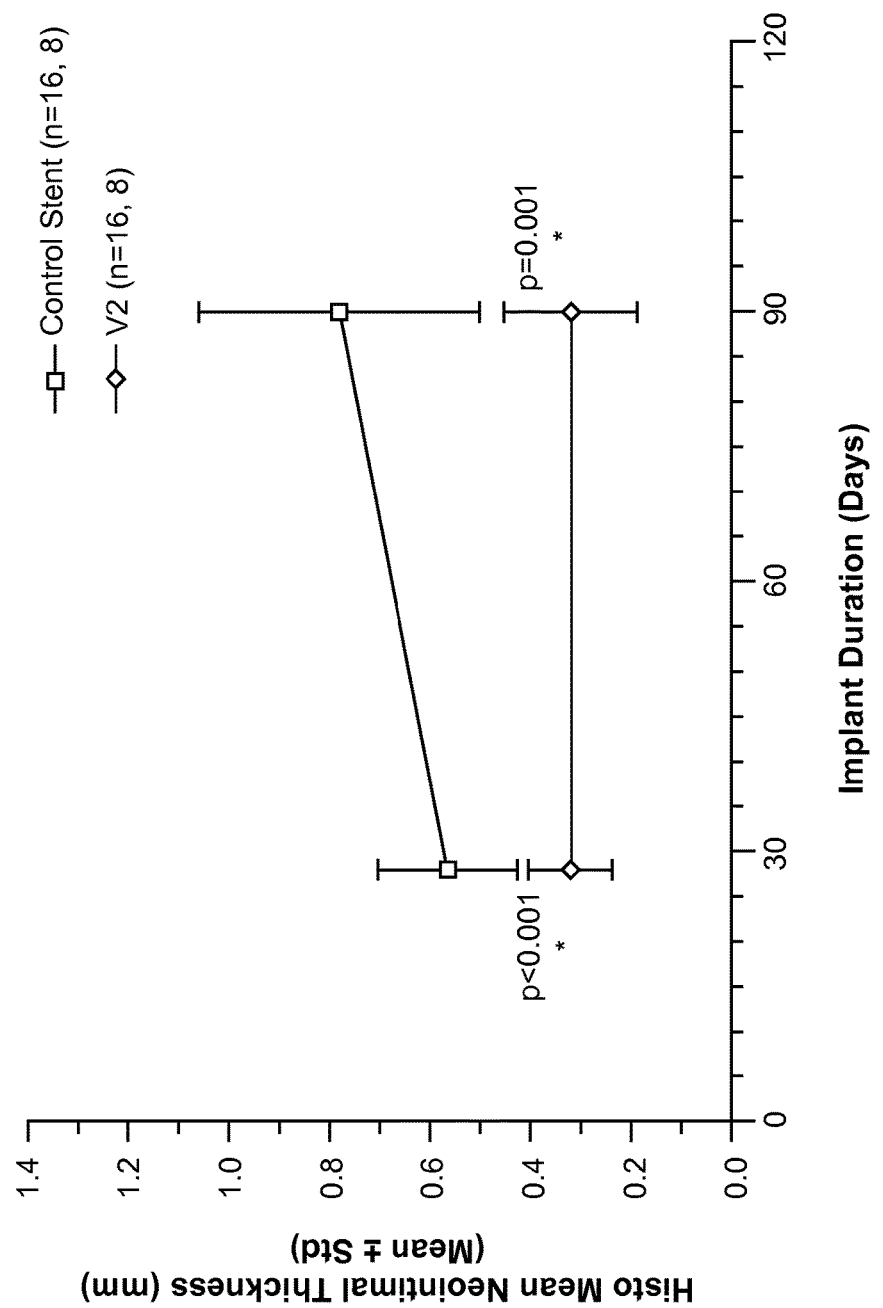

FIGS. 22 and 23 are plots at 28 and 90 days of the histomorphometric area stenosis and neointimal thickening by histomorphometry, respectively, for the control stent and V2 scaffold. Both these plots indicate a steady and less favorable increase in the area stenosis and neointimal growth whereas the area stenosis and neointimal growth for the scaffold was about constant and less than the control stent.

Figure 24:
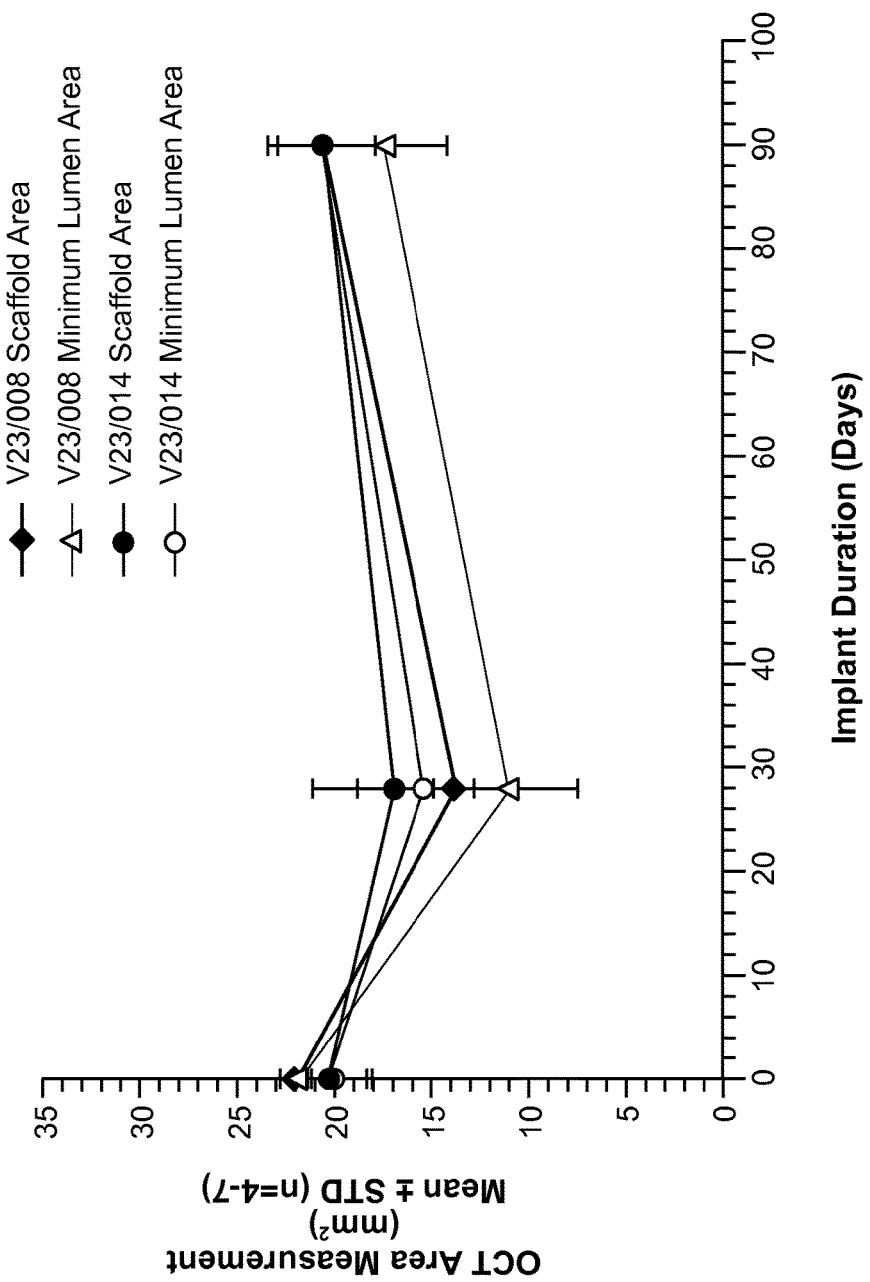
FIGS. 24-26 are plots showing results from a second animal study comparing the performance of scaffold having different wall thickness.
Figure 25:
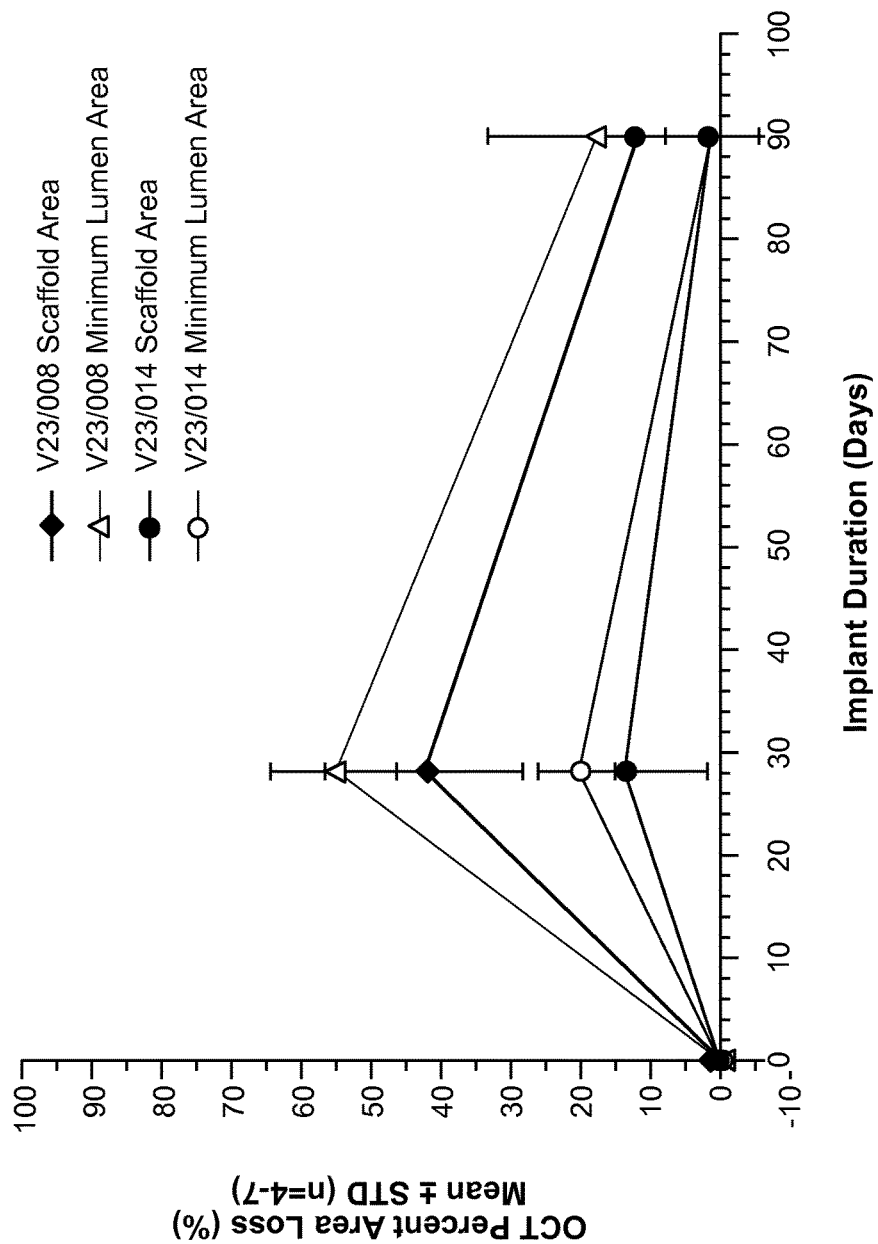
Figure 26:
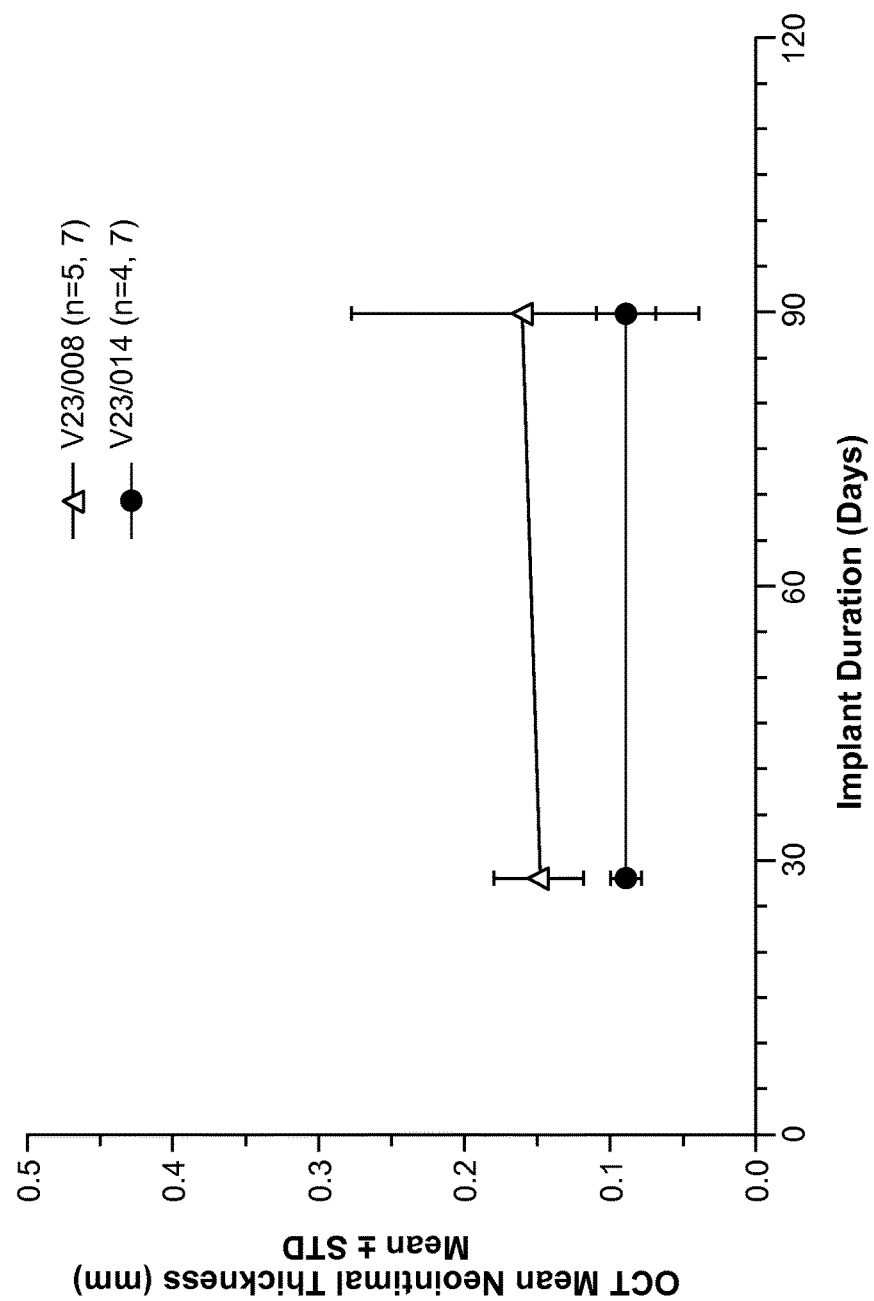

FIG. 24 compares the minimum lumen and minimum scaffold areas for the V23 having a 0.008" wall thickness ("V23/008") with the V23 having a 0.014" wall thickness ("v23/014") after 28 and 90 days. Both the minimum lumen area and minimum scaffold areas were higher for the V23 with a 0.014" wall thickness. FIG. 25 shows the lumen area loss after 28 and 90 days. The V23 with 0.014" wall thickness had less lumen area loss than the V23 with 0.008" wall thickness. Also, there was less variance among the samples for the V23 with 0.014" wall thickness. FIG. 26 shows the mean neointimal thickness between the V23 with 0.008" and 0.014" wall thickness. There was less tissue growth on the luminal surface of the scaffold when the 0.014" wall thickness was implanted.

The 30, 90 and 180 day animal studies comparing the control stent to the V2 scaffold indicate that the scaffold exhibits noticeably less problems associated with a chronic outward force as compared to the control stent. The 30 and 90 day study comparing a 0.008" and 0.014" wall thickness scaffold indicate there is more likely a reduced loss in lumen diameter, scaffold diameter and less neointimal growth when a higher wall thickness is used for the scaffold.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical scaffold, comprising:
    a set of rings including a proximal end ring, a distal end ring opposing the proximal end ring, and middle rings positioned between the end rings, wherein each ring is associated with its direct neighboring ring by links, and wherein at least one pair of neighboring middle rings can be delineated, via corresponding links there between, into closed cells comprising a W- or a general W-shaped zone included within the closed cell;

at least one of the links being a marker link, the marker link having a first cylindrical or part-cylindrical protrusion off a first side wall of the marker link for holding a first marker and a second cylindrical or part-cylindrical protrusion off a second, opposite side wall of the marker link for holding a second marker, wherein a distance of the first marker from an end point of the marker link is equal to the distance of the second marker from the same end point of the marker link such that the first and second protrusions are symmetrically aligned off of the marker link and are not longitudinally off-set from one another off of the marker link; and wherein the set of rings includes a minimum crimped diameter such that in the minimum crimped diameter, a pair of rings, between which the marker link resides, do not make contact with a bulging perimeter of the first and second protrusions, wherein the rings include crowns and struts, each link adjoining a pair of the neighboring rings at a crown of each ring, and wherein minimum crimped diameter (MCD) is less than a value derived from equation 1 or equation 2:

$$MCD < (\Sigma Swi + \Sigma Crj + \Sigma Lwk)*(\pi)^{-1} + 2*WT \quad \text{(equation 1)}$$

$$MCD < (\Sigma Swi + \Sigma Crj + \Sigma Lwk)*(\pi)^{-1} \quad \text{(equation 2)}$$

such that $\Sigma$ Swi (i=1 . . . n) is the sum of n ring struts having width Swi;

$\Sigma$ Crj (j=1 . . . m) is the sum of m crown inner radii having radii Crj (times 2);

$\Sigma$ Lwk (k=1 . . . p) is the sum of p links having width Lwk; and

WT is a ring wall thickness.

2. The implantable medical scaffold of claim 1, wherein at least some of the struts have an aspect ratio (AR) of 0.8 to 1.4, AR being defined as ratio of width to thickness.

3. The implantable medical scaffold of claim 2, wherein at least some of the links have an AR of 0.4 to 0.9.

4. The implantable medical scaffold of claim 1, wherein the marker link is longer than the links which do not have a marker.

5. The implantable medical scaffold of claim 1, wherein the crowns have a crown angle of less than 115 degrees.

6. The implantable medical scaffold of claim 1, wherein a pre-crimped crown angle is greater than a deployment crown angle.

7. The implantable medical scaffold of claim 1, wherein the first protrusion and the second protrusion including the first and second markers are circumferentially off-set from the marker link and spaced from the pair of rings associated with the marker link.

8. The implantable medical scaffold of claim 1, wherein each pair of neighboring middle rings forms only 4 closed cells.

9. The implantable medical scaffold of claim 1, wherein the middle rings comprise a network of circumferentially positioned closed cells and longitudinally positioned closed cells, the circumferentially positioned closed cells can be numbered 1 to n, and the longitudinally positioned closed cells can be numbered 1 to m, such that the odd numbered longitudinally positioned closed cells are in phase with each other, the even numbered longitudinally positioned closed cells are in phase with each other, and the odd numbered cells and even numbered cells longitudinally positioned closed cells are out of phase with each other.

10. The implantable medical scaffold of claim 9, wherein n is 4.

11. The implantable medical scaffold of claim 1, wherein at least one pair of the neighboring middle rings is adjoined by middle links, each middle link is associated with one crown of one ring and another crown of the neighboring ring, such that each middle link and its corresponding crown for the one ring form a generally "Y" shaped structure and each middle link and its corresponding crown for the neighboring ring form a generally "W" shaped structure.

12. The implantable medical scaffold of claim 1, wherein the marker link and two strut segments of a ring associated with the marker link form a "Y" shaped segment.

13. The implantable medical scaffold of claim 1, wherein the rings are approximately zig-zag like in pattern.

14. The implantable medical scaffold of claim 1, wherein the rings are curved like in pattern.

15. The implantable medical scaffold of claim 1, wherein all of the links are parallel to a longitudinal axis of a tubular device made from the rings and links.

16. The implantable medical scaffold of claim 1,
wherein the marker link runs parallel to a longitudinal axis of a tubular device made from the rings and links,
wherein the first marker is oriented at a distance and circumferentially from the second marker, and
wherein the first marker at least partially overhangs from the first side wall and the second marker at least partially overhangs from the second side wall.

17. The implantable medical scaffold of claim 1, wherein the rings comprise a first ring, a second ring, and a third ring, the second ring being positioned between the first and third rings, wherein the links residing between the first ring and the second ring are circumferentially off-set from the links residing between the second ring and the third ring.

18. The implantable medical scaffold of claim 17,
wherein the first and second rings, including the links there between, define a first set of closed cells each having a W- or general W-shaped configuration,
wherein the second and third rings, including the links there between, define a second set of closed cells each having a W- or general W-shaped configuration, and
wherein the W- or general W-shaped configurations of the first set of closed cells are circumferentially off-set from the W- or general W-shaped configurations of the second set of closed cells.

19. The implantable medical scaffold of claim 18, wherein the first set consists of 4 closed cells and the second set consists of 4 closed cells, and further wherein each cell consists of 4 crowns that are not connected to any links.

20. The implantable medical scaffold of claim 1,
wherein the links between a first pair of rings are out of phase or circumferentially off-set from the links between a second pair of rings, the first pair of rings and the second pair of rings sharing a common middle ring; and
wherein the links between the first pair of rings are in phase or not circumferentially off-set from the links between a third pair of rings, the second pair of rings and the third pair of rings sharing a common middle ring.

21. The implantable medical scaffold of claim 1, wherein the rings comprise a first ring, a second ring next to the first ring, a third ring next to the second ring, the second ring being in between the first and third rings, and a fourth ring next to the third ring, the third ring being in between the second and fourth rings, wherein the links between the first ring and the second ring are circumferentially offset from the links between the second ring and third ring, wherein the links between the second ring and the third ring are circumferentially offset from the links between the third ring and the fourth ring, and wherein the links between the first ring and the second ring are aligned with and not circumferentially offset from the links between the third ring and fourth ring, all links running parallel to a longitudinal, central axis of a tubular device made from the rings and links.

22. The implantable medical scaffold of claim 1, wherein each of the closed cells consists of 4 link-free crowns.

23. The implantable medical scaffold of claim 1, wherein every other crown is associated with a link.

24. An implantable medical scaffold, comprising:
a set of rings including a proximal end ring, a distal end ring opposing the proximal end ring, and middle rings positioned between the end rings, wherein each ring is associated with its direct neighboring ring by links, and wherein at least one pair of neighboring middle rings can be delineated, via corresponding links there between, into closed cells comprising a W- or a general W-shaped zone included within the closed cell;
at least one of the links being a marker link, the marker link having a first cylindrical or part-cylindrical protrusion off a first side wall of the marker link for holding a first marker and a second cylindrical or part-cylindrical protrusion off a second, opposite side wall of the marker link for holding a second marker, wherein a distance of the first marker from an end point of the marker link is equal to the distance of the second marker from the same end point of the marker link such that the first and second protrusions are symmetrically aligned off of the marker link and are not longitudinally off-set from one another off of the marker link:
wherein the set of rings includes a minimum crimped diameter such that in the minimum crimped diameter, a pair of rings, between which the marker link resides, do not make contact with a bulging perimeter of the first and second protrusions, wherein at least one of the middle rings has undulated segments and a repeating pattern of "Y" shaped and "W" shaped constructions where the undulated segments meet the links, and wherein the pattern further includes an undulated segment that is link-free between each "Y" and "W" shaped construction.

25. The implantable medical scaffold of claim 24,
wherein the undulating segments include crowns and struts, each link adjoining a pair of the neighboring rings at a crown of each ring, and
wherein minimum crimped diameter (MCD) is equal to a value derived from equation 1 or equation 2:

$$MCD < (\Sigma Swi + \Sigma Crj + \Sigma Lwk) * (\pi)^{-1} + 2*WT \quad \text{(equation 1)}$$

$$MCD < (\Sigma Swi + \Sigma Crj + \Sigma Lwk) * (\pi)^{-1} \quad \text{(equation 2)}$$

such that
$\Sigma$ Swi (i=1 ... n) is the sum of n ring struts having width Swi;
$\Sigma$ Crj (j=1 ... m) is the sum of m crown inner radii having radii Crj (times 2);
$\Sigma$ Lwk (k=1 ... p) is the sum of p links having width Lwk; and
WT is a ring wall thickness.

26. The implantable medical scaffold of claim 25, wherein at least some of the struts have an aspect ratio (AR) of 0.8 to 1.4, AR being defined as ratio of width to thickness.

27. The implantable medical scaffold of claim 26, wherein at least some of the links have an AR of 0.4 to 0.9.

28. The implantable medical scaffold of claim 24, wherein each undulating segment comprises a pair of struts adjoined by a crown, the scaffold is a stent such that the minimum crimped diameter is an inner diameter of the stent when the following step is performed: bending each undulating segment such that after bending, the pair of struts adjoined by the crown of each undulating segment is separated by a distance of about zero or the pair of struts is touching each other.

29. The implantable medical scaffold of claim 24, wherein each ring is composed of strut segments such that each strut segment has an aspect ratio (AR) of 0.8 to 1.4, AR being defined as ratio of width to thickness.

30. The implantable medical scaffold of claim 24, wherein at least some of the links have an aspect ratio of (AR) 0.4 to 0.9, AR being defined as ratio of width to thickness.

31. An implantable medical scaffold, comprising:
a set of rings, including a set of middle rings, forming an open tubular body,
a plurality of links, wherein each ring is associated with a neighboring ring by links, and
at least one of the links positioned between a first ring and a second ring being designated as a marker link, the marker link running parallel to a longitudinal axis of the tubular body, the marker link having a first overhang off of a first side of the marker link for holding a first marker and a second overhang off of a second, opposite side of the marker link for holding a second marker,
wherein the first marker and second marker are positioned at a distance in a circumferential arrangement with respect to each other such that the first marker at least partially extends out from the first side of the marker link and the second marker at least partially extends out from the second side of the marker link,
wherein the position of the first overhang from the first side of the marker link mirrors the position of the second overhang from the second opposite side of the marker link such that the overhangs are not longitudinally offset from each other,
wherein the set of rings includes a folded or crimped configuration and an expanded or dilated configuration such that in the folded or crimped configuration the first and second rings adjoining the marker link do not make contact with an exposed perimeter surface of the first and second overhangs, and
wherein the first overhang and second overhang including the first and second markers are arranged circumferentially off of the marker link and spaced from the first and second rings, such that a crimped profile of the tubular body can be as small as the crimped profile of a same tubular body but without the first and second overhangs, and
wherein at least one of the middle rings has undulated segments and a repeating pattern of "Y" shaped and "W" shaped constructions where the undulated segments meet the links, and wherein the pattern further includes an undulated segment that is link-free between each "Y" and "W" shaped construction.

32. The implantable medical scaffold of claim 31, wherein first ring includes an alternating pattern of peaks and troughs and the second ring includes an alternating pattern of peaks and troughs, such that there is at least one peak or trough for the first ring that is free from any links between the links that connect the first ring to the second ring, and such that there is at least one peak or trough for the second ring that is free from any links between the links that connects the first ring to the second ring.

33. The implantable medical scaffold of claim 31, wherein each ring is composed of a set of strut segments such that at least some of the strut segments have an aspect ratio (AR) of 0.8 to 1.4, and wherein at least some of the links have an AR of 0.4 to 0.9, AR being defined as ratio of width to thickness.

34. The implantable medical scaffold of claim 31, wherein the marker link and a first and second strut segment of the first ring form a generally Y-shaped construction.

35. The implantable medical scaffold of claim 31, additionally comprising a third ring connected to the second ring by links, wherein the second and third rings by means of the links define a set of closed cell patterns having a "W" or a generally "W" outlined configuration.

36. The implantable medical scaffold of claim 35, wherein the set consists of 4 close cell patterns and wherein each closed cell consists of 4 junctions that are not attached to any links.

\* \* \* \* \*